Figure 1:
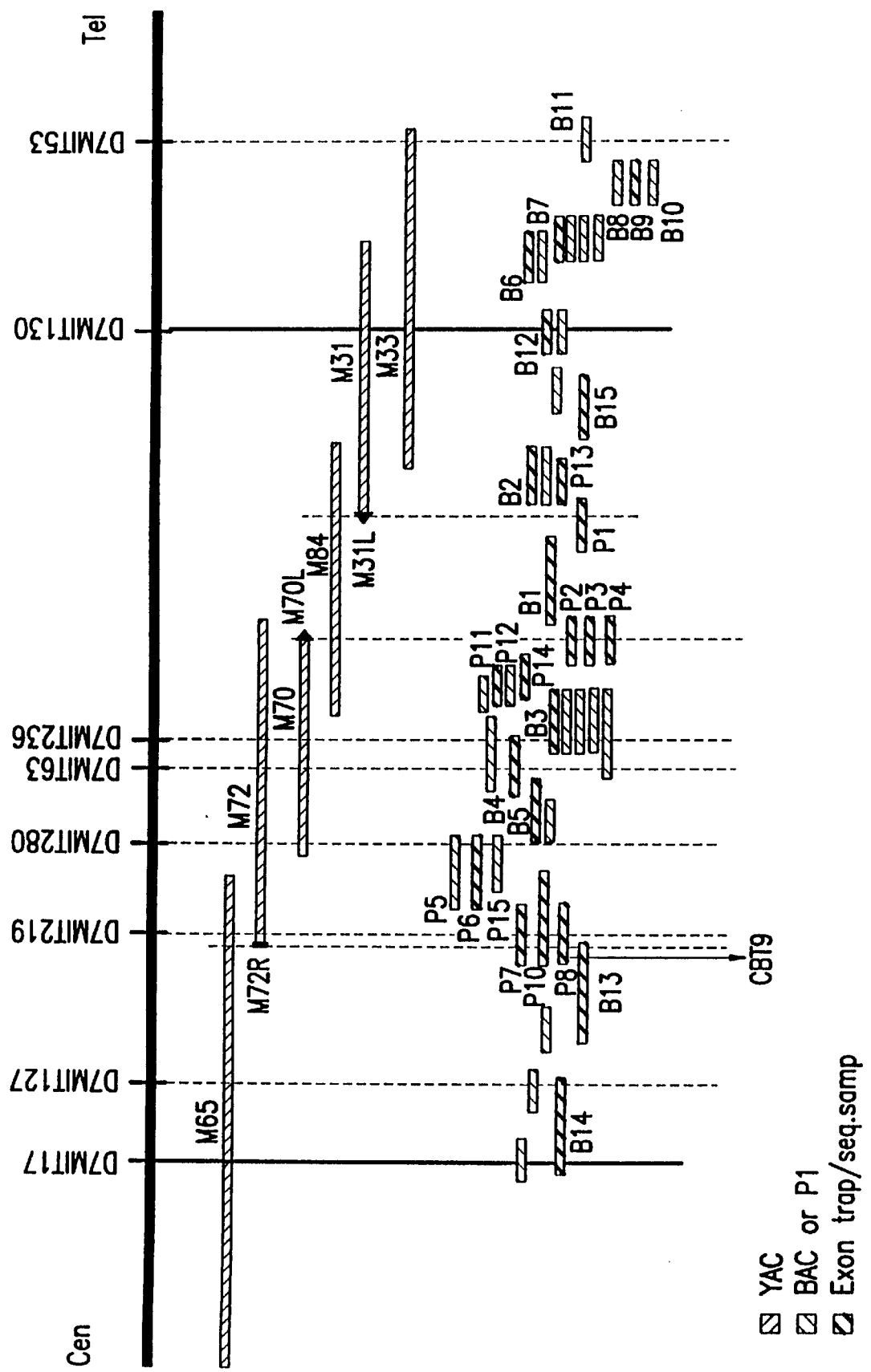

US005861239A

United States Patent [19]
Kleyn et al.

[11] Patent Number: 5,861,239
[45] Date of Patent: Jan. 19, 1999

[54] METHODS FOR IDENTIFYING COMPOUNDS THAT MODULATE MAMMALIAN TUB PROTEIN ACTIVITY

[75] Inventors: Patrick W. Kleyn, Cambridge; Karen J. Moore, Maynard; Rosana Kapeller, Chestnut Hill, all of Mass.

[73] Assignee: Millennium Pharmaceuticals, Inc., Cambridge, Mass.

[21] Appl. No.: 922,267

[22] Filed: Sep. 2, 1997

Related U.S. Application Data

[60] Continuation-in-part of Ser. No. 829,553, Mar. 28, 1997, Pat. No. 5,817,762, which is a division of Ser. No. 631,200, Apr. 12, 1996, Pat. No. 5,646,040.

[51] Int. Cl.$^6$ .............................. C12Q 1/00; C12Q 1/02
[52] U.S. Cl. .................................................... 435/4
[58] Field of Search ..................................... 435/4

[56] References Cited

PUBLICATIONS

Friedman, J.M. et al., 1991, "Molecular Maping of Obesity Genes", Mamm. Genome 1:130–144.
Bray, G.A., 1992, "Genetic, Hypothalamic and Endocrine Features of Clinical and Experimental Obesity", Prog. Brain Res. 93:333–341.
Friedman, J.M. and Leibel, R.L., 1992, "Tackling a Weighty Problem", Cell 69:217–220.
Coleman, D.L. and Eicher, E.M., 1990, "Fat (fat) and Tubby (tub): Two Autosomal Recessive Mutations Causing Obesity Syndromes in the Mouse", J. Hered. 81:424–427.
Jones, J.M. et al., 1992, "Localization of Insulin–2 (Ins–2) and the Obesity Mutant Tubby (tub) to Distinct Regions of Mouse Chromosome 7", Genomics 14:197–199.
Warden, C.H. et al., 1993, "Coincidence of Genetic Loci for Plasma Cholesterol Levels and Obesity in a Multifactorial Mouse Model", J. Clin. Inves. 92:773–779.
Nishina, P.M. et al., 1994, "Characterization of Plasma Lipids in Genetically Obest Mice: The Mutants Obese, Diabetes, Fat, Tubby, and Lethal Yellow", Metabolism 43:549–553.
Nishina, P.M. et al., 1994, "Atherosclerosis in Genetically Obest Mice: The Mutants Obese, Diabetes, Fat, Tubby, and Lethal Yellow", Metabolism 43:554–558.
Seldin, M.F. et al., "Glycogen Synthase: A Putative Locus for Diet–Induced Hyperglycemia", J. Clin. Invest. 94:269–276.
West, D.B. et al., 1994, "Genetics of Dietary Obesity in AKR/J X SWR/J Mice: Segregation of the Trait and Identification of a Linked Locus on Chromosome 4", Mamm. Genome 5:546–552.
Warden, C.H. et al., 1995, "Identification of Four Chromosomal Loci Determining Obesity in a Multifactorial Mouse Model", J. Clin. Invest. 95:1545–1552.
Samuelson, L.C. et al., 1995, "Localization of the Murine Cholecystokinin A and B Receptor Genes", Mamm. Genome 6:242–246.
Ohlemille, K.K. et al., 1996, "Cochlear and Retinal Degeneration in the tubby Mouse", Neuroreport 6:845–849.

Heckenlively, J.R. et al., 1995, "Mouse Model for Usher Syndrome: Linkage Mapping Suggests Homology to Usher Type I Reported at Human Chromosome 11p15", Proc. Natl. Acad. Sci. USA 92:11100–11104.
Chung, W.K. et al., 1996, "Molecular Mapping of the Tubby (tub) Mutation on Mouse Chromosome 7", Genomics 32:210–217.
Genbank Accession No. X69827 NCBI Entrez Record.
Vambutas, V. and Wolgemuth, D.J., 1994, "Identification and Characterization of the Developmentally Regulated Pattern of Expression in the Testis of a Mouse Gene Exhibiting Similarity to the Family of Phosphodiesterases", Biochim. Biophys. Acta 1217:203–206.
Genbank Accession No. Z48334 NCBI Entrez Record.
Wilson, R. et al., 1994, "2.2 Mb of Contiguous Nucleotide Sequence from Chromosome III of *C. elegans*", Nature 368:32–38.
Genbank Accession No. Z50688 NCBI Entrez Record.
Genbank Accession No. H92408 NCBI Entrez Record.
Bray, GA, 1989, "1989 McCollum Award Lecture, Genetic and Hypothalamic Mechanisms for Obesity—Finding the Needle in the Haystack" Am. J. Clin. Nur. 50:891–902.
Borjeson, M., 1976, "The Aetiology of Obesity in Children", Acta. Paediatr. Scand. 65:279–287.
Chen, H. et al., "Evidence That the Diabetes Gene Encodes the Leptin Receptor: Identification of a Mutation in the Leptin Receptor Gene in db/db Mice", Cell 84:491–495.
Coleman, D.L., 1978, "Obese and Diabetes: Two Mutant Genes Causing Diabetes–Obesity Syndromes in Mice", Diabetologia 14:141–148.
Grundy and Barnett, 1990, "Metabolic and health complications of obesity", Dis. Mon. 36:641–731.
Heckenlively, 1988, in Retinitis Pigmentosa, Heckenlively, ed., Lippincott, Philadelphia, pp. 221–235.
Herberg and Coleman, 1977, "Laboratory Animals Exhibiting Obesity and Diabetes Syndromes", Metabolism 26:59–99.
Kleyn, P. et al., 1996, "Identification and Characterization of the Mouse Obesity Gene tubby: A Member of a Novel Gene Family", Cell 85:281–290.
Knoll, J.H. et al., 1993, "Cytogenetic and Molecular Studies in the Prader–willi and Angleman Syndromes an Overview", Am. J. Med. Genet. 46:2–6.
Marshall, E., 1995, "Gene Therapy's Growing Pains", Science 269:1050–1055.

(List continued on next page.)

*Primary Examiner*—Johnny F. Railey, II
*Attorney, Agent, or Firm*—Pennie & Edmonds, LLP

[57] ABSTRACT

The present invention relates to the identification of novel nucleic acid molecules and proteins encoded by such nucleic acid molecules or degenerate variants thereof, that participate in the control of mammalian body weight. The nucleic acid molecules of the present invention represent the gene corresponding to the mammalian tub gene, a gene that is involved in the regulation of body weight. The present invention also relates to methods for identifying compounds that modulate tub protein activity.

12 Claims, 33 Drawing Sheets

OTHER PUBLICATIONS

Michaud, E. et al., 1994, "Differential Expression of a New Dominant Agouti Allele ($A^{iapy}$) is Correlated with Methylation State and is Influenced by Parental Lineage", Genes Devel. 8:1463–1472.

Moll, et al., 1991, "The Genetic and Environmental Sources of Body Mass Index Variability: The Muscatime Ponderosity Family Study", Am. J. Hum. Gen. 49:1243–1255.

Naggert, J. et al., 1995, "Hyperproinsulinaemia in Obese fat/fat Mice Associated with a Carboxypeptidase E Mutation which Reduces Enzyme Activity", Nature Genetics 10:135–141.

Noben–Trauth, K. et al., 1996, "A Candidate Gene for the Mouse Mutation Tubby", Nature 380:534–538.

Leibel, R. et al., 1990, in "Genetic Variation and Nutrition in Obesity", Simopoulos AP, Childs B (eds): Genetic Variation and Nutrition. World Rev. Nutr. Diab. Basel, Karger, Switzerland, vol. 63, pp. 90–101.

Stunkard, 1990, "The Body–Mass Index of Twins Who Have Been Reared Apart", N. Eng. J. Med. 322:1483–1487.

Tartaglia, L.A. et al., 1995, "Identification and Expression Cloning of a Leptin Receptor", Cell 83:1263–1271.

Zhang, Y et al., 1994, "Positional Cloning of the Mouse Obese Gene and its Human Homologue", Nature 372:425–432.

Breen et al., 1994, "Towards high resolution maps of the mouse and human genomes—a facility for ordering markers to 0.1 cM resolution", Human Mol. Genetics 3:621–627.

Dietrich et al., 1992, "A Genetic Map of the Mouse Suitable for Typing Intraspecific Crosses", Genetics 131:423–447.

Kozak, M., 1987, "An analysis of 5'–noncoding sequences from 699 vertebrate messenger RNAs", Nuc. Acids. Res. 15:8125–8132.

Kunkel, T.A., 1985, "Rapid and efficient site–specific mutagenesis without phenotypic selection", PNAS USA 82:488–491.

Whitney, J.B. III, 1978, "Simplified Typing of Mouse Hemoglobin (Hbb) Phenotypes Using Cystamine", Biochem. Genet. 16:667–672.

```
GGATGCGGCCCGGGGGGCCCGGGGCCCGGGGGCCCGAGAGTTGAGCAGGTCCCCGCCCCAGCCCGAGCGTCCCCGCCCCGAGCGGTCCCCGCCACCGAGCCGCAG
CCGCCGCCCCCGGGAGA                                                           CTGCAGGATTCGGCACGAGCAGCGGTCGGCCGGGA

M   T   S   K   P   H   S   D   W   I   P   Y   S   V              14
                  ATG ACT TCC AAG CCG CAT TCC GAC TGG ATT CCT TAC AGT GTC             42

L   D   D   E   G   S   N   L   R   Q   Q   K   L   D   R   Q   Q   R   A   L   L    34
CTA GAT GAT GAG GGC AGC AAC CTG AGG CAG CAG AAG CTC GAC CGG CAG CAG CGG GCC CTG TTG   102

E   Q   Q   K   K   K   R   Q   E   P   L   M   V   Q   A   N   A   D   G           54
GAA CAG CAG AAG AAG AAG CGC CAA GAG CCC TTG ATG GTA CAG GCC AAT GCA GAT GGA          162

R   P   R   S   R   R   A   R   Q   S   E   Q   E   E   Q   A   P   L   V   E   S   Y  74
CGG CCC CGG AGT CGG CGA GCC CGG CAG TCA GAG CAG GAG CAA GCC CCC CTG GTG GAG TCC TAC   222

L   S   G   S   T   S   Y   Q   V   Q   E   A   D   S   I   A   S   V           94
CTC AGC AGT AGT ACC AGC TAC CAA GTT CAA GAG GCC GAC TCG ATT GCC AGT GTA           282

Q   L   G   A   T   R   P   P   A   P   R   K   E   K   K   G   K   A   A           114
CAG CTG GGA GCC ACC CGC CCA CCA GCA CCA AGG AAG GAG AAG AAG GGA AAG GCG GCT           342

A   S   G   G   Q   G   G   A   P   R   K   E   K   K   H   K   G   T               134
GCA TCT GGG GGC CAG GGT GGA GCC CCT AGG AAG GAG AAG AAG CAT AAA GGC ACC              402
```

FIG.6A

|     |     |     |     |     |     |     |     |     |     |     |     |     |     |     |     |     |     |     |     | |
|-----|-----|-----|-----|-----|-----|-----|-----|-----|-----|-----|-----|-----|-----|-----|-----|-----|-----|-----|-----|---|
| S   | G   | P   | A   | T   | L   | A   | E   | D   | K   | S   | E   | A   | Q   | G   | P   | V   | Q   | I   | L   | 154 |
| AGC | GGG | CCA | GCA | ACT | CTG | GCA | GAA | GAC | AAG | TCT | GAG | GCC | CAA | GGC | CCA | GTG | CAG | ATC | TTG | 462 |
| T   | V   | G   | Q   | Q   | S   | D   | H   | D   | K   | D   | A   | A   | E   | T   | A   | G   | G   | G   | A   | 174 |
| ACT | GTG | GGA | CAG | CAG | TCA | GAC | CAC | GAC | AAG | GAT | GCG | GCA | GAG | ACA | GCC | GGC | GGG | GGC | GCA | 522 |
| Q   | P   | S   | G   | E   | Q   | D   | L   | R   | A   | R   | T   | M   | Q   | I   | S   | S   | S   | M   |     | 194 |
| CAG | CCC | AGT | GGG | GAG | CAG | GAC | CTC | CGT | GCC | AGG | ACG | ATG | CAG | ATC | TCC | AGC | AGC | ATG |     | 582 |
| S   | F   | D   | E   | D   | E   | N   | E   | D   | T   | M   | S   | S   | S   | S   | G   | S   | L   | N   | S   | 214 |
| AGC | TTT | GAC | GAG | GAT | GAG | AAC | GAA | GAT | ACG | ATG | AGC | TCC | AGC | TCC | GGC | AGC | CTA | AAC | AGC | 642 |
| N   | T   | R   | P   | S   | A   | P   | Q   | S   | T   | I   | R   | E   | A   | S   | P   |     |     |     |     | 234 |
| AAC | ACC | CGC | CCT | AGT | GCC | CCT | CAG | TCT | ACT | ATC | AGA | GAG | GCA | TCA | GCC |     |     |     |     | 702 |
| S   | P   | A   | A   | P   | E   | P   | Q   | G   | I   | T   | Y   | D   | L   | E   | E   | F   | A   |     |     | 254 |
| AGC | CCA | GCC | GCC | CCA | GAG | CCC | CAA | GGG | ATC | ACC | TAC | GAT | CTA | GAG | GAG | TTT | GCA |     |     | 762 |
| L   | R   | A   | G   | Q   | M   | Y   | P   | I   | T   | K   | C   | R   | V   | D   | K   | E   | D   | K   | G   | 274 |
| CTG | AGG | GCA | GGG | CAA | ATG | TAC | CCC | ATC | ACT | AAA | TGC | CGC | GTC | GAC | AAG | GAG | GAC | AAG | GGG | 822 |
| M   | D   | R   | G   | M   | Y   | P   | T   | Y   | F   | L   | H   | L   | D   | R   | E   | D   | G   | K   | K   | 294 |
| ATG | GAC | CGC | GGC | ATG | TAC | CCC | ACC | TAC | TTT | CTG | CAC | CTA | GAC | CGT | GAG | GAT | GGC | AAG | AAG | 882 |
| V   | F   | L   | A   | G   | R   | K   | R   | K   | K   | S   | K   | T   | S   | N   | Y   | L   | I   | S   |     | 314 |
| GTG | TTC | CTC | GCG | GGC | AGG | AAG | AGA | AAG | AAG | AGT | AAA | ACT | TCC | AAT | TAC | CTC | ATC | TCT |     | 942 |

FIG. 6B

| | | | | | | | | | | |
|---|---|---|---|---|---|---|---|---|---|---|
| V | D | P | T | D | L | S | R | G | G | D | S | Y | I | G | K | L | R | S | N | 334 |
| GTG | GAC | CCA | ACA | GAC | TTG | TCT | CGG | GGA | GGC | GAT | AGC | TAT | ATC | GGG | AAA | TTG | CGG | TCC | AAC | 1002 |

| L | M | G | T | K | F | T | V | Y | D | N | G | N | P | Q | K | A | S | 354 |
|---|---|---|---|---|---|---|---|---|---|---|---|---|---|---|---|---|---|---|
| CTG | ATG | GGC | ACC | AAG | TTC | ACC | GTT | TAT | GAC | AAT | GGC | AAC | CCT | CAG | AAG | GCA | TCC | 1062 |

S T L E S G T L R Q E L A A V C Y E T N 374
TCC ACG CTG GAA AGC GGA ACC TTG CGC CAG GAG CTG GCA GCG TGC TAT GAG ACA AAT 1122

V L G F K G P R K M S V I V P G M N M V 394
GTC CTA GGC TTC AAG GGA CCT CGG AAG ATG AGT GTG ATC GTC CCA GGC ATG AAC ATG GTT 1182

H E R V C I R P N E H E T L A R W Q 414
CAT GAG AGA GTC TGT ATC CGC CCC AAT GAA CAT GAG ACC CTG TTA GCA CGC TGG CAG 1242

N K N T E S I E L Q N K T P V A D 434
AAC AAG AAC ACG GAG AGC ATC ATT GAG CTG CAG AAC AAG ACG CCA GTC GCT TGG AAT GAT GAC 1302

T Q S Y V L N F H G R V T Q A S V K N F 454
ACA CAG TCC TAT GTA CTT AAC TTC CAC GGC CGT GTC ACA CAG GCT TCT GTG AAG AAC TTC 1362

Q I H G N D P Y D Y I V M Q F G R V A E 474
CAG ATC CAC GGC AAT GAC CCG TAC GAC TAC ATC GTC ATG CAG TTT GGC CGG GTA GCA GAA 1422

FIG.6C

```
         D   V   F   T   M   D   Y   N   Y   P   L   C   A   L   Q   A   F   A   I   A   494
         GAT GTG TTC ACC ATG GAT TAC AAC TAC CCA CTG TGT GCA CTG CAG GCC TTC GCC ATT GCT  1482

L   S   S   F   D   S   K   L   A   C   E   *                                   505
         CTG TCC AGC TTT GAC AGC AAG CTG GCC TGC GAG TAG AGGCCCCCACTGCCGTTAGGTGGCCCAGTC   1515

CGGAGTGGAGCTTGCCTGCCAAGACAGGCCTGCCTACCCTCTGTTCATAGGCCCTCTATGGGCTTTCTGGTCTGA

CCAACCAGAGATTGGTTTGCTCTGCCCTCTGCTGCTTGA
```

FIG.6D

```
tubgenomic    ACGGCAATGA  CCTGAGTGT   TGCCACTCCC  TGTTTTTGAT
B6genomic     ACGGCAATGA  CCGTGAGTGT  TGCCACTCCC  TGTTTTTGAT
tubcdna       ACGGCAATGA  CCTGAGTGT   TGCCACTCCC  TGTTTTTGAT
B6cdna        ACGGCAATGA  CC::::::::  ::::::::::  ::::::::::

1            ********** *:******  ******  ******** tubgenomic    GTTGTACGCA  TGGTGCCCAG  CCCCCACCCC  ACCCCCAATC
B6genomic     GTTGTACGCA  TGGTGCCCAG  CCCCCACCCC  ACCCCCAATC
tubcdna       GTTGTACGCA  TGGTGCCCAG  CCCCCACCCC  ACCCCCAATC
B6cdna        ::::::::::  ::::::::::  ::::::::::  ::::::::::

41           ********  ******  ******  ******** tubgenomic    CCCTGATCTG  GTCCATATCA  GCCAGTGATG  GGATGTGGGT
B6genomic     CCCTGATCTG  GTCCATATCA  GCCAGTGATG  GGATGTGGGT
tubcdna       CCCTGATCTG  GTCCATATCA  GCCAGTGATG  GGATGTGGGT
B6cdna        ::::::::::  ::::::::::  ::::::::::  ::::::::::

#81           **********  **********  **********  **********
```

FIG.7A

| | | | | | |
|---|---|---|---|---|---|
| tubgenomic | ATATGGCTTT | TGTTAGAACT | TTCTAACTGT | AGTGATCTAG |
| B6genomic | ATATGGCTTT | TGTAAGAACT | TTCTAACTGT | AGTGATCTAG |
| tubcdna | ATATGGCTTT | TGTTAGAACT | TTCTAACTGT | AGTGATCTAG |
| B6cdna | :::::::::: | :::::::::: | :::::::::: | :::::::::: |
| #121 | ********** | *** ****** | ********** | ********** |
| tubgenomic | AGTCCTGCCC | CTAGTGCCCT | GCATGTCTGG | GGCTTGGGAA |
| B6genomic | AGTCCTGCCC | CTAGTGCCCT | GCATGTCTGG | GGCTTGGGAA |
| tubcdna | AGTCCTGCCC | CTAGTGCCCT | GCATGTCTGG | GGCTTGGGAA |
| B6cdna | :::::::::: | :::::::::: | :::::::::: | :::::::::: |
| #161 | ********** | ********** | ********** | ********** |
| tubgenomic | TACCCTTTAA | ATGGATGTCT | TTTCTCTCCT | GGGCCCTGCT |
| B6genomic | TACCCTTTAA | ATGGATGTCT | TTTCTCTCCT | GGGCCCTGCT |
| tubcdna | TACCCTTTAA | ATGGATGTCT | TTTCTCTCCT | GGGCCCTGCT |
| B6cdna | :::::::::: | :::::::::: | :::::::::: | :::::::::: |
| #201 | ********** | ********** | ********** | ********** |

FIG. 7B

```
tubgenomic   GTCTGTGTGC ATCTCCCCCC TTCACCCTCT TGCTTCATAA
B6genomic    GTCTGTGTGC ATCTCCCCCC TTCACCCTCT TGCTTCATAA
tubcdna      GTCTGTGTGC ATCTCCCCCC TTCACCCTCT TGCTTCATAA
B6cdna       :::::::::: :::::::::: :::::::::: ::::::::::

241         ******** ****** ****** ******** tubgenomic   TGTTTCTCTT GAACCTTTGT TTTGTTCATC CTTTCGATCT
B6genomic    TGTTTCTCTT GAACCTTTGT TTTGTTCATC CTTTCGATCT
tubcdna      TGTTTCTCTT GAACCTTTGT TTTGTTCATC CTTTCGATCT
B6cdna       :::::::::: :::::::::: :::::::::: ::::::::::

281         ******** ****** ****** ******** tubgenomic   CTTTGGCATT TCTGCTTTCT CCTTCCCTCT TGTGGCCCAT
B6genomic    CTTTGGCATT TCTGCTTTCT CCTTCCCTCT TGTGGCCCAT
tubcdna      CTTTGGCATT TCTGCTTTCT CCTTCCCTCT TGTGGCCCAT
B6cdna       :::::::::: :::::::::: :::::::::: ::::::::::

#321         ********** ********** ********** **********
```

FIG. 7C

```
tubgenomic  GTCTTACCTG  GTCTCCCTGT  CTCCACCATT  CTTGCTTGTG
B6genomic   GTCTTACCTG  GTCTCCCTGT  CTCCACCATT  CTTGCTTGTG
tubcdna     GTCTTACCTG  GTCTCCCTGT  CTCCACCATT  CTTGCTTGTG
B6cdna      ::::::::::  ::::::::::  ::::::::::  ::::::::::

361        ********  ******  ******  ******** tubgenomic  CATTCCACAG  CGGACTACAT  CGTCATGCAG  TTTGGCC
B6genomic   CATTCCACAG  CGGACTACAT  CGTCATGCAG  TTTGGCC
tubcdna     CATTCCACAG  CGGACTACAT  CGTCATGCAG  TTTGGCC
B6cdna      ::::::::::  CGGACTACAT  CGTCATGCAG  TTTGGCC

#401        **********  **********  **********  *******
```

FIG. 7D

```
AGCCCNCCGGTCCCGGGAGGATACGTCCCGGGGGCGCCCCCGGCCCTCGGCCTCGGGGGCCC
CCCGGGCCTCCAGAGCCGCAGCCACCGCGCCCCCGAGAGACGAGCTGAGCAGGCCCCCGCCGGCCCTCCGGGC
```

| | | | | | | | | | | | |
|---|---|---|---|---|---|---|---|---|---|---|---|
| M | T | S | K | P | H | S | D | W | | | 9 |
| ATG | ACT | TCC | AAG | CCG | CAT | TCC | GAC | TGG | | | 27 |
| I | P | Y | S | V | L | D | D | E | G | R | 29 |
| ATT | CCC | TAC | AGT | GTC | TTA | GAT | GAT | GAG | GGC | AGA | 87 |
| N | L | R | Q | K | L | D | R | | | | 49 |
| AAC | CTG | AGG | CAG | AAG | CTT | GAT | CGG | | | | 147 |
| Q | R | A | L | L | E | Q | K | Q | K | K | 69 |
| CAG | CGG | GCC | CTG | CTG | GAG | CAG | AAG | CAG | AAG | AAG | 207 |
| R | Q | E | P | L | M | V | Q | | | | 89 |
| CGC | CAG | GAG | CCC | CTG | ATG | GTG | CAG | | | | 267 |
| A | N | A | D | G | R | P | R | S | R | R | |
| GCC | AAT | GCA | GAT | GGG | CGG | CCC | CGG | AGC | CGG | CGG | |
| A | R | Q | S | E | E | Q | A | P | | | 109 |
| GCC | CGG | CAG | TCA | GAG | GAA | CAA | GCC | CCC | | | 327 |
| L | V | E | S | Y | L | S | S | G | A | T | |
| CTG | GTG | GAG | TCC | TAC | CTC | AGC | AGT | GGC | GCA | ACG | |
| R | P | T | S | Y | Q | V | Q | E | A | D | |
| AGC | AGT | AGC | AGT | TAC | CAA | GTT | CAA | GAG | GCC | GAC | |
| S | L | A | S | V | Q | L | G | A | T | R | P | 129 |
| TCA | CTC | GCC | AGT | GTG | CAG | CTG | GGA | GCC | ACG | CGC | CCA | 387 |
| A | P | A | R | K | E | K | R | | | | |
| GCT | CCA | GCA | GCT | AGG | AAG | GAG | AGA | | | | |
| T | K | A | A | T | A | G | G | Q | G | A | A | |
| ACC | AAG | GCG | GCA | ACT | GCA | GGG | CAG | GGT | GCC | GCT | GGC | |
| A | R | K | K | G | | | | | | | |
| GCC | AGG | AAG | AAG | GGA | | | | | | | |

FIG. 9A

```
  K   H   K   G   T   S   G   P   A   L   A   E   D   K   S   E   A   Q   G           149
  AAG CAC AAA GGC ACC AGC GGG CCA GCA CTG GCA GAA GAC AAG TCT GAG GCC CAA GGC          447

P   V   Q   I   L   T   V   G   Q   S   A   H   A   Q   D   A   G   E   T   A       169
  CCA GTG CAG ATT CTG ACT GTG GGC CAG TCA GCC CAC GCC CAG GAC GCA GGG GAG ACG GCA      507

A   G   G   E   R   P   S   G   Q   D   H   L   R   A   T   M   Q   R   K   G       189
  GCT GGT GGG GAA CGG CCC AGC GGG CAG GAT CAC CTC CGT GCC ACG ATG CAG AGG AAG GGC      567

I   S   S   M   S   F   D   E   D   Q   E   E   E   N   S   S   S   V   R           209
  ATC TCC AGC ATG AGC TTT GAC GAG GAT GAG GAG GAG AAT AGC TCC AGC TCC GTC AGG          627

S   S   Q   L   N   T   R   P   S   A   T   E   S   R   K   R   K   S   V   R       229
  TCC TCC CAG CTA AAT ACC CGC CCC AGC GCT GCT ACT GAG AGC AGG AAG AGG AAG TCC GTC AGG  687

E   A   A   S   A   P   E   Q   T   A   P   Q   G   I   T   I   K   C   R           249
  GAG GCA GCC TCA CCT AGC CCT ACA GAG CAA GCC CCC CAG GGT ATC ACC ATC AAA TGC CGC      747

D   L   E   E   F   A   L   R   P   A   P   Q   G   I   T   I   K   C   R   I       269
  GAT CTT GAG GAG TTT GCA CTG AGG CCG CCC CAG GGT ATC ACC ATC AAA TGC CGC ATC          807

T   R   D   K   G   M   D   R   G   M   Y   P   T   Y   F   L   H   L   D           289
  ACT CGG GAC AAG AAA GGG ATG GAC CGG GGC ATG TAC CCC ACC TAC TTT CTG CAC CTG GAC      867
```

FIG.9B

```
R    E    D    G    K    K    V    F    L    L    A    G    R    K    K    K    S    K    T                      309
CGT  GAG  GAT  GGG  AAG  AAG  GTG  TTC  CTC  CTG  GCG  GGA  AGG  AAG  AAG  AAG  AGT  AAA  ACT                    927

S    N    Y    L    I    S    V    D    P    T    D    L    S    R    G    G    D    Y    I                      329
TCC  AAT  TAC  CTC  ATC  TCT  GTG  GAC  CCA  ACA  GAC  TTG  TCT  CGA  GGA  GGG  GAC  TAT  ATC                    987

G    K    L    R    S    N    L    M    G    T    K    F    T    V    Y    D    N    G    V    N                 349
GGG  AAA  CTG  CGG  TCC  AAC  TTG  ATG  GGC  ACC  AAG  TTC  ACT  GTT  TAT  GAC  AAT  GGA  GTC  AAC               1047

P    Q    K    A    S    S    T    L    E    S    G    T    L    R    Q    E    A    A                           369
CCT  CAG  AAG  GCC  TCA  TCC  ACT  TTG  GAA  AGT  GGA  ACC  TTA  CGT  CAG  GAG  GCA  GCT                         1107

V    C    Y    E    T    N    V    L    G    F    K    G    P    R    K    M    S    V    I    V                 389
GTG  TGC  TAC  GAG  ACA  AAC  GTC  TTA  GGC  TTC  AAG  GGG  CCT  CGG  AAG  ATG  AGC  GTG  ATT  GTC               1167

P    G    M    N    M    V    H    E    R    V    S    I    R    P    N    E    H    E    T                      409
CCA  GGC  ATG  AAC  ATG  GTT  CAT  GAG  AGA  GTC  TCT  ATC  CGC  AAC  GAG  CAT  GAG  ACA                         1227

L    A    R    W    Q    N    K    N    T    E    S    I    I    E    L    Q    N    K    T                      429
CTG  GCA  CGC  TGG  CAG  AAT  AAG  AAC  ACG  GAG  AGT  ATC  ATC  GAG  CTG  CAA  AAC  AAG  ACA                    1287

P    V    W    N    D    D    T    Q    S    Y    V    L    N    F    H    G    R    V    T    Q                 449
CCT  GTC  TGG  AAT  GAT  GAC  ACA  CAG  TCC  TAT  GTA  CTC  AAC  TTC  CAT  GGG  CGC  GTC  ACA  CAG               1347
```

FIG. 9C

```
A    S    V    K    N    F    Q    I    I    H    G    N    D    P    D    Y    I    V    M    Q      469
GCC  TCC  GTG  AAG  AAC  TTC  CAG  ATC  ATC  CAT  GGC  AAT  GAC  CCG  GAC  TAC  ATC  GTG  ATG  CAG   1407

F    G    R    V    A    E    D    V    F    T    M    D    Y    N    Y    P    L    C    A    L      489
TTT  GGC  CGG  GTA  GCA  GAG  GAT  GTG  TTC  ACC  ATG  GAT  TAC  AAC  TAC  CCG  CTG  TGT  GCA  CTG   1467

Q    A    F    A    I    A    L    S    F    D    S    K    L    A    C    E    *                     506
CAG  GCC  TTT  GCC  ATT  GCC  CTG  TCC  TTC  GAC  AGC  AAG  CTG  GCG  TGC  GAG  TAG  AGGCCTC         1528

TTCGTGCCCTTGGGTTGCCCTGGAGGCGAGCTTGCCCTGCTGGAGACAGCCCTGCCTATCCTCTGTA                                  1607

TATAGGCCTTCGCCAGATGAAGCTTTGCCCTCAGTGGCCTCCTGCCCAGCAGCCAGGAACTGCTCCTTGGCT                             1686

CTGCTACTGAGGCAGGGAGTAGTGGAGAGCGTGGGTGTGAAGGATTGAGAATTAATTCTTTCCATGCCAC                               1765

GAGGATCAACAACACACTCCCACCCTTGGGTAGTAGTGGTACTTTACCAAAGCTTGAGCAACCTC                                    1844

TTCCAAGCTTGGGAAAGGCCCAAAAAGGCATTAGGAGGGGAG                                                           1888
```

FIG. 9D

```
AGCCTACAGTTTAAACAGTCGACTCTAGACTTAATTAAGGNTCCGGNGCG
CCCCCGGGTACCGAGCTCTGGTCTCCACCCACTGCCTGTTTCTCTCTCC
ATCTGGGGATGTTTCCTGAGTCAAGAGGCCGACTCACTGCCAGTG
TGCAGCTGGGAGCCACGCGCCAACAGCCCAACACCAGCTTCAGCAAGAGAACC
AAGGCGGCAGCTACAGCAGGGGCCAGGCGCGGCCGCGCTAGGAAGGAGAA
GAAGGGAAAGCACACAAAGTCAGCTCACATTCTCTACAGCCCTGCCCAGCA
GGCCTGGCCTCCACTCGTAGGGCTGGGAAGGTTTGTCCTCCTGACTTGGA
GGGGAGGGGATAGGATGAAACAGCCTCAGGGAAGACACAGACTGCCACTCTG
GGCACCCCCTCAGGTGGCTCACAGGCCTCATCTAGCTTGGGAGGTGCCTG
GGCTGCCTCTGGGTGTGGCCATGCCAACACTGCCAGGAAGTGAAGT
CCTGCTCAGCTTTGGCCCAGAACCACCGTCCCNANCTTNAGTTACTTTGG
CCTTGAGGAACCTTTATNATGACCCCNTNAAGGAGGATTTTAACCAAGCT
GGATT
```

FIG. 10A

TTCAAGGGCCAAAGTTTTTTAATGATGTATGGGAGTTAATGAAGGNGGTA
TGTGGGTNTGTTNGNGGAAGAAAAACACCAGCATTGATGGTTGTAGNTGKT
GGTGTCCAKGAATGATTGCTGGCCTTGCCTATGGTNTGGATCAGTCCTTG
TTNTCCCATCTTGTTTTTCCCATGTGCAGTTGGTTTTGTAGATGGCTG
CCGTCTGCTTTAAAGGACGTGAGGTGTAAACCAACCCTGCAATTA
ATTGGGGAAGCAGAAGAAATGAAGCCCAACATCCCTTACTAGCTTA
CCAGTTGTTAACAGGCTGGTGCAATCATTAGTTTTATAAAATCAGTTTT
GCAAATAAAGTTTTGCAGAGGGTTTCCCACTCTTCCCTCATCCCTTCA
TGGACGTCTGAGAATCCAGGCCCCTCCTCCTCCTGGATGTAACTCA
GGCGTGTCCGTGCCTGCAGGCCCAGCCAGCACTGGCAGAAG
ACAAGWCTGAGGCCCAAGGCCCAGTGCAGATTCTGACTGTGGGCCAGTCA
GACCACGCCCAGGAGACGGCAGCAGCTGGTGGGGCGAACGGCC
CAGCGGGCAGGATCTCCGTKCCACGATGCAGAGGAAGAAGGTGAGCCCCATG
GGGGCCCCAGTGCGATACCCCAAAACTCAGTCCCAGTTCTCAGATGCACCT
TTCTCTGGGAGCATGGNCTTCCTGTGTCCAAACCCCTCCCTGCAATGGT
GGGTGAGGGTCACACTTCGGAGAGACAAATNAGAAACTCTTAGCAGG
GNCCCTGCTAAGGCCCCAGGGAGGCC

FIG.10B

TTAAACAGTCGACTCTAGACTTAATTAAGGATCCGGGCGCCCCGGTA
CCGAGCTCAGTGCAGGCCCTTGATACACAAGAGACAGTGGTAGGTGSCTG
CTAGGTAGTGGGGTAATGTGGCCAGACTGAGCTGAAACTGGTGGTGGGAT
ATATCCTGAGGATTGTGCCAGCCCCGGCTCATGTGTGTACCTGAGAGAA
TATCCTTTTATATCTGGACATGTGGAATATATGTGAATGGGAGTC
TATATGTGTAGATATGGCTAAGAGTGTGTGCATAAGTTTGTGGGTACA
GGTGAGTCAGTGTCTGAACATGAGTATGTGACCATGTATTTCAGGGC
AGGGTAGACTTCTCCTCATTCCCTTCTCTCTCCTTGGCCAGG
CATCTCCAGCAGCATGAGCTTTGACGAGGATGAGGAGGAGAGA
ATAGCTCCTCCCCAGCTAAATAGTAACACCCGCCCCCAGCTCTGCT
ACTAGCAGGAAGTCCGTCAGGGTGAGTGAGTGACTGCATCCACAGCAG
TTTTGGAGGACTGCTCATCCGTTAGAGGTGGACTGCATGTGAAGAGATG
GACTCGTATGCCTTTAGGAGCTTCTCTGCTGGCCCTTACGTCCCTCTAC
CTTGCCTCCTAACCTCTTCAGCTAGGCCAGCAGGACCCTCTGAGGTATGGGGGA
GATGCAGTTGGACAGGATGACCCTCTGAGGACCTCCCGTATCTCCCATCTC
CACCTCTAGGAACTGTTGAGGGCCCCCAGAGATCCTTCCCTCTCCCAC
AGGCCCAGCTGGCAGGCAGATTTGGATCCCAGACCACCAATTTGGCTGCT
CGCCACGTTAGGAGGCAGATTTGGATCCCAGACCACCAATTTGGCTGCT
TAGGGTCCTTGGGCTCAGGCACCCTTCGATCCCCCATAGGAGGCAGC
CTCAGCCCTAGCCAACAGCTCACTGAGGCCAACCAGTGACGTTGAGTCC
AGGATCTTGAGGAGTTTGCACTGGGACACCAGGGTATCACCATC
AAATGCCGCATCACTCGGGACAAGAAAGGGATGGACCGGGGCATGTACCC

FIG.10C

```
CACCTACTTTCTGCACCTGGACCGTGAGGATGGGAAGAAGGTAAGGTTGG
TCTGGGCATGTTATCATCTAGGCTTTACAGCCCTTGAAATCCTAGGGGC
TGAAATGTGACTGGAAGTCTCATATCTACCGCTGACCCTCTCAGTTCCTCA
AAGAAACTGCCTTCTGTGTCTCTGTCTGTGCACATCTTTGTGTTTCCAGTG
CATTTGTGTGTGCACATATGTGCGTTTGGGAGCTGACGCAACGGAGAG
AGTCTGTGTGAGTGGCTCTCATGACTGTGTGCAGACCAGAGGCTGAGTCT
GGAATATGACCCTCATTCCACTCCCCAAGTGTTCCTCCTGGCGGAAGGA
AGAGAAGAAGAGTAAACTTCAATTACTTCATCTCTGTGACCCAACA
GACTTGTCTCGAGGAGGGACAGCTATATCGGGAAACTGCGGTACTAGC
ATTCCCCAGGAGGAAGCAGGCCTGAATCTTCCTGAAGAGATCTAGGCCAAGCTG
TCTGTAGAGGGCCTGAATCCCTCTGATAATCACATCCAACTGGAGCCTATGTC
ACTCTCCAGGATCCTCCAGGCCTAGAGCCAGAGGACTCACACACCGACCCC
TATGCCAGCCTAGAGCCAGAGGTGGGTGCAGGCCCACCACCAAGAGTGATGGATCCAA
AAGCTGTTCCCAGGGTCACTGATAACGCAGGACAGGCTGAGAGTGAAGAGTTGCCTTGGC
CCCCAGGGCGTGCAATGCCAAGGGACAGGCTGAGAGTGAGCTCGGTACCCGGG
TCCATGGTCAATGCCAAGGGACAGGCTGAGAGTGAGCTCGGTACCCGGG
GGCGCKCCCGGATCCCTTAATTAAGTCTAGAGTCGACTGTTTAAG
```

FIG.10D

```
GATTTAGNGGAACACAGCACNCTTGNGGGTGGGANGGCAGTGGTGAAGGGG
CAGGAAGGCTCTGAGCCTAGGCCTCCAGGTGGGGCAGTGGGGAGGTAGG
GTTTGCTGAGGAACTGAGTACCAGAGATTTGGGAGCATAAATAAAGATGAG
AGTCAGGAGCTAAAGCTGGAGATGGGGCTGGACTGAGACTTAGGCTGGC
TGCGACAGAGAGGAGATCTCATCCTCTCCACGGGTGCTAAGCCTCTTCCA
CTGTCTTATCAGATGCCATTCTGTTGCTCACCTCCCATGAGGAGAACTC
CCATGTCCCAGATAAATCTYCTGAAGAATCTGATTGACCTCCCTGA
ATTGCTCTCACTGAACTGAAATGCACTTGAGTCAACTCAGAGCAAGTCC
AGGCCTTCTGCCCACGAAGTGTCTTCAAAGATGTGGATTCAGTGAGCAGT
ATGCCCTCCCTGGGCCTGTCCTCCAGCCACGATGAGCTGTCCCTGCTC
CTCATAGGACAGAGCTGTCTCTGCTTCCCTGGGCAGAGGTGCA
TGACTCTATACTGATTGTGCCTTTATTTCAGGTCCAACTTGATGGCCACC
AAGTTCACTGTTTATGACAATGAGTCAACCCTCAGAAGCCCTCATCCTC
CACTTTGGAAAGTGGAACCTTACGTCAGGAGCTGGCAGCTGTGCTACG
TGAGTCCTAGGTTCGGGGCTCTGATTTCCAAGTAGATATGAAATCCA
GGACTTGATGCCTAGGCTATCCATCCATCCATCTTAGTGGTAGAC
AAGGCTGTGTGAGAGGGGCTGTCCTCTGTGGAGTGTTCCTGGCCTAGGA
CAGGGGCTCTGGCTCTCTCCTGACTTCA
```

FIG.10E

```
AGTAGTTTGCCGGAYCGAAGTGGAAGAACARCATTCCCGTGAGCAGAACC
AAGGATGACGCATAAGAGGAGCTAGTTCTGGCAGGTAGAGACCCCAGGG
GCTCAGTTCTGCCCGTGTTAGGTTTAGAGGATGTGTTAGACTTCGG
AGTGGAGATGGTGGGAACTAGCTCTTCTTTATTCCGTCCCCCCAC
CTTCTCCAGTAGTAAATAGACGCCCAGGTGGCCAGTGTTGCGTTCTCT
TTCCCAGGAGACAAACGTCTTAGGCTTCAAGGVCCTCGGAAGATGAGCG
TGATTGTCCCAGGCCATGAACATGGTTCATGAGAGAGTCTCTATCCGCCCC
CGCAACGTGAGTGTCTACCCCCTTCCCTCCTTTCCCCATCATCCTAGT
CTCTGCATGAGCTTCTAAGGCAGAACTCCAGCTGTGTATATGTGGA
GGGGTACCATGTGAGAGAAAGCCCTGGAGGTCTAGGAAATCCAAGGACCCC
CATTCCCGGGATAGATCCCTTTCTGGGTGGTCATGGTGCCAAAGGCCTG
GGCCTGGCTCAGGTGAGGCTGAGCCTGCCCCTCCCCAGGAGCATGAGACTGCTAGC
ACGCTGGCAGAATAAGAACGGAGTGTATCATCGAGCTGCAAAACAAGA
CACCTGTCTGGAATGATGACACAGTCCTATGTACTACTTCAACTTCCATGGG
CGCGTCACAGGCCCTGTAAGAACTCCGTGAAGAACTCCAGATCATCATGGCAATGA
CCGTGAGTGTTTCTGTCCCCTACTCATTATGGTTCCGTAGGATACCCAAGGC
CCTTAGCGTAGGGTTCAGCCCACCTAGCCCTGCCTACACTGCCTAGAGTT
TAAGAATGTGAGCTATACACAGCTAAGGTTAGATGTATGGAACTTTCTAACC
```

FIG. 10F

```
CTAATGACTGGGAGTCCTGGAAGAACCTTCTTTGSAGCCCTGGTCCTAG
ATTCTGTGTATTCAACGGAGTCTCAGGCACGGGAACACCCTTTAAAGGA
CTTTCCTCTTTTCTGTCCCCTGGTGTTCACATGCATCTTACTTTGTCCT
TTGSCATCTGCCACCTCTTCCTGCCACTTCTCCCAATTGGCCTTTGTTT
TACTTCCCTTTGTGATTCCCCTGGCATCTCTGCTTCTCACTTGTTCTTCC
CTCATGTGGTTTGGGTGTCTGTCTATCCTTCCCTGGCTCTACCATTCCTG
TCCTGTCCTTTTCTCCTGTGCCTGTGGCCCCAGGACTACAT
CGTGATGCAGTTTGGCCTAGCAGGATGTTCACCATGATTACA
ACTACCCGCTGTGTCAGCCTTTGCCATTGCCCTGTCCAGCTTC
GACAGCAAGCTGGCCGTGCGAGTAGAGCCTCTTCGTGCCTTTGGGGTTG
CCCAGCCTGGAGCTTGCCTTCCCAGATGAAGCTTTGGCCCTGCCT
ATCCTCTGTATATAGGCCCCAGCCAGGAACTGGCTCCTTTGCCTCAGTGGG
CTCCCTGGCCAGCAGCAGAGCCTTTGCCTTTGCCTCTGCTACTGAG
GCAGGGGAGTAGTGGAGAGCGGGTGGGTGAAGGGATGAGAATAA
TTCTTTCCATGCCACGAGATCC
```

FIG.10G

FIG.12A

```
V   I   K   N   S   N   Q   K   G   K   A   K   G   K   K   K   A   K                                              20
GTG ATA AAG AAC AGC AAT CAA AAG GGC AAA GCC AAA GGA AAA AAG AAA GCG AAG                                             60

E   E   R   A   P   S   P   P   V   E   V   D   E   P   R   E   F   V   L   R                                      40
GAG GAG AGG GCC CCG TCT CCG CCC GTG GAG GTG GAC GAG CCC CGG GAG TTT GTG CTC CGG                                    120

P   A   P   Q   G   R   T   V   R   C   R   L   T   R   D   K   G   M   D                                          60
CCT GCC CCC CAG GGC CGG ACG GTG CGC TGC CGG CTG ACC CGG GAC AAA AAG GGC ATG GAT                                   180

R   G   M   Y   P   S   Y   F   L   H   L   D   T   E   K   K   V   F   L   L                                      80
CGA GGC ATG TAT CCC TCC TAC TTC CTG CAC CTG GAC ACG GAG AAG AAG GTG TTC CTC TTG                                   240

A   G   R   K   R   K   R   S   K   T   A   N   Y   L   I   S   I   D   P   T                                     100
GCT GGC AGG AAA CGA AGC AAG ACA GCC AAT TAC CTC ATC TCC ATC GAC CCT ACC                                           300

N   L   S   R   G   G   E   N   F   I   G   K   L   R   S   N   L   G   N                                         120
AAT CTG TCC CGA GGA GGG GAG AAT TTC ATC GGG AAG CTG AGG TCC AAC CTC GGG AAC                                       360

R   F   T   V   F   D   N   G   Q   N   P   Q   R   G   Y   S   T   N   V   A                                     140
CGC TTC ACG GTC TTT GAC AAC GGG CAG AAC CCA CAG CGT GGG TAC AGC ACT AAT GTG GCA                                   420
```

FIG.12B

```
  S   L   R   Q   E   L   A   A   V   I   Y   E   T   N   V   L   G   F   R   G        160
AGC CTT CGG CAG GAG CTG GCA GCT GTG ATC TAT GAA ACC AAC GTG CTG GGC TTC CGT GGC        480

P   R   R   M   T   V   I   I   P   G   M   S   A   E   N   E   R   V   P   I        180
CCC CGG CGC ATG ACC GTC ATC ATT CCT GGC ATG AGT GCG GAG AAC GAG AGG GTC CCC ATC        540

R   P   R   N   A   S   D   G   L   V   R   W   Q   N   K   T   L   E   S            200
CGG CCC CGA AAT GCT AGT GAC GGC CTG GTG CGC TGG CAG AAC AAG ACG CTG GAG AGC            600

L   I   E   L   H   N   K   P   P   V   W   N   D   D   S   G   Y   T   L            220
CTC ATA GAA CTG CAC AAC AAG CCA CCT GTC TGG AAC GAT GAC AGT GGC TAC ACC CTC            660

N   F   Q   G   R   V   T   Q   A   S   V   K   N   F   Q   I   V   H   A   D        240
AAC TTC CAA GGC CGG GTC ACC CAG GCC TCA GTC AAG AAC TTC CAG ATT GTC CAC GCT GAT        720

D   P   D   Y   I   V   L   Q   F   G   R   V   A   E   D   A   F   T   L   D        260
GAC CCC GAC TAT ATC GTG CTG CAG TTC GGC CGC GTG GCC GAG GAC GCC TTC ACC CTA GAC        780

Y   R   Y   P   L   C   A   L   Q   A   F   A   I   A   L   S   F   D   G            280
TAC CGG TAC CCG CTG TGC GCC CTG CAG GCC TTC GCC ATC GCC CTC TCC AGT TTC GAC GGG        840
```

```
                      K   L   A   C   E   *                                                          285
                      AAG CTG GCC TGC GAG TGA CCCCAGCAGCCCCTCAGCGCCCCAGAGCCCGTCAGGTGGG               900
                      GGAAAGGATTCAGTGGAGGCTGGCAGGGTCCCTCCAGCAAAGCTCCGCGGAAAACTGCT                   960
                      CCTGTGTCGGGGCTGACCTCCTCACTGCCTCCGCGTGACTCTCCGTCTCTCCCAGCCTGG                  1020
                      CACAGGCCGAGGCAGGAGGAGCCCGACGCGGGTAGGACGCGGGAGATGAAGAACATCTGA                  1080
                      GTTGGAGCCGGCACATCTGGTCTCGGAGCTGGCCGCGTGTGCCCCCTCCCCG                          1140
                      CGCCCCAGTCACTTCCTGTCCGGGAGCAGTAGTCATTGTTGTTTTAACCTCCCCTCTCCC                  1200
                      CGGGACCGGCTAGGGCTCCGAGGACCTGGGGGCTAGGAGGGGTAGGTGATGG                          1260
                      GGGACGAGGGCCAGGCACCCACATCCCAATAAAGCGGTCCTTGCAAAAAAAAA                         1320
                      AAAAAAAAAAAAAAAA                                                              1338

FIG. 12C
```

METHODS FOR IDENTIFYING COMPOUNDS THAT MODULATE MAMMALIAN TUB PROTEIN ACTIVITY

This application is a continuation-in-part of U.S. patent application Ser. No. 08/829,553, filed Mar. 28, 1997, issued as U.S. Pat. No. 5,817,762, which is a divisional of U.S. patent application Ser. No. 08/631,200, filed Apr. 12, 1996, issued as U.S. Pat. No. 5,646,040, issued Jul. 8, 1997. This application also claims the benefit of U.S. provisional application Ser. No. 60/000,604, filed Jun. 30, 1995, U.S. provisional application Ser. No. 60/001,273, filed Jul. 20, 1995, U.S. provisional application Ser. No. 60/001,444, filed Jul. 26, 1995, U.S. provisional application Ser. No. 60/002,759, filed Aug. 24, 1995, U.S. provisional application Ser. No. 60/004,424, filed Sep. 28, 1995, and U.S. provisional application Ser. No. 60/015,396, filed Apr. 9, 1996.

1. INTRODUCTION

The present invention relates to the mammalian tubby (tub) genes, including the human tub gene, which are novel genes involved in the control of mammalian body weight, including recombinant DNA molecules, cloned genes or degenerate variants thereof. The present invention further relates to novel mammalian, including human, tub gene products and to antibodies directed against such mammalian tub gene products, or conserved variants or fragments thereof. The present invention also includes cloning vectors containing mammalian tub gene molecules, and hosts which have been transformed with such molecules. In addition, the present invention presents methods for the diagnostic evaluation and prognosis of mammalian body weight disorders, including obesity, cachexia and anorexia, and for the identification of subjects exhibiting a predisposition to such conditions. Further, methods and compositions are presented for the treatment of mammalian body weight disorders, including obesity, cachexia and anorexia. Still further, the present invention relates to methods for the use of the Mammalian tub gene and/or mammalian tub gene products for the identification of compounds which modulate the expression of the mammalian tub gene and/or the activity of the mammalian tub gene products. In addition, the present invention relates to methods for the use of mammalian tub gene products for the identification of compounds which modulate the phosphorylated state or cellular localization of the mammalian tub gene products. Such compounds can be used as therapeutic agents in the treatment of mammalian body weight. disorders, including obesity, cachexia and anorexia.

2. BACKGROUND OF THE INVENTION

Obesity represents the most prevalent of body weight disorders, and it is the most important nutritional disorder in the western world, with estimates of its prevalence ranging from 30% to 50% within the middle-aged population. Other body weight disorders, such as anorexia nervosa and bulimia nervosa which together affect approximately 0.2% of the female population of the western world, also pose serious health threats. Further, such disorders as anorexia and cachexia (wasting) are also prominent features of other diseases such as cancer, cystic fibrosis, and AIDS.

Obesity, defined as an excess of body fat relative to lean body mass, also contributes to other diseases. For example, this disorder is responsible for increased incidences of diseases such as coronary artery disease, hypertension, stroke, diabetes, hyperlipidemia and some cancers. (See, e.g., Nishina, P. M. et al., 1994, Metab. 43:554–558; Grundy, S. M. & Barnett, J. P., 1990, Dis. Mon. 36:641–731) Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity (Friedman, J. M. et al., 1991, Mammalian Gene 1:130–144).

The epidemiology of obesity strongly shows that the disorder exhibits inherited characteristics (Stunkard, 1990, N. Eng. J. Med. 322:1483). Moll et al. have reported that, in many populations, obesity seems to be controlled by a few genetic loci (Moll et al. 1991, Am. J. Hum. Gen. 49:1243). In addition, human twin studies strongly suggest a substantial genetic basis in the control of body weight, with estimates of heritability of 80–90% (Simopoulos, A. P. & Childs. B., eds., 1989, in "Genetic Variation and Nutrition in Obesity", World Review of Nutrition and Diabetes 63, S. Karger, Basel, Switzerland; Borjeson, M., 1976, Acta. Paediatr. Scand. 65:279–287).

Studies of non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric, intake. In addition, it is a commonplace experience in animal husbandry that different strains of swine, cattle, etc., have different predispositions to obesity. Studies of the genetics of human obesity and of models of animal obesity demonstrate that obesity results from complex defective regulation of both food intake, food induced energy expenditure and of the balance between lipid and lean body anabolism.

There are a number of genetic diseases in man and other species which feature obesity among their more prominent symptoms, along with, frequently, dysmorphic features and mental retardation. For example, Prader-Willi syndrome (PWS; reviewed in Knoll, J. H. et al., 1993, Am. J. Med. Genet. 46:2–6) affects approximately 1 in 20,000 live births, and involves poor neonatal muscle tone, facial and genital deformities, and generally obesity.

In addition to PWS, many other pleiotropic syndromes which include obesity as a symptom have been characterized. These syndromes are more genetically straightforward, and appear to involve autosomal recessive alleles. The diseases, which include, among others, Ahlstroem, Carpenter, Bardet-Biedl, Cohen, and Morgagni-Stewart-Monel Syndromes.

A number of models exist for the study of obesity (see, e.g., Bray, G. A., 1992, Prog. Brain Res. 93:333–341, and Bray, G. A., 1989, Amer. J. Clin. Nutr. 5:891–902). For example, animals having mutations which lead to syndromes that include obesity symptoms have also been identified. Attempts have been made to utilize such animals as models for the study of obesity, and the best studied animal models, to date, for genetic obesity are mice. For reviews, see e.g., Friedman, J. M. et al., 1991, Mamm. Gen. 1:130–144; Friedman, J. M. and Liebel, R. L., 1992, Cell 69:217–220.)

Studies utilizing mice have confirmed that obesity is a very complex trait with a high degree of heritability. Mutations at a number of loci have been identified which lead to obese phenotypes. These include the autosomal recessive mutations obese (ob), diabetes (db), fat (fat) and tubby (tub). In addition, the autosomal dominant mutations Yellow at the agouti locus and Adipose (Ad) have been shown to contribute to an obese phenotype.

The ob and db mutations are on chromosomes 6 and 4 respectively, but lead to clinically similar pictures of obesity, evident starting at about one month of age, which include hyperphagia, severe abnormalities in glucose and insulin metabolism, very poor thermoregulation and non-shivering thermogenesis, and extreme torpor and underdevelopment of the lean body mass.

The ob gene and its human homologue have recently been cloned (Zhang, Y. et al., 1994, Nature 372:425–432). The gene appears to produce a 4.5 kb adipose tissue messenger RNA which contains a 167 amino acid open reading frame. The predicted amino acid sequence of the ob gene product indicates that it is a secreted protein and may, therefore, play a role as part of a signaling pathway from adipose tissue which may serve to regulate some aspect of body fat deposition.

The db locus encodes a high affinity receptor for the ob gene product (Chen, H. et al., Cell 84:491–495). The db gene product is a single membrane-spanning receptor most closely related to the gp130 cytokine receptor signal transducing component (Tartaglia, L. A. et al., 1995, Cell 83:1263–1271).

Homozygous mutations at either the fat or tub loci cause obesity which develops more slowly than that observed in ob and db mice (Coleman, D. L., and Eicher, E. M., 1990, J. Heredity 81:424–427), with tub obesity developing slower than that observed in fat animals. This feature of the tub obese phenotype makes the development of tub obese phenotype closest in resemblance to the manner in which obesity develops in humans. Even so, however, the obese phenotype within such animals can be characterized as massive in that animals eventually attain body weights which are nearly two times the average weight seen in normal mice. tub/tub mice develop insulin resistance with their weight gain but do not progress to overt diabetes.

In addition to obesity, retinal defects, hearing loss and infertility have all been observed in tub mice (Heckenlively, 1988, in Retinitis Pigmentosa, Heckenlively, ed., Lippincott, Philadelphia, pp. 221–235; Coleman, D. L. & Eicher, E. M., 1990, J. Hered. 81:424–427; Ohlemiller, K. K. et al., 1995, Neuroreport 6:845–849). Several human syndromes exist in which such defects are found to co-exist with an obesity phenotype, including Bardet-Biedl syndrome, Ahlstroem syndrome, polycystic ovarian disease and Usher's syndrome.

The fat mutation has been mapped to mouse chromosome 8, while the tub mutation has been mapped to mouse chromosome 7. According to Naggert et al., the fat mutation has recently been identified (Naggert, J. K., et al., 1995, Nature Genetics 10:135–141). Specifically, the fat mutation appears to be a mutation within the Cpe locus, which encodes the carboxypeptidase (Cpe) E protein. Cpe is an exopeptidase involved in the processing of prohormones, including proinsulin.

The dominant Yellow mutation at the agouti locus, causes a pleiotropic syndrome which causes moderate adult onset obesity, a yellow coat color, and a high incidence of tumor formation (Herberg, L. and Coleman, D. L., 1977, Metabolism 26:59), and an abnormal anatomic distribution of body fat (Coleman, D. L., 1978, Diabetologia 14:141–148). This mutation may represent the only known example of a pleiotropic mutation that causes an increase, rather than a decrease, in body size. The mutation causes the widespread expression of a protein which is normally seen only in neonatal skin (Michaud, E. J. et al., 1994, Genes Devel. 8:1463–1472).

Other animal models include fa/fa (fatty) rats, which bear many similarities to the ob/ob and db/db mice, discussed above. One difference is that, while fa/fa rats are very sensitive to cold, their capacity for non-shivering thermogenesis is normal. Torpor seems to play a larger part in the maintenance of obesity in fa/fa rats than in the mice mutants. In addition, inbred mouse strains such as NZO mice and Japanese KK mice are moderately obese. Certain hybrid mice, such as the Wellesley mouse, become spontaneously fat. Further, several desert rodents, such as the spiny mouse, do not become obese in their natural habitats, but do become so when fed on standard laboratory feed.

Animals which have been used as models for obesity have also been developed via physical or pharmacological methods. For example, bilateral lesions in the ventromedial hypothalamus (VMH) and ventrolateral hypothalamus (VLH) in the rat are associated, respectively, with hyperphagia and gross obesity and with aphagia, cachexia and anorexia. Further, it has been demonstrated that feeding monosodium-glutamate (MSG) or gold thioglucose to newborn mice also results in an obesity syndrome.

In summary, therefore, obesity, which poses a major, worldwide health problem, represents a complex, highly heritable trait. Given the severity, prevalence and potential heterogeneity of such disorders, there exists a great need for the identification of those genes that participate in the control of body weight.

It is an objective of the invention to provide modulators, such as intracellular modulators, of body weight, to provide methods for diagnosis of body weight disorders, to provide therapy for such disorders and to provide an assay system for the screening of substances which can be used to control body weight.

3. SUMMARY OF THE INVENTION

The present invention relates to the identification of novel nucleic acid molecules and proteins encoded by such nucleic acid molecules or degenerate variants thereof, that participate in the control of mammalian body weight. The nucleic acid molecules of the present invention represent the genes corresponding to the mammalian tub gene, including the human tub gene, which are involved in the regulation, control and/or modulation of body weight.

In particular, the compositions of the present invention include nucleic acid molecules (e.g., tub gene), including recombinant DNA molecules, cloned genes or degenerate variants thereof, especially naturally occurring variants, which encode novel tub gene products, and antibodies directed against such tub gene products or conserved variants or fragments thereof. The compositions of the present invention additionally include cloning vectors, including expression vectors, containing the nucleic acid molecules of the invention and hosts which have been transformed with such nucleic acid molecules.

Nucleic acid sequences of a wild type and a mutant form of the murine tub gene are provided. The wild type murine tub gene produces a full length transcript of approximately 7.0 kb and encodes a protein of 505 amino acids, the sequence of which is provided. The amino acid sequence of the predicted full length tub gene product does not contain either a recognizable transmembrane domain or a signal sequence, suggesting that the tub gene product is an intracellular gene product. In situ results revealed tub gene expression throughout neuronal-derived tissues in mice, including heart ganglion region, adrenal medulla, gangliar layer of olfactory epithelium and enteric nervous system. The mammalian tub gene is, as shown herein, expressed in the brain, including the hypothalamus.

Nucleic acid sequences of a wild type human tub gene are also provided. The human tub gene encodes a full length protein of 505 amino acids, the sequence of which is provided. The human tub gene and gene product are strikingly similar to the murine tub gene and gene product. Specifically, the human tub gene is, at the nucleotide level, 89% identical to the murine tub gene. Further, the amino acid sequence of the human tub gene product is 94% identical to the amino acid sequence of the murine tub gene product.

Both murine and human tub genes produce transcripts which undergo alternative splicing. Such alternative splicing yields, in addition to the full length transcripts, transcripts which lack sequences corresponding to tub exon 5. Nucleic acid sequences corresponding to such alternatively spliced transcripts and the tub gene products encoded by such alternatively spliced transcripts are provided herein.

In addition, this invention presents methods for the diagnostic evaluation and prognosis of body weight disorders, including obesity, cachexia and anorexia, and for the identification of subjects having a predisposition to such conditions. For example, nucleic acid molecules of the invention can be used as diagnostic hybridization probes or as primers for diagnostic PCR analysis for the identification of tub gene mutations, allelic variations and regulatory defects in the tub gene, and of alternatively spliced transcripts produced by the tub gene. For example, human tub genomic sequences are provided which can be used to selectively amplify human tub exons for analysis.

Further, methods and compositions are presented for the treatment of body weight disorders, including obesity, cachexia and anorexia. Such methods and compositions are capable of modulating the level of tub gene expression and/or the level of tub gene product activity. Such methods and compositions can also be utilized in the treatment or amelioration of symptoms of tub gene-related sensory defects (e.g., eye and hearing) and fertility defects.

Still further, the present invention relates to methods for the use of the tub gene and/or tub gene products for the identification of compounds which modulate tub gene expression and/or the activity of tub gene products. Such compounds can be used as agents to control body weight and, in particular, therapeutic agents in the treatment of body weight and body weight disorders, including obesity, cachexia and anorexia. Such methods and compositions can also be utilized in the treatment or amelioration of symptoms of tub gene-related sensory (e.g., eye and hearing) and fertility defects. It is further contemplated that the nucleic acid molecules, peptides and other compounds of the invention can have agricultural applications. For example, the ratio of fat to lean tissue of agricultural animals can be favorably altered, e.g., this ratio can be decreased.

In particular, the present invention relates to methods for the use of tub gene products for the identification of compounds which modulate tub gene product activity for example by altering the tyrosine phosphorylated state of the tub gene product. The present invention further relates to methods for the use of tub gene products for the identification of compounds which modulate the cellular localization of the tub gene product and its interaction with other cellular proteins and peptides. The methods of the present invention may be applied to high throughput screening assays for the rapid identification of compounds which can be used as agents to control body weight and in particular, therapeutic agents for the treatment of body weight disorders, including obesity, cachexia and anorexia.

This invention is based, in part, on the genetic and physical mapping of the tub gene to a specific portion of mouse chromosome 7, described in the Examples presented, below, in Section 6 and 7. The invention is further based, in part, on the expression and sequence analysis of a candidate tub gene using nucleic acid derived from wild type and tub homozygous animals, which proves that this candidate gene does, indeed, represent the tub gene. Such analyses are described in the Examples presented, below, in Sections 8–12, and include the identification of a splice site mutation in nucleic acid derived from tubby animals which is absent from the corresponding nucleic acid derived from wild type, non-obese animals. This single base mutation consists of a guanine (G) to a thymidine (T) in the splice site recognition sequence, which results in the retention of an intronic sequence in the mature tub mRNA that encodes an abnormal, loss-of-function, tub gene product. Further, Section 13 presents the successful cloning of the human tub gene homologue.

Still further, the Example presented in Section 14 demonstrates that both the murine and human tub transcripts undergo alternative splicing. Section 15 demonstrates the successful expression of recombinant human and murine tub gene products. The Example presented in Section 16 describes the identification, cloning and characterization of a human tub homolog. Section 17 demonstrates that the mammalian tub gene product's subcellular localization and tyrosine phosphorylated state varies in response to insulin stimulation.

3.1. Abbreviations

As used herein, the abbreviations for the various forms of the tub gene product are as follows:

"HA-tub", as used herein, refers to the gene product corresponding to flu hemagglutinin (HA) epitopes (YPYDVPDYA) (SEQ ID NO:60) in frame with the amino terminal of the wild-type tub gene.

"GFP-tub", as used herein, refers to the gene product corresponding to the green fluorescent protein (GFP) in frame with the amino terminal of the wild type tub gene.

"Mut-tub", as used herein, refers to the gene product corresponding to flu HA epitopes or GFP in frame with the amino terminal of the mutant tub gene.

"Y3/F-tub", as used herein, refers to the gene product corresponding to flu HA epitopes or GFP in frame with the amino terminal of a mutant form of the tub gene, in which phenylalamine residues replaced tyrosine residues at positions 483, 481 and 464.

"C/S-tub", as used herein, refers to the gene product corresponding to flu HA epitopes or GFP in frame with the amino terminal of a mutant form of the tub gene, in which a serine residue has replaced the cysteine residue at position 504.

4. DESCRIPTION OF THE FIGURES

FIG. 1. Physical map of the D7Mit17 to D7Mit53 interval of mouse chromosome 7.

Figure 2:
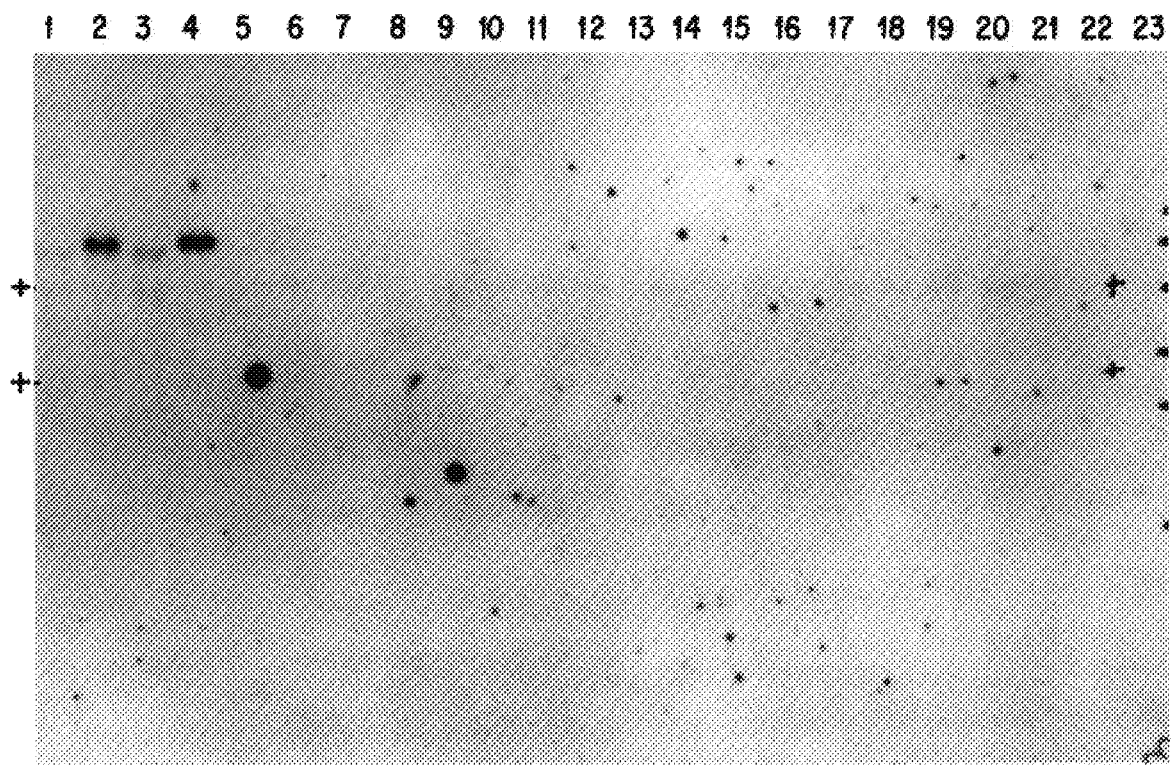

FIG. 2. Northern blot analysis of total RNA derived from various tissues of tub and wild type (C57BL/6J) mice, using the 90 bp P8X1 DNA fragment as a probe. See Sections 10.1 and 10.2 for details.

Figure 3:
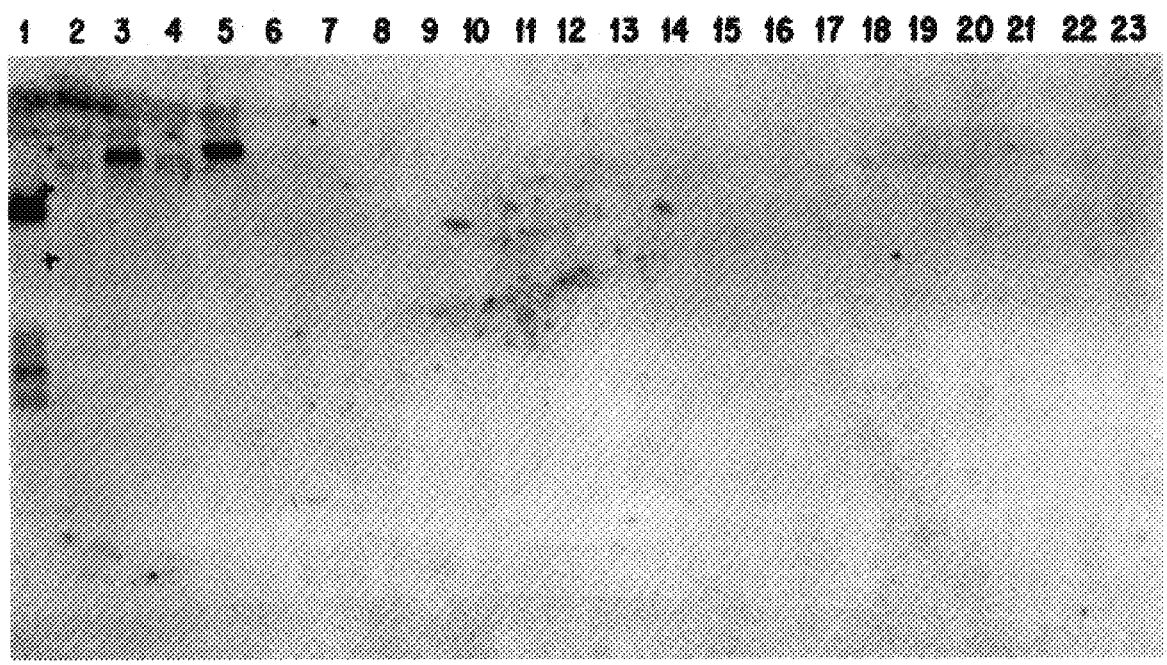

FIG. 3. Northern blot analysis of total RNA derived from various tissues of tub and wild type (C57BL/6J) mice, using the 1.15 kb fume009 cDNA clone as a probe. See Sections 9.1 and 9.2 for details.

Figure 4:
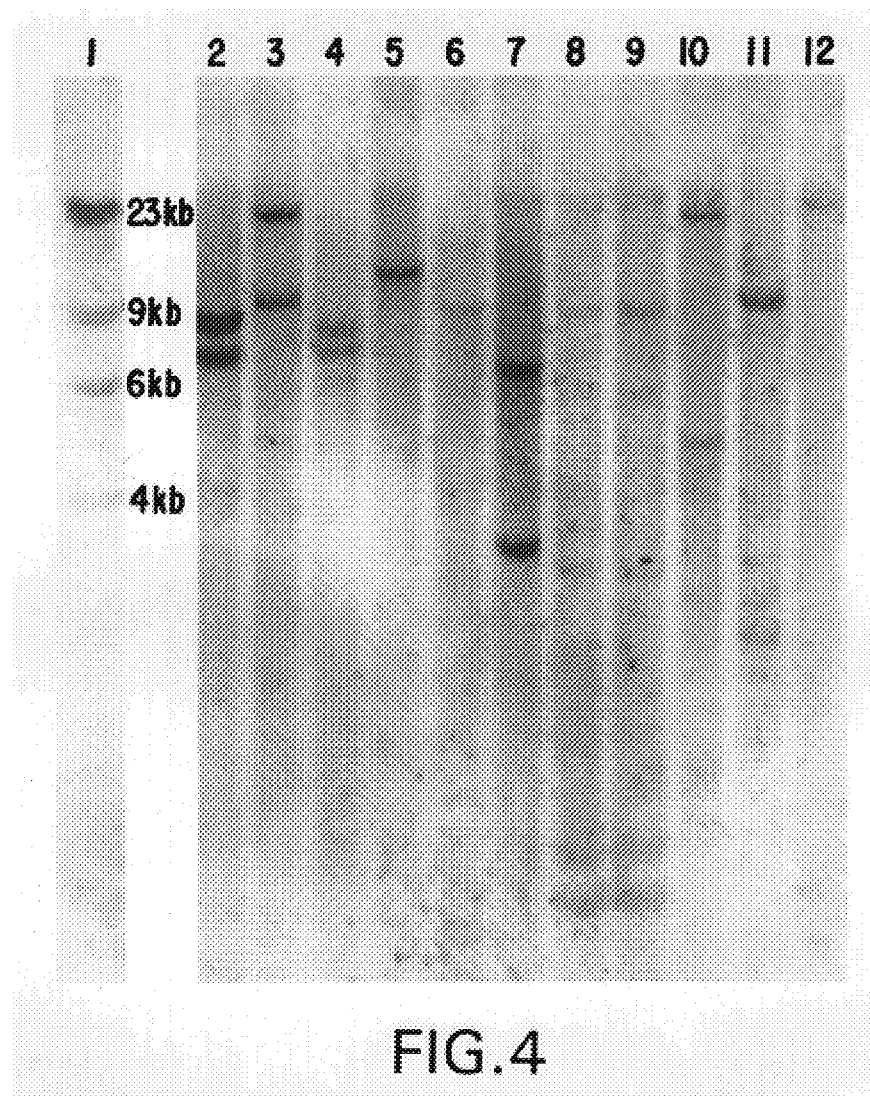

FIG. 4. Southern blot analysis of EcoRI-digested mammalian genomic DNA derived from a number of different species, as indicated, using a fragment of CBT9 (P8X9-10) as a probe, as described, below, in Sections 10.1 and 10.2.

Figure 5:
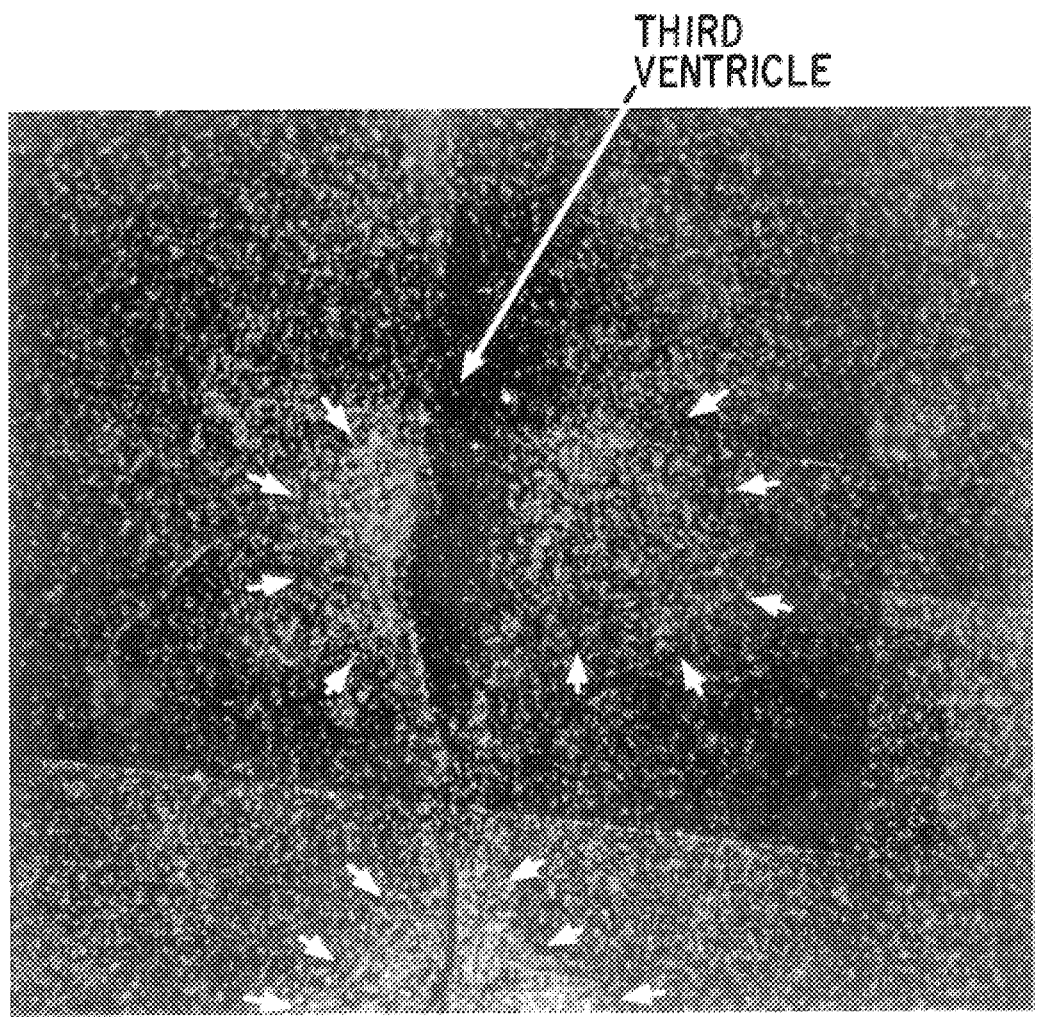

FIG. 5. In situ hybridization analysis of CBT9 spatial expression in a brain (hypothalamus) tissue section of C57BL/6J wild type mice, using a fume009 cDNA probe.

FIGS. 6A–6D. Nucleotide sequence of the coding region (and portions of 5' and 3' untranslated regions) of the wild type tub gene (bottom line) (SEQ ID NO:1) and the encoded amino acid sequence (top line) (SEQ ID NO:2).

FIGS. 7A–7D. Alignment of cDNA and genomic sequences derived from wild type C57BL/6J (genomic= SEQ ID NO:4; cDNA=SEQ ID NO:6) and tub RNA (genomic=SEQ ID NO:3; cDNA SEQ ID NO:5) in the region of the splice site mutation. See Section 12.1 and 12.2 for details.

Figure 8:
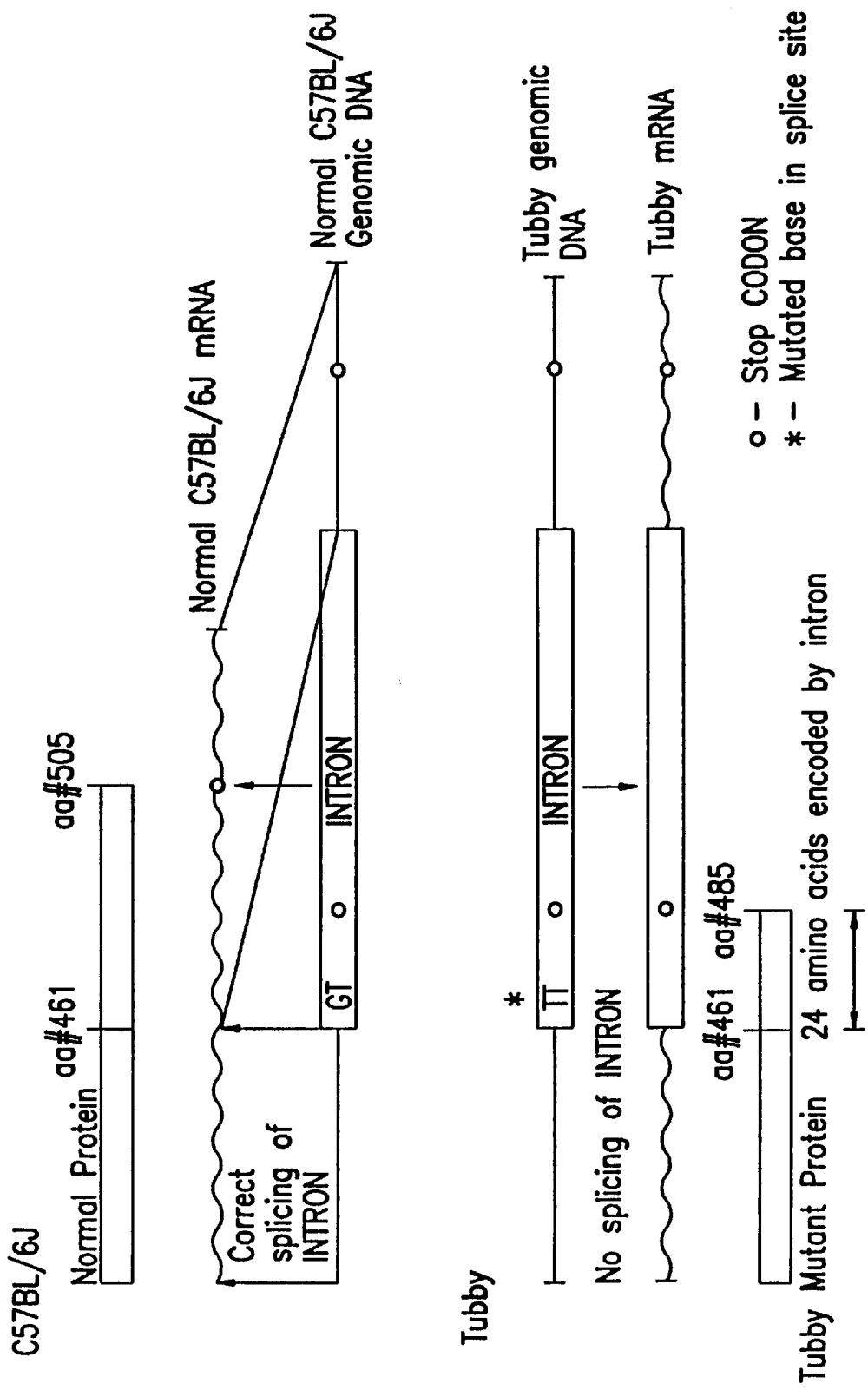

FIG. 8. Schematic representation of the splicing defect in the CBT9 gene in tub animals.

FIGS. 9A–9D. Nucleotide sequence of the coding region (and portions of 5' and 3' untranslated regions) of the human tub gene (bottom line) (SEQ ID NO:7) and the encoded human tub gene product amino acid sequence (top line) (SEQ ID NO:8).

FIGS. 10A–10G (SEQ ID NO:9–13). Human tub genomic sequence. Depicted here-in are human tub gene exons 4–12 nucleotide sequences and flanking intronic sequences. Intron boundaries are depicted in bold; exon sequences are underlined. 10A. Exon 4 (corresponding to nucleotide sequence 254–397 of FIGS. 9A–9D) and its flanking genomic sequence. 10B. Exon 5 (corresponding to nucleotide sequence 398–565 of FIGS. 9A–9D) and its flanking genomic sequence. FIGS. 10C–10D. Exons 6–8 (corresponding to nucleotide sequences 566–687, 688–885, and 886–998 of FIGS. 9A–9D, respectively) and its flanking genomic sequence. 10E. Exon 9 (corresponding to nucleotide sequence 999–1116 of FIGS. 9A–9D) and its flanking genomic sequence. FIGS. 10F–10G. Exons 10–12 (corresponding to nucleotide sequences 1117–1215, 1216–1387 and 1388–1729 of FIGS. 9A–9D, respectively) and its flanking genomic sequence.

Figure 11:
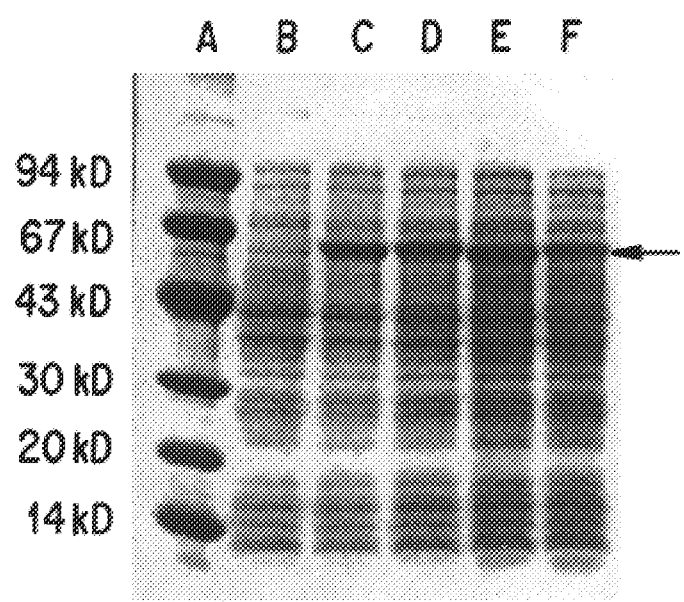

FIG. 11. SDS polyacrylamide protein gel demonstrating bacterial expression of recombinant murine and human tub gene products. Lanes from left to right: Pharmacia Low Molecular Weight Markers; uninduced BL21DE3/human pET29*-tub; induced BL21DE3/human pET29*-tub; induced BL21DE3/human pET29*-tub $HIS_6$; induced BL21DE3/murine pET29*-tub; induced BL21DE3/murine pET29*-tub $HIS_6$. Arrow represents recombinant tub gene products.

FIGS. 12A–12C. Nucleotide and amino acid sequence of the human tub homolog 1 gene. Top line: amino acid sequence (SEQ ID NO:15). Bottom Line: nucleotide sequence (SEQ ID NO:14). "*" represents the stop codon.

Figure 13A:
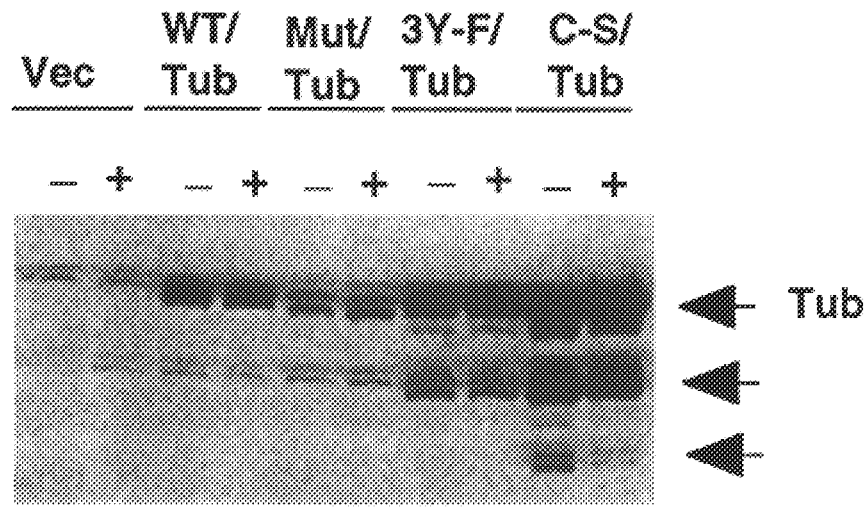
Figure 13B:
Figure 13C:
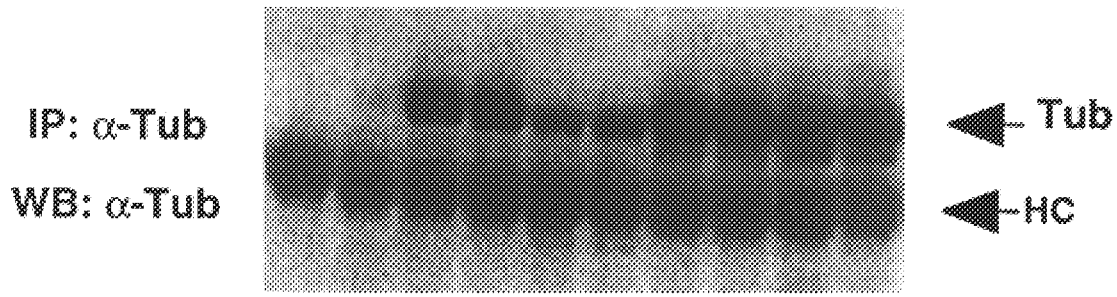

FIGS. 13A–13C. (A) anti-phosphotyrosine (phosphotyrosine) immunoblot of anti-phosphotyrosine immunoprecipitates and (B and C) anti-tub (polyclonal, rabbit) immunoblot analysis of anti-phosphotyrosine immunoprecipitates and whole call lysate obtained from 3T3 cells, transiently expressing HA-tagged WT-tub (HA-tub), stimulated with insulin (100 nM), IGF-1 (100 nM) and PDGF (20 ng/ml). Shows that HA-tub is phosphorylated on tyrosine residues in response to insulin and IGF-1 but not PDGF.

Figure 14A:
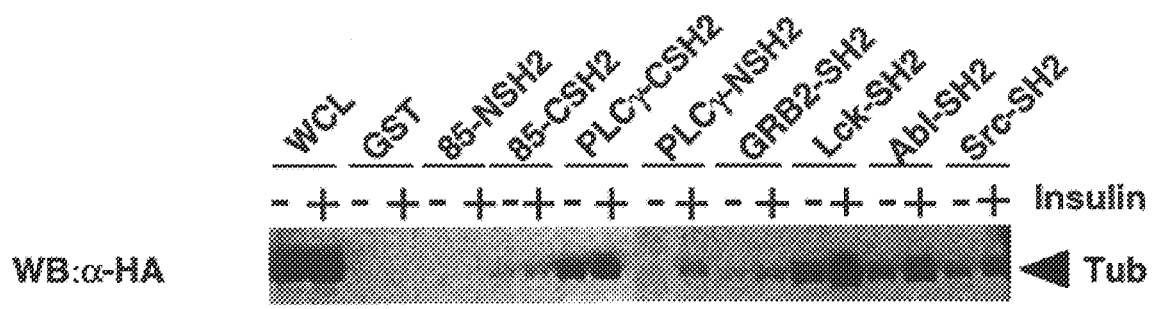
Figure 14B:
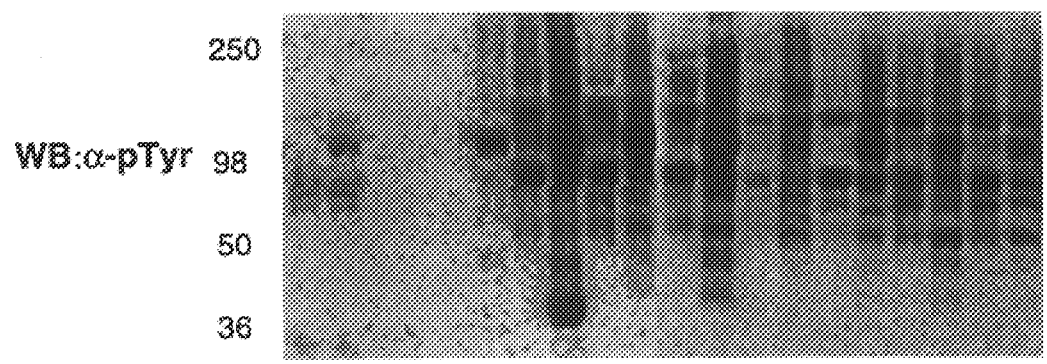

FIGS. 14A–14B. (A) Anti-HA western blot analysis to determine the interaction of HA-tub gene product expressed in CHO-IR cells, treated or not with insulin, with the following SH2 domains: 85-aminoSH2, 85-carboxySH2, PLC gamona-aminoSH2, PLCγ-carboxySH2, GRB2-SH2, LCK-SH2, ABL-SH2, Src-SH2. (A) Anti-ptyr Western blot analysis of SH2-bound proteins to demonstrate that all SH2 domains pulled down phosphotyrosine containing peptides.

Figure 15A:
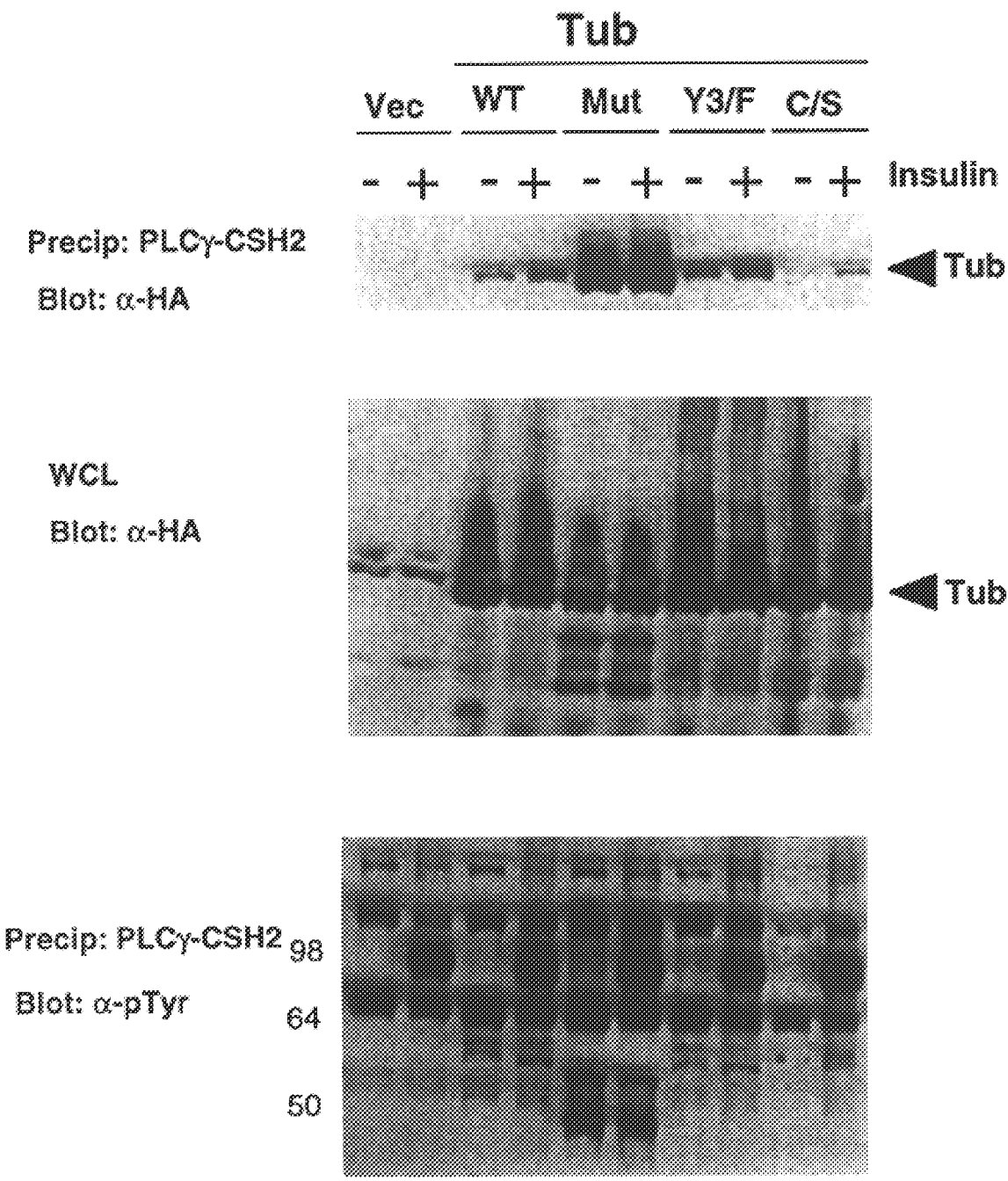
Figure 15B:
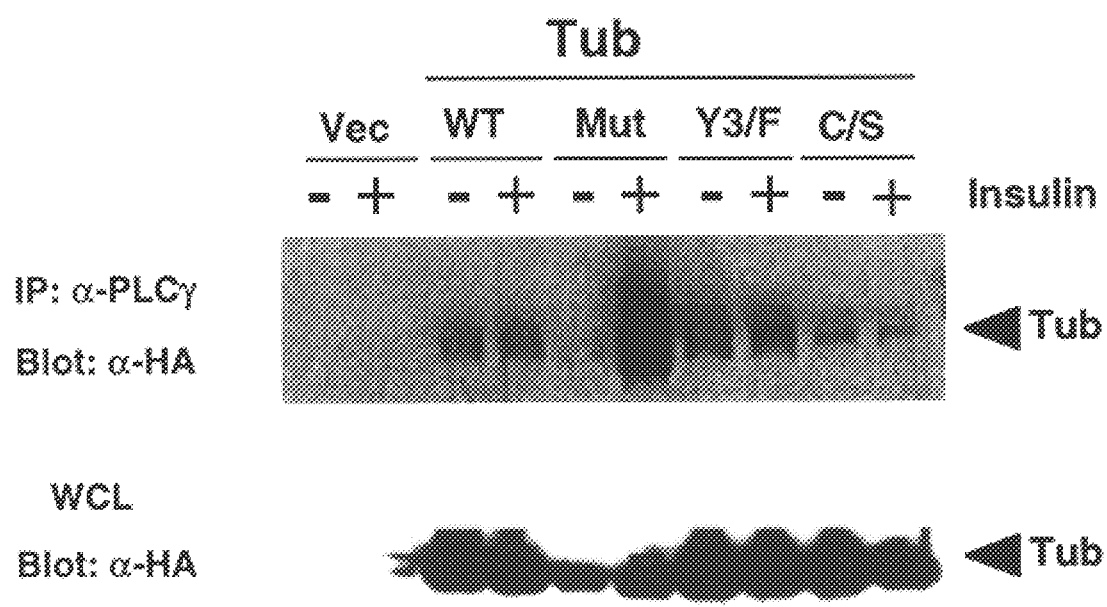

FIGS. 15A–15B. (A) Lysates from insulin treated or control CHO-IR cells expressing HA-tub, Mut-tub, Y3/F-tub and C/S-tub were incubated with PLCγ-carboxySH2 domain immobilized onto GSH beads. Precipitates were resolved by SDS-PAGE and probed with α-HA and α-phosphotyrosine antibodies, respectively to detect tub gene product and phosphotyrosine-containing proteins. (B) Lysates were incubated instead with an α-PLC antibody to test whether transiently expressed HA-tub, Mut-tub, Y3/F-tub and C/S-tub, associate with endogenous PLC gamma.

5. DETAILED DESCRIPTION OF THE INVENTION

Described herein are the identification of the novel mammalian tubby (tub) genes, including the human tub gene, which are involved in the control of mammalian body weight. Also described are recombinant mammalian, including human, tub DNA molecules, cloned genes, or degenerate variants thereof. The compositions of the present invention further include tub gene products (e.g., proteins) that are encoded by the tub gene, and the modulation of tub gene expression and/or tub gene product activity in the treatment of mammalian body weight, and body weight disorders, including obesity, cachexia and anorexia. Also described herein are antibodies against tub gene products (e.g., proteins), or conserved variants or fragments thereof, and nucleic acid probes useful for the identification of tub gene mutations and the use of such nucleic acid probes in diagnosing mammalian body weight disorders, including obesity, cachexia and anorexia. Further described are methods for the use of the tub gene and/or tub gene products in the identification of compounds which modulate the activity of the tub gene product: In addition, screening assays are described herein for the identification of compounds which modulate the phosphorylated state and the subcellular localization of the tub gene product.

The murine tub nucleic acid compositions of the invention are demonstrated in the Examples presented, below, in Sections 6 through 12. The human tub nucleic acid compositions of the invention are demonstrated in Section 13, below. For clarity, it should be noted that the murine tub gene is also referred to herein as the CBT9 gene, and was identified and cloned as follows. Genetic and physical mapping of the murine tub gene interval was narrowed to the interval between markers D7Mit39 and D7Mit53. A P1 genomic clone, P8, was located within this interval, as indicated in FIG. 1. A P8 subclone, designated ium008p004, was sequenced. An analysis of ium008p004 indicated that this sequence was part of the coding region of a gene. A 90 bp fragment, designated P8X1, was amplified from this ium008p004 subclone. P8X1 was used as a probe to screen a mouse brain cDNA library, resulting in the identification of a 1.15 kb cDNA clone, designated fume009. Fume009 was used as a probe to screen a mouse hypothalamus cDNA library, resulting in the identification of a 6.0 kb cDNA clone, designated fumh019. To summarize, therefore, ium008p004, PX81, fume009 and fumh019 are all part of the murine tub gene, which is also referred to herein as the CBT9 gene.

5.1. THE tub GENE

The murine tub gene, shown in FIGS. 6A–6D, and the human tub gene, shown in FIGS. 9A–9D, are novel genes involved in the control of body weight. Nucleic acid sequences of the identified tub gene are described herein. As used herein, "tub gene" refers to (a) a gene containing the DNA sequence shown in FIGS. 6A–6D or FIGS. 9A–9D or contained in the cDNA clone fumh019, CBT9H1 or CBT9H3, or genomic clone P6, P8, or B13, as deposited with the American Type Culture Collection (ATCC); (b) any DNA sequence that encodes the amino acid sequence shown in FIGS. 6A–6D or FIGS. 9A–9D, or encodes the amino acid sequence shown in FIGS. 6A–6D or FIGS. 9A–9D but lacking the amino acid residues encoded by tub exon 5 (i.e., amino acid residues 134–189 to 134–189 of FIGS. 6A–6D or FIGS. 9A–9D), or encoded by the cDNA clone fumh019, CBT9H1 or CBT9H3, or genomic clone P6, P8, or B13, as deposited with the ATCC; (c) any DNA sequence that hybridizes to the complement of the DNA sequences that encode the amino acid sequence shown in FIGS. 6A–6D or FIGS. 9A–9D, or encodes the amino acid sequence shown in FIGS. 6A–6D or FIGS. 9A–9D but lacking the amino acid residues encoded by tub exon 5 (i.e., amino acid residues 134 to 189 of FIGS. 6A–6D or FIGS. 9A–9D), or contained in the cDNA clone fumh019, CBT9H1 or CBT9H3, or genomic clone P6, P8, or B13, as deposited with the ATCC, under highly stringent conditions, e.g., hybridization to filter-bound DNA in 0.5M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a gene product functionally equivalent to a tub gene product encoded by sequences contained within the cDNA clone fumh019, CBT9H1 or CBT9H3, sequences shown in FIGS. 6A–6D or FIGS. 9A–9D, sequences shown in FIGS. 6A–6D or FIGS. 9A–9D, but lacking tub exon 5, or genomic clone P6, P8, or B13; and/or (d) any DNA sequence that hybridizes to the complement of the DNA sequences that encode the amino acid sequence shown in FIGS. 6A–6D or FIGS. 9A–9D, or encode the amino acid sequence shown in FIGS. 6A–6D or FIGS. 9A–9D but lacking the amino acid residues; encoded by tub exon 5 (i.e., amino acid residues 134 to 189 of FIGS. 6A–6D or FIGS. 9A–9D), contained in the cDNA clone fumh019, CBT9H1 or CBT9H3, or genomic clone P6, P8, or B13, as deposited with the ATCC, under less stringent conditions, such as moderately stringent conditions, e.g., washing in 0.2×SSC/0.1% SDS at 42° C. (Ausubel et al., 1989, supra), yet which still encodes a functionally equivalent tub gene product. As used herein, tub gene may also refer to degenerate variants of DNA sequences (a) through (d), especially naturally occurring variants thereof.

The invention also includes nucleic acid molecules, preferably DNA molecules, that hybridize to, and are therefore the complements of, the DNA sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as tub gene antisense molecules, useful, for example, in tub gene regulation (for and/or as antisense primers in amplification reactions of tub gene nucleic acid sequences. With respect to tub gene regulation, such techniques can be used to regulate, for example, cachexia and/or anorexia. Further, such sequences may be used as part of ribozyme and/or triple helix sequences, also useful for tub gene regulation. Still further, such molecules may be used as components of diagnostic methods whereby, for example, the presence of a particular tub allele or alternatively spliced tub transcript responsible for causing or predisposing one to a weight disorder, such as obesity, may be detected. Among the molecules which can be used for diagnostic methods such as these which involve amplification of genomic tub sequences are those listed in FIGS. 10–10G and in Table I, below.

The invention also encompasses (a) DNA vectors that contain any of the foregoing tub coding sequences and/or their complements (i.e., antisense); (b) DNA expression vectors that contain any of the foregoing tub coding sequences operatively associated with a regulatory element that directs the expression of the coding sequences; and (c) genetically engineered host cells that contain any of the foregoing tub coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors. The invention includes fragments of any of the DNA sequences disclosed herein.

In addition to the tub gene sequences described above, homologs of such sequences, exhibiting extensive homology to one or more of domains of the tub gene product present in other species can be identified and readily isolated, without undue experimentation, by molecular biological techniques well known in the art. Further, there can exist homolog genes at other genetic loci within the genome that encode protein, which have extensive homology to one or more domains of the tub gene product. These genes can also be identified via similar techniques.

As an example, in order to clone a human tub gene homologue using isolated murine tub gene sequences as disclosed herein, such murine tub gene sequences may be labeled and used to screen a cDNA library constructed from mRNA obtained from appropriate cells or tissues (e.g., preferably hypothalamus, or brain) derived from the organism (in this case, human) of interest. With respect to the cloning of such a human tub homologue, a human fetal brain cDNA library (e.g., Clontech #HL1149x) may, for example, be used for screening.

The hybridization washing conditions used should be of a lower stringency when the cDNA library is derived from an organism different from the type of organism from which the labeled sequence was derived. With respect to the cloning of a human tub homologue, for example, hybridization can be performed for 4 hours at 65° C. using Amersham Rapid Hyb™ buffer (Cat. #RPN1639) according to manufacturer's protocol, followed by washing, with a final washing stringency of 1.0×SSC/0.1% SDS at 50° C. for 20 minutes being preferred.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled fragment may be used to screen a genomic library derived from the organism of interest, again, using appropriately stringent conditions.

Further, a tub gene homologue may be isolated from nucleic acid of the organism of interest by performing PCR using two degenerate oligonucleotide primer pools designed on the basis of amino acid sequences within the tub gene product disclosed herein. The template for the reaction may be cDNA obtained by reverse transcription of mRNA prepared from, for example, human or non-human cell lines or tissue known or suspected to express a tub gene allele.

The PCR product may be subcloned and sequenced to ensure that the amplified sequences represent the sequences of a tub gene nucleic acid sequence. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

Taking, as an example, the cloning of a human tub homologue using murine tub nucleic acid sequences, among the murine tub primers which may be utilized for PCR amplification are, for example, the following, which are derived from the murine fumh019 sequence described, above:

5'-CCG ACT CGA TTG CCA GTG TA-3' (SEQ ID NO:16)

5'-GCG GAT ACA GAC TCT CTC AT-3' (SEQ ID NO:17)

These primers generate a cDNA product of approximately 950 base pairs which can then be used as probe for the screening of appropriate cDNA libraries such as, for example, human fetal train cDNA libraries (e.g., Clontech #HL1149x). When a cDNA library is screened with probes such as this, hybridization can, for example, be performed for 4 hours at 65° C. using Amersham Rapid Hyb™ buffer (Cat. #RPN1639) according to manufacturer's protocol, followed by washing, with a final washing stringency of 1.0×SSC/0.1% SDS at 50° C. for 20 minutes being preferred.

The Example presented in Section 16, below, describes the successful identification, cloning and characterization of a human tub homolog.

PCR technology may also be utilized to isolate full length cDNA sequences. For example, RNA may be isolated, following standard procedures, from an appropriate cellular or tissue source (i.e., one known, or suspected, to express the tub gene, such as, for example, hypothalamus tissue). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

tub gene sequences may additionally be used to isolate mutant tub gene alleles. Such mutant alleles may be isolated from individuals either known or proposed to have a genotype which contributes to the symptoms of body weight disorders such as obesity, cachexia or anorexia. Mutant alleles and mutant allele products may then be utilized in the therapeutic and diagnostic systems described below. Additionally, such tub gene sequences can be used to detect tub gene regulatory (e.g., promoter) defects which can affect body weight.

A cDNA of a mutant tub gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant tub allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant tub allele to that of the normal tub allele, the mutation(s) responsible for the loss or alteration of function of the mutant tub gene product can be ascertained.

Alternatively, a genomic library can be constructed using DNA obtained from an individual suspected of or known to carry the mutant tub allele, or a cDNA library can be constructed using RNA from a tissue known, or suspected, to express the mutant tub allele. The normal tub gene or any suitable fragment thereof may then be labeled and used as a probe to identify the corresponding mutant tub allele in such libraries. Clones containing the mutant tub gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant tub allele in an individual suspected of or known to carry such a mutant allele. In this manner, gene products made by the putatively mutant tissue may be expressed and screened using standard antibody screening techniques in conjunction with antibodies raised against the normal tub gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In cases where a tub mutation results in an expressed gene product with altered function (e.g., as a result of a missense or a frameshift mutation), a polyclonal set of anti-tub gene product antibodies are likely to crossreact with the mutant tub gene product. Library clones detected via their reaction with such labeled antibodies can be purified and subjected to sequence analysis according to methods well known to those of skill in the art.

5.2. Protein Products of the Tub Gene tub gene products, or peptide fragments thereof, can be prepared for a variety of uses. For example, such gene products, or peptide fragments thereof, can be used for the generation of antibodies, in diagnostic assays, or for the identification of other cellular gene products involved in the regulation of body weight.

The amino acid sequence depicted in FIGS. 6A–6D represents a murine tub gene product, while the amino acid sequence depicted in FIGS. 9A–9D represents a human tub gene product. The tub gene product, sometimes referred to herein as a "tub protein", may additionally include those gene products encoded by the tub gene sequences described in Section 5.1, above, and is intended to include, for example, a tub gene product encoded by a tub gene sequence lacking tub exon 5.

The tub gene product of the present invention also encompasses peptides corresponding to one or more domains of the tub gene product (e.g. nuclear localization sequence, NLS: amino acids. 301 to 307, amino acid sequence: RKRKKSK (SEQ ID NO:61); tyrosine phosphorylation sites/SH-2 docking sequences, amino acids 10 to 17, amino acid sequence: IPYSVLDD (SEQ ID NO:62); amino acids 72 to 79, amino acid sequence: ESYLSSSG (SEQ ID NO:63); amino acids 81 to 88, amino acid sequence: TSYQVQEA (SEQ ID NO:64); amino acids 278 to 285, amino acid sequence: GMYPTYFL (SEQ ID NO:65); amino acids 281 to 288, amino acid sequence: PTYFLHLD (SEQ ID NO:66); amino acids 309 to 316, amino acid sequence: SNYLISVF (SEQ ID NO:67); amino acids 325 to 332, amino acid sequence: DSYIGKLR (SEQ ID NO:68); amino acids 341 to 348, amino acid sequence: TVYDNGYN (SEQ ID NO:69); amino acids 369 to 376, amino acid sequence: VCYETNVL (SEQ ID NO:70) ; amino acids 436 to 443, amino acid sequence: QSYVLNFH (SEQ ID NO:71); amino acids 462–469, amino acid sequence: MDYNYPLC (SEQ ID NO:72); and amino acids 481–488, amino acid sequence: YNYPLCAL (SEQ ID NO:73); putative lipid acceptor sites (prenylation/palmitylation): amino acids 501 to 505, amino acid sequence: KLACE (SEQ ID NO:81); dibasic proteolytic cleavage sites: amino acids 300 to 305, amino acid sequence: GRKRKK (SEQ ID NO:74) and amino acids 380 to 383, amino acid sequence: GPRK (SEQ ID NO:75), truncated or deleted tub gene products as well as fusion protein in which the full length tub gene product, a tub peptide or truncated tub is fused to an unrelated protein are also within the scope of the invention and can be designed on the basis of the tub nucleotide and tub amino acid sequences disclosed in this section and in Section 5.1, above. Such fusion proteins include, but are not limited to, fusions to any amino acid sequence that contain the tyrosine phosphorylation sites, SH-2 docking sequences or the NLS of the tub gene product. In a preferred embodiment, tub gene products are expressed as a fusion protein with green fluorescent protein (GFP).

In addition, tub gene products may include proteins that represent functionally equivalent gene products. The tub gene product also encompasses peptides corresponding to one or more domains of the tub gene product peptides in which domains of the tub gene product have been replaced or mutated, in particular, peptides in which the nuclear localization sequence, the lipid acceptor sites, the serine/threonine residues, the tyrosine residues or the proteolytic cleavage sites have been mutated or replaced. Such an equivalent tub gene product may contain deletions, truncations, additions or substitutions of amino acid residues within the amino acid sequence encoded by the tub gene sequences described, above, in Section 5.1, but which result in a silent change, thus producing a functionally equivalent tub gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

In accordance with the present invention, alterations can be engineered in order to produce a mutant tub gene product that has an altered subcellular localization. For example, the nuclear localization signal or the carboxy terminal cysteine may be altered so that the tub gene product is retained in the cytoplasm or in the nucleus, respectively. Alternatively, where alteration of function is desired, deletion or substitution of tyrosine residues may be engineered. Further, alterations of the SH-2 docking domains, i.e. deletions or substitutions to produce a mutant tub gene product that migrates from the nucleus but is signaling-incompetent. Alterations to the residues of the SH-2 docking domains can be engineered to produce mutant tub gene products with altered binding affinities for proteins containing SH-2 domains.

"Functionally equivalent", as utilized herein, refers to a protein capable of exhibiting a substantially similar in vivo activity as the endogenous tub gene products encoded by the tub gene sequences described in Section 5.1, above. The in vivo activity of the tub gene product, as used herein, refers to the ability of the tub gene product, when present in an appropriate cell type, to ameliorate, prevent or delay the appearance of the obese phenotype relative to it appearance when that cell type lacks a functional tub gene product. "Obese phenotype", as used herein, refers to the well known tub phenotype, db phenotype, or ob phenotype. In humans, this can also refer to an increased percentage of body fat which is medically considered abnormal.

The tub gene products or peptide fragments thereof, may be produced by recombinant DNA technology using techniques well known in the art. Thus, methods for preparing the tub gene polypeptides and peptides of the invention by expressing nucleic acid containing tub gene sequences are described herein. Methods which are well known to those skilled in the art can be used to construct expression vectors containing tub gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding tub gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the tub gene coding sequences of the invention. Such host-expression systems represent vehicles by which the coding sequences of interest may be produced and subsequently purified, but also represent cells which may, when transformed or transfected with the appropriate nucleotide coding sequences, exhibit the tub gene product of the invention in situ. These include but are not limited to microorganisms such as bacteria (e.g., *E. coli, B. subtilis*) transformed with recombinant bacteriophage DNA, plasmid DNA or cosmid DNA expression vectors containing tub gene product coding sequences; yeast (e.g., Saccharomyces, Pichia) transformed with recombinant yeast expression vectors containing the tub gene product coding sequences; insect cell systems infected with recombinant virus expression vectors (e.g., baculovirus) containing the tub gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing tub gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the tub gene product being expressed. For example, when a large quantity of such a protein is to be produced, for the generation of pharmaceutical compositions of tub protein or for raising antibodies to tub protein, for example, vectors which direct the expression of high levels of fusion protein products that are readily purified may be desirable. Such vectors include, but are not limited to the E. Coli expression vector pUR278 (Ruther et al., 1983, EMBO J. 2:1791), in which the tub gene product coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed, to include thrombin or factor Xa protease cleavage sites so, that the cloned target gene product can be released from the GST moiety. The Example presented in Section 15, below, describes the successful expression of both murine and human recombinant tub gene products utilizing modified pET vectors (Novagen, Inc., Madison Wis.).

In an insect system, *Autographa californica* nuclear polyhedrosis virus (AcNPV) is used as a vector to express foreign genes. The virus grows in *Spodoptera frugiperda* cells. The tub gene coding sequence may be cloned individually into non-essential regions (for example the polyhedrin gene) of the virus and placed under control of an AcNPV promoter (for example the polyhedrin promoter). Successful insertion of tub gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the tub gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing tub gene product in infected hosts. (E.g., See Logan & Shenk, 1984, Proc. Natl. Acad. Sci. USA 81:3655–3659). Specific initiation signals may also be required for efficient translation of inserted tub gene product coding sequences. These signals include the ATG initiation codon and adjacent sequences. In cases where an entire tub gene, including its own initiation codon and adjacent sequences, is inserted into the appropriate expression vector, no additional translational control signals may be needed. However, in cases where only a portion of the tub gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, and in particular, hypothalamic cell lines such as GN and GH-1 cell lines.

For long-term, high-yield production of recombinant proteins, stable expression is preferred. For example, cell lines which stably express the tub gene product may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the tub gene product. Such engineered cell lines may be particularly useful in screening and evaluation of compounds that affect the endogenous activity of the tub gene product.

These Example presented in Section 15, below, describes the successful expression of recombinant tub gene products in mammalian cell lines.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns and histidine-tagged proteins are selectively eluted with imidazole-containing buffers. The Example presented in Section 15, below, demonstrates the successful expression of carboxy-terminal histidine-tagged recombinant tub gene products.

The tub gene products can also be expressed in transgenic animals. Animals of any species, including, but not limited to, mice, rats, rabbits, guinea pigs, pigs, micro-pigs, goats, and non-human primates, e.g., baboons, monkeys and chimpanzees may be used to generate tub transgenic animals.

Any technique known in the art may be used to introduce the tub gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the tub transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the tub gene transgene be integrated into the chromosomal site of the endogenous tub gene, gene targeting is preferred. Briefly, when such a technique is to be utilized, vectors containing some nucleotide sequences homologous to the endogenous tub gene are designed for the purpose of integrating, via homologous recombination with chromosomal sequences, into and disrupting the function of the nucleotide sequence of the endogenous tub gene. The transgene may also be selectively introduced into a particular cell type, thus inactivating the endogenous tub gene in only that cell type, by following, for example, the teaching of Gu et al. (Gu, et al., 1994, Science 265:103–106). The regulatory sequences required for such a cell-type specific inactivation will depend upon the particular cell type of interest, and will be apparent to those of skill in the art Once transgenic animals have been generated, the expression of the recombinant tub gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of tub gene-expressing tissue, may also be evaluated immunocytochemically using antibodies specific for the tub transgene product.

5.3. Antibodies to Tub Gene Products

Described herein are methods for the production of antibodies capable of specifically recognizing one or more tub gene product epitopes or epitopes of conserved variants or peptide fragments of the tub gene products.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a tub gene product in an biological sample and may, therefore, be utilized as part of a diagnostic or prognostic technique whereby patients may be tested for abnormal levels of tub gene products, and/or for the presence of abnormal forms of the such gene products. The tub gene product also encompasses peptides corresponding to one or more domains of the tub gene product. Such antibodies may also be utilized in conjunction with, for example, compound screening schemes, as described, below, in Section 5.4.2, for the evaluation of the effect of test compounds on tub gene product levels and/or activity. Additionally, such antibodies can be used in conjunction with the gene therapy techniques described, below, in Section 5.4.3, to, for example, evaluate the normal and/or engineered tub-expressing cells prior to their introduction into the patient.

Anti-tub gene product antibodies may additionally be used as a method for the inhibition of abnormal tub gene product activity. Thus, such antibodies may, therefore, be utilized as part of weight disorder treatment methods.

For the production of antibodies against a tub gene product, various host animals may be immunized by injection with a tub gene product, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as a tub gene product, or an antigenic functional derivative thereof. For the production of polyclonal antibodies, host animals such as those described above, may be immunized by injection with tub gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against tub gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.4. Uses of the Tub Gene, Gene Products, and Antibodies

Described herein are various applications of the tub gene, the tub gene product including peptide fragments thereof, and of antibodies directed against the tub gene product and peptide fragments thereof. Such applications include, for example, prognostic and diagnostic evaluation of body weight disorders and the identification of subjects with a predisposition to such disorders, as described, below, in Section 5.4.1. Additionally, such applications include methods for the treatment of body weight and body weight disorders, as described, below, in Section 5.4.2, and for the identification of compounds which modulate the expression of the tub gene and/or the activity of the tub gene product, as described below, in Section 5.4.3. Such compounds can include, for example, other cellular products which are involved in body weight regulation. These compounds can be used, for example, in the amelioration of body weight disorders including obesity, cachexia and anorexia.

While, for clarity, uses related to body weight disorder abnormalities are primarily described in this Section, it is to be noted that each of the diagnostic and therapeutic treatments described herein can additionally be utilized in connection with sensory (e.g., eye and hearing) and fertility defects that are commonly associated with mutations in the tub gene. That is, the diagnostic and prognostic techniques described herein can also be utilized to diagnose tub related eye, hearing and fertility abnormalities and/or a predisposition toward the development of such eye, hearing and fertility abnormalities, while the therapeutic techniques described herein can be utilized for the amelioration of such eye, hearing and fertility defects.

5.4.1. Diagnosis of Body Weight Disorder Abnormalities

A variety of methods can be employed for the diagnostic and prognostic evaluation of body weight disorders, including obesity, cachexia and anorexia, and for the identification of subjects having a predisposition to such disorders.

Such methods may, for example, utilize reagents such as the tub gene nucleotide sequences described in Sections 5.1, and antibodies directed against tub gene products, including peptide fragments thereof, as described, above, in Section 5.3. Specifically, such reagents may be used, for example, for: (1) the detection of the presence of tub gene mutations, or the detection of either over or under-expression of tub gene mRNA relative to the non-body weight disorder state or the qualitative or quantitative detection of alternatively spliced forms of tub transcripts which may correlate with certain body weight disorders or susceptibility toward such body weight disorders; and (2) the detection of either an over or an under-abundance of tub gene product relative to the non-body weight disorder state or the presence of a modified (e.g., less than full length) tub gene product which correlates with a body weight disorder state or a progression toward a body weight disorder state.

The methods described herein may be performed, for example, by utilizing pre-packaged diagnostic kits comprising at least one specific tub gene nucleic acid or anti-tub gene antibody reagent described herein, which may be conveniently used, e.g., in clinical settings, to screen and diagnose patients exhibiting body weight disorder abnormalities and to screen and identify those individuals exhibiting a predisposition to developing a body weight disorder abnormality.

For the detection of tub mutations, any nucleated cell can be used as a starting source for genomic nucleic acid. For the detection of tub transcripts or tub gene products, any cell type or tissue in which the tub gene is expressed, such as, for example, hypothalamus cells, may be utilized.

Nucleic acid-based detection techniques are described, below, in Section 5.4.1.1. Peptide detection techniques are described, below, in Section 5.4.1.2.

5.4.1.1. Detection of Tub Gene Nucleic Acid Molecules

Mutations or polymorphisms within the tub gene can be detected by utilizing a number of techniques. Nucleic acid from any nucleated cell can be used as the starting point for such assay techniques, and may be isolated according to standard nucleic acid preparation procedures which are well known to those of skill in the art.

Genomic DNA may be used in hybridization or amplification assays of biological samples to detect abnormalities involving tub gene structure, including point mutations, insertions, deletions and chromosomal rearrangements. Such assays may include, but are not limited to, direct sequencing (Wong, C. et al., 1987, Nature 330:384–386), single stranded conformational polymorphism analyses (SSCP; Orita, M. et al., 1989, Proc. Natl. Acad. Sci. USA 86:2766–2770), heteroduplex analysis (Keen, T. J. et al., 1991, Genomics 11:199–205; Perry, D. J. & Carrell, R. W., 1992), denaturing gradient gel electrophoresis (DGGE; Myers, R. M. et al., 1985, Nucl. Acids Res. 13:3131–3145), chemical mismatch cleavage (Cotton, R. G. et al., 1988, Proc. Natl. Acad. Sci. USA 85:4397–4401) and oligonucleotide hybridization (Wallace, R. B. et al., 1981, Nucl. Acids Res. 9:879–894; Lipshutz, R. J. et al., 1995, Biotechniques 19:442–447).

Diagnostic methods for the detection of tub gene specific nucleic acid molecules, in patient samples or other appropriate cell sources, may involve the amplification of specific gene sequences, e.g., by the polymerase chain reaction (PCR; the experimental embodiment set forth in Mullis, K. B., 1987, U.S. Pat. No. 4,683,202), followed by the analysis of the amplified molecules using techniques well known to those of skill in the art, such as, for example, those listed above. Utilizing analysis techniques such as these, the amplified sequences can be compared to those which would be expected if the nucleic acid being amplified contained only normal copies of the tub gene in order to determine whether a tub gene mutation exists.

Among those tub nucleic acid sequences which are preferred for such amplification-related diagnostic screening analyses are oligonucleotide primers which amplify tub exon sequences. The sequence of such oligonucleotide primers are, therefore, preferably derived from tub intron sequence so that the entire exon (or coding region) can be analyzed, as discussed below. Primer pairs useful for amplification of tub exons are preferably derived from adjacent introns. For example, in order to amplify tub exon 5, a forward primer derived from the tub intron upstream of exon 5 (i.e., the intron between tub exon 4 and 5) could be used in conjunction with a reverse primer derived from the tub intron downstream of exon 5 (i.e., the intron between tub exon 5 and 6).

Appropriate primer pairs can be chosen such that each of the twelve tub exons are amplified. FIGS. 10A–10G depicts each of human tub exons 4 through 12 and, further, depicts intron sequences flanking each of these exons. Primers for the amplification of tub exons can routinely be designed by one of skill in the art by utilizing such intron flanking sequences.

As an example, and not by way of limitation, Table I, below, Lists primers and primer pairs which can be utilized for the amplification of each of human tub exons 2 through 12. In this table, a primer pair is listed for each of exons 2 through 12, which consists of a forward primer derived from intron sequence upstream of the exon to be amplified and a reverse primer derived from sequence downstream of the exon to be amplified. Each of the primer pairs can be utilized, therefore, as part of a standard PCR reaction to amplify an individual tub exon. For each of the primer pairs listed in Table I, the approximate size of the resulting amplified exon-containing fragment is listed. Utilizing the primer pairs of Table I to amplify human tub exon 5, for example, primers F5 (the forward primer) and R5 (the reverse primer) would be used to amplify a fragment of approximately 250 base pairs that would contain the entire coding region of exon 5.

TABLE I

| HUMAN TUB EXON | PRIMER NAME AND SEQUENCE | | AMPLIFIED FRAGMENT SIZE |
|---|---|---|---|
| 2 | F2 | (SEQ ID NO: 18) 5'-GTT CAA GCT GGT TCC AAG ATG-3' | F2/R2 = 200 bp |
|   | R2 | (SEQ ID NO. 19) 5'-ATC ATC CAG GGA AGA TGG AC-3' | |
| 3 | F3 | (SEQ ID NO: 20) 5'-CTT CCT GGT GGA GGC AGT C-3' | F3/R3 = 220 bp |
|   | R3 | (SEQ ID NO: 21) 5'-GAA GCA GTC ACG GGA TGT GG-3' | |
| 4 | F4 | (SEQ ID NO: 22) 5'-GGG TAC CGA GCT CTG GTC-3' | F4/R4 = 295 bp |
|   | R4 | (SEQ ID NO: 23) 5'-TCC AAG TCA GGA GGA CAA AC-3' | |
| 5 | F5 | (SEQ ID NO: 24) 5'-GAA AGT GCA TCT GAG AAC CTG-3' | F5/R5 = 250 bp |
|   | R5 | (SEQ ID NO: 25) 5'-CCT CCT CCT GGA TGT AAC TC-3' | |
| 6 | F6 | (SEQ ID NO: 26) 5'-TGT GAC CAT GTG TAT TTC AGG-3' | F6/R6 = 234 bp |
|   | R6 | (SEQ ID NO: 27) 5'-CCT CTA ACG GAT GAG CAG TC-3' | |
| 7 | F7 | (SEQ ID NO: 28) F7 5'-GAT TTG GAT CCC AGA CCA CC-3' | F7/R7 = 331 bp |
|   | R7 | (SEQ ID NO: 29) 5'-GAC TTC CAG TCA CAT TTC AGC-3' | |
| 8 | F8 | (SEQ ID NO: 30) 5'-GTG CAG ACC AGA GGC TGA G-3' | F8/R8 = 300 bp |
|   | R8 | (SEQ ID NO: 31) 5'-TTC AGG CCC TCT ACA GAC AG-3' | |
| 9 | F9 | (SEQ ID NO: 32) 5'-TCA TAG GAC AGA CGA TGA GC-3' | F9/R9 = 210 bp |
|   | R9 | (SEQ ID NO: 33) 5'-GTC CTG GAT TTC ATA TCT ACC-3' | |
| 10 | F10 | (SEQ ID NO: 34) 5'-AGG TAA ATA GAC GCC TCA GG-3' | F10/R10 = 218 bp |
|   | R10 | (SEQ ID NO: 35) 5'-ACG TCT GCC CTT AGA AGC TQ-3' | |
| 11 | F11 | (SEQ ID NO: 36) 5'-CTG GAC CTG GCT CAG GTG-3' | F11/R11 = 400 pb |
|   | R11 | (SEQ ID NO: 37) 5'-GTC ATT AGG GTT AGA AAG TTC C-3' | |
| 12 | F12 | (SEQ ID NO: 38) 5'-TCT TCC CTC ATG TGG TTT GG-3' | F12/R12 = 300 bp |
|   | R12 | (SEQ ID NO: 39) 5'-CCA CAG GCA GGC AGG CAA G-3' | |

Additional tub nucleic acid sequences which are preferred for such amplification-related analyses are those which will detect the presence of the tub gene splice site mutation described, below, in Section 10.2 and depicted in FIGS. 7A–7D.

Further, well-known genotyping techniques can be performed to type polymorphisms that are in close proximity to mutations in the tub gene itself. These polymorphisms can be used to identify individuals in families likely to carry mutations. If a polymorphism exhibits linkage disequilibrium with mutations in the tub gene, it can also be used to identify individuals in the general population likely to carry mutations. Polymorphisms that can be used in this way include restriction fragment length polymorphisms (RFLPs), which involve sequence variations in restriction enzyme target sequences, single-base polymorphisms and simple sequence repeat polymorphisms (SSLPs).

For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the tub gene, and the diagnosis of diseases and disorders related to tub mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the tub gene, amplifying the extracted DNA, and labelling the repeat sequences to form a genotypic map of the individual's DNA.

A tub probe could additionally be used to directly identify RFLPs. Additionally, a tub probe or primers derived from the tub sequence could be used to isolate genomic clones such as YACs, BACs, PACs, cosmids, phage or plasmids. The DNA contained in these clones can be screened for single-base polymorphisms or simple sequence length polymorphisms (SSLPs) using standard hybridization or sequencing procedures.

Alternative diagnostic methods for the detection of tub gene-specific mutations or polymorphisms can include hybridization techniques which involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the tub gene. Preferably, the lengths of these nucleic acid reagents are at least 15 to 30 nucleotides. After incubation, all non-annealed nucleic acids are removed from the nucleic acid:tub molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled tub nucleic acid reagents is accomplished using standard techniques well-known to those in the art. The tub gene sequences to which the nucleic acid reagents have annealed can be compared to the annealing pattern expected from a normal tub gene sequence in order to determine whether a tub gene mutation is present.

Among the tub nucleic acid sequences which are preferred for such hybridization analyses are those which will detect the presence of the tub gene splice site mutation described, below, in Section 10.2 and depicted in FIGS. 7A–7D.

Quantitative and qualitative aspects of tub gene expression can also be assayed. For example, RNA from a cell type or tissue known, or suspected, to express the tub gene, such as brain, especially hypothalamus cells, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the tub gene. Such analyses may reveal both quantitative and qualitative aspects of the expression pattern of the tub gene, including activation or inactivation of tub gene expression and presence of alternatively spliced tub transcripts.

In one embodiment of such a detection scheme, a cDNA molecule is synthesized from an RNA molecule of interest (e.g., by reverse transcription of the RNA molecule into cDNA). All or part of the resulting cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the tub gene nucleic acid reagents described in Section 5.1. The preferred lengths of such nucleic acid reagents are at least 9–30 nucleotides.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Such RT-PCR techniques can be utilized to detect differences in tub transcript size which may be due to normal or abnormal alternative splicing. Additionally, such techniques can be performed using standard techniques to detect quantitative differences between levels of full length and/or alternatively spliced tub transcripts detected in normal individuals relative to those individuals exhibiting body weight disorders or exhibiting a predisposition to toward such body weight disorders.

In the case where detection of specific alternatively spliced species is desired, appropriate primers and/or hybridization probes can be used. Using the detection of transcripts containing tub exon 5, for example, appropriate amplification primers can be chosen which will only yield an amplified fragment using cDNA derived from an exon 5-containing transcript. One of the primer pairs can be designed, for example, to specifically utilize an exon 5 sequence. In the absence of such sequence, no amplification would occur. Alternatively, primer pairs may be chosen utilizing the sequence data depicted in FIGS. 6A–6D and FIGS. 9–9D to choose primers which will yield fragments of differing size depending on whether exon 5 is present or absent from the transcript tub transcript being utilized.

As an alternative to amplification techniques, standard Northern analyses can be performed if a sufficient quantity of the appropriate cells can be obtained. Utilizing such techniques, quantitative as well as size related differences between tub transcripts can also be detected.

Additionally, it is possible to perform such tub gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

5.4.1.2. Detection of Tub Gene Products

Antibodies directed against wild type or mutant tub gene products or conserved variants or peptide fragments thereof, which are discussed, above, in Section 5.3, may also be used as body weight disorder diagnostics and prognostics, as described herein. Such diagnostic methods, may be used to detect abnormalities in the level of tub gene expression, or abnormalities in the structure and/or temporal, tissue, cellular, or subcellular location of tub gene product. Because evidence disclosed herein indicates that the tub gene product is an intracellular gene product, the antibodies and immunoassay methods described below have important in vitro applications in assessing the efficacy of treatments for bodyweight disorders such as obesity, cachexia and anorexia. Antibodies, or fragments of antibodies, such as those described below, may be used to screen potentially therapeutic compounds in vitro to determine their effects on tub gene expression and tub peptide production. The compounds which have beneficial effects on body weight disorders, such as obesity, cachexia and anorexia, can be identified, and a therapeutically effective dose determined.

In vitro immunoassays may also be used, for example, to assess the efficacy of cell-based gene therapy for body weight disorders, including obesity, cachexia and anorexia. Antibodies directed against tub peptides may be used in vitro to determine the level of tub gene expression achieved in cells genetically engineered to produce tub peptides. Given that evidence disclosed herein indicates that the tub gene product is an intracellular gene product, such an assessment is, preferably, done using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those which are known, or suspected, to express the tub gents, such as, for example, hypothalamic cells. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cell taken from culture may be a necessary step in the assessment of cells to be used as part of a cell-based gene therapy technique or, alternatively, to test the effect of compounds on the expression of the tub gene.

Preferred diagnostic methods for the detection of tub gene products or conserved variants or peptide fragments thereof, may involve, for example, immunoassays wherein the tub gene products or conserved variants, including gene products which are the result of alternatively spliced transcripts, or peptide fragments are detected by their interaction with an anti-tub gene product-specific antibody.

For example, antibodies, or fragments of antibodies, such as those described, above, in Section 5.3, useful in the present invention may be used to quantitatively or qualitatively detect the presence of tub gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred if such tub gene products are expressed on the cell surface.

The antibodies (or fragments thereof) useful in the present invention may, additionally, be employed histologically, as in immunofluorescence or immunoelectron microscopy, for in situ detection of tub gene products or conserved variants or peptide fragments thereof. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the tub gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for tub gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying tub gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled tub gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-tub gene product antibody may be determined according to well known methods. Those skilled in the art will be able to determine operative and optimal assay conditions for each determination by employing routine experimentation.

One of the ways in which the tub gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect tub gene peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.4.2. Screening Assays for Compounds that Modulate Tub Gene Activity

The following assays are designed to identify compounds that bind to tub gene products, bind to other intracellular proteins that interact with a tub gene product, to compounds that interfere with the interaction of the tub gene product with other intracellular proteins and to compounds which modulate the activity of tub gene (i.e., modulate the level of tub gene expression and/or modulate the level of tub gene product activity). Assays may additionally be utilized which identify compounds which bind to tub gene regulatory sequences (e.g., promoter sequences). See e.g., Platt, K. A., 1994, J. Biol. Chem. 269:28558–28562, which is incorporated herein by reference in its entirety, which may modulate the level of tub gene expression. Compounds may include, but are not limited to, small organic molecules which are able to cross the blood-brain barrier, gain entry into an appropriate cell and affect expression of the tub gene or some other gene involved in the body weight regulatory pathway, or other intracellular proteins. Methods for the identification of such intracellular proteins are described, below, in Section 5.4.2.2. Such intracellular proteins may be involved in the control and/or regulation of body weight. Further, among these compounds are compounds which affect the level of tub gene expression and/or tub gene product activity and which can be used in the therapeutic treatment of body weight disorders, including obesity, cachexia and anorexia, as described, below, in Section 5.4.3.

Compounds may include, but are not limited to, peptides such as, for example, soluble peptides, including but not limited to, Ig-tailed fusion peptides, and members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L- configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Compounds identified via assays such as those described herein may be useful, for example, in elaborating the biological function of the tub gene product, and for ameliorating body weight disorders. Assays for testing the effectiveness of compounds, identified by, for example, techniques such as those described in Section 5.4.2.1–5.4.2.3, are discussed, below, in Section 5.4.2.4.

5.4.2.1. In Vitro Screening Assays for Compounds that Bind to the Tub Gene Product In vitro systems may be designed to identify compounds capable of binding the tub gene products of the invention.

Compounds identified may be useful, for example, in modulating the activity of wild type and/or mutant tub gene products, may be useful in elaborating the biological function of the tub gene product, may be utilized in screens for identifying compounds that disrupt normal tub gene product interactions, or may in themselves disrupt such interactions.

The principle of the assays used to identify compounds that bind to the tub gene product involves preparing a reaction mixture of the tub gene product and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring tub gene product or the test substance onto a solid phase and detecting tub gene product/test compound complexes anchored on the solid phase at the end of the reaction. In one embodiment of such a method, the tub gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for tub gene product or the test compound to anchor any complexes formed in solution, and a labeled antibody specific for the other component of the possible complex to detect anchored complexes.

5.4.2.2. Assays for Intracellular Proteins that Interact with the Tub Gene Product Any method suitable for detecting protein-protein interactions may be employed for identifying tub protein-intracellular protein interactions.

Among the traditional methods which may be employed are co-immunoprecipitation, crosslinking and co-purification through gradients or chromatographic columns. Utilizing procedures such as these allows for the identification of intracellular proteins which interact with tub gene products. Once isolated, such an intracellular protein can be identified and can, in turn, be used, in conjunction with standard techniques, to identify proteins it interacts with. For example, at least a portion of the amino acid sequence of the intracellular protein which interacts with the tub gene product can be ascertained using techniques well known to those of skill in the art, such as via the Edman degradation technique (see, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for gene sequences encoding such intracellular proteins. Screening made be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of genes which encode the intracellular protein interacting with the tub protein. These methods include, for example, probing expression libraries with labeled tub protein, using tub protein in a manner similar to the well known technique of antibody probing of $\lambda$gt11 libraries.

One method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the tub gene product and the other consists of the transcription activator protein's activation domain fused to an unknown protein that is encoded by a cDNA which has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, tub gene products may be used as the bait gene product. Total genomic or cDNA sequences are fused to the DNA encoding an activation domain. This library and a plasmid encoding a hybrid of a bait tub gene product fused to the DNA-binding domain are cotransformed into a yeast reporter strain, and the resulting transformants are screened for those that express the reporter gene. For example, and not by way of limitation, a bait tub gene sequence, such as the 1.5 kb open reading frame of the tub gene, as depicted in FIGS. 6A–6D or FIGS. 9A–9D can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait tub gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait tub gene-GAL4 fusion plasmid into a yeast strain which contains a lacZ gene driven by a promoter which contains GAL4 activation sequence. A cDNA encoded protein, fused to GAL4 transcriptional activation domain, that interact, with bait tub gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait tub gene-interacting protein using techniques routinely practiced in the art.

5.4.2.3. Assays for Compounds that Interfere with Tub Gene Product/Intracellular Macromolecule Interaction The tub gene products of the invention may, in vivo, interact with one or more intracellular macromolecules, such as proteins. Such macromolecules may include, but are not limited to, nucleic acid molecules and those proteins identified via methods such as those described, above, in Section 5.4.2.2. For purposes of this discussion, such intracellular macromolecules are referred to herein as "binding partners". Compounds that disrupt tub binding in this way may be useful in regulating the activity of the tub gene product, especially mutant tub gene products. Such compounds may include, but are not limited to molecules such as peptides, and the like, as described, for example, in Section 5.4.2.1. above, which would be capable of gaining access to the intracellular tub gene product.

The basic principle of the assay systems used to identify compounds that interfere with the interaction between the tub gene product and its intracellular binding partner or partners involves preparing a reaction mixture containing the tub gene product, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of tub gene product and its intracellular binding partner. Control reaction mixtures are incubated without the test compound or with a placebo. The formation of any complexes between the tub gene protein and the intracellular binding partner is then detected. The formation of a complex in the control reaction, but not in the reaction mixture containing the test compound, indicates that the compound interferes with the interaction of the tub gene protein and the interactive binding partner. Additionally, complex formation within reaction mixtures containing the test compound and normal tub gene protein may also be compared to complex formation within reaction mixtures containing the test compound and a mutant tub gene protein. This comparison may be important in those cases wherein it is desirable to identify compounds that disrupt interactions of mutant but not normal tub gene proteins.

The assay for compounds that interfere with the interaction of the tub gene products and binding partners can be conducted in a heterogeneous or homogeneous format. Heterogeneous assays involve anchoring either the tub gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the tub gene products and the binding partners, e.g., by competition, can be identified by conducting the reaction in the presence of the test substance; i.e., by adding the test substance to the reaction mixture prior to or simultaneously with the tub gene protein and interactive intracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the tub gene produce or the interactive intracellular binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the tub gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the tub gene protein and the interactive intracellular binding partner is prepared in which either the tub gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt tub gene protein/intracellular binding partner interaction can be identified.

In a particular embodiment, the tub gene product can be prepared for immobilization using recombinant DNA techniques described in Section 5.2. above. For example, the tub coding region can be fused to a glutathione-S-transferase (GST) gene using a fusion vector, such as pGEX-5X-1, in such a manner that its binding activity is maintained in the resulting fusion protein. The interactive intracellular binding partner can be purified and used to raise a monoclonal antibody, using methods routinely practiced in the art and described above, in Section 5.3. This antibody can be labeled with the radioactive isotope $^{125}$I, for example, by methods routinely practiced in the art. In a heterogeneous assay, e.g., the GST-tub fusion protein can be anchored to glutathione-agarose beads. The interactive intracellular binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the tub gene protein and the interactive intracellular binding partner can be detected by measuring the amount of radioactivity that remains associated with the glutathione-agarose beads. A successful inhibition of the interaction by the test compound will result in a decrease in measured radioactivity.

Alternatively, the GST-tub gene fusion protein and the interactive intracellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the tub gene product/binding partner interaction can be detected by adding the labeled antibody and measuring the radioactivity associated with the beads.

In another embodiment of the invention, these same techniques can be employed using peptide fragments that correspond to the binding domains of the tub protein and/or the interactive intracellular or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a tub gene product can be anchored to a solid material as described, above, in this Section by making a GST-tub fusion protein and allowing it to bind to glutathione agarose beads. The interactive intracellular binding partner can be labeled with a radioactive isotope, such as $^{35}$S, and cleaved with a proteolytic enzyme such as trypsin. Cleavage products can then be added to the anchored GST-tub fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

5.4.2.4. Assays for Identification of Compounds that Ameliorate Body Weight Disorders Compounds, including but not limited to binding compounds identified via assay techniques such as those described, above, in Sections 5.4.2.1–5.4.2.3, can be tested for the ability to ameliorate body weight disorder symptoms, including obesity. It should be noted that although tub gene products are intracellular molecules which are not secreted and have no transmembrane component, the assays described herein can identify compounds which affect tub gene activity by either affecting tub gene expression or by affecting the level of tub gene product activity. For example, compounds may be identified which are involved in another step in the pathway in which the tub gene and/or tub gene product is involved and, by affecting this same pathway may modulate the affect of tub on the development of body weight disorders. Such compounds can be used as part of a therapeutic method for the treatment of body weight disorders.

Described below are cell-based and animal model-based assays for the identification of compounds exhibiting such an ability to ameliorate body weight disorder symptoms.

First, cell-based systems can be used to identify compounds which may act to ameliorate body weight disorder symptoms. Such cell systems can include, for example, recombinant or non-recombinant cell, such as cell lines, which express the tub gene. For example, hypothalamus cells, such as, for example GH-1 (Melcang; R. C. et al., 1995, Endocrinology 136:679–686) and GN (Radovick, S. et al., 1991, Proc. Natl. Acad. Sci. USA 88:3402–3406) hypothalamic cell lines can be used.

In utilizing such cell systems, cells may be exposed to a compound, suspected of exhibiting an ability to ameliorate body weight disorder symptoms, at a sufficient concentration and for a time sufficient to elicit such an amelioration of body weight disorder symptoms in the exposed cells. After exposure, the cells can be assayed to measure alterations in the expression of the tub gene, e.g., by assaying cell lysates for tub mRNA transcripts (e.g., by Northern analysis) or for tub protein expressed in the cell; compounds which increase expression of the tub gene are good candidates as therapeutics. Alternatively, the cells are examined to determine whether one or more body weight disorder-like cellular phenotypes has been altered to resemble a more normal or more wild type, non-body weight disorder phenotype, or a phenotype more likely to produce a lower incidence or severity of disorder symptoms.

In addition, animal-based body weight disorder systems, which may include, for example tub mice, may be used to identify compounds capable of ameliorating body weight disorder-like symptoms. Such animal models may be used as test substrates for the identification of drugs, pharmaceuticals, therapies and interventions which may be effective in treating such disorders. For example, animal models may be exposed to a compound, suspected of exhibiting an ability to ameliorate body weight disorder symptoms, at a sufficient concentration and for a time sufficient to elicit such an amelioration of body weight disorder symptoms in the exposed animals. The response of the animals to the exposure may be monitored by assessing the reversal of disorders associated with body weight disorders such as obesity. With regard to intervention, any treatments which reverse any aspect of body weight disorder-like symptoms should be considered as candidates for human body weight disorder therapeutic intervention. Dosages of test agents may be determined by deriving dose-response curves, as discussed in Section 5.5.1, below.

5.1.3. Compounds and Methods for the Treatment of Body Weight

Described below are methods and compositions whereby body weight including body weight disorders, including obesity, cachexia and anorexia may be treated. Because a loss of normal tub gene product function results in the development of an obese phenotype, an increase in tub gene product activity would facilitate progress towards a normal body weight state in individuals exhibiting a deficient level of tub gene expression and/or tub gene product activity.

Alternatively, symptoms of certain body weight disorders such as, for example, cachexia, which involve a lower than normal body weight phenotype, may be ameliorated by decreasing the level of tub gene expression and/or tub gene product activity. For example, tub gene sequences may be utilized in conjunction with well-known antisense, gene "knock-out," ribozyme and/or triple helix methods to decrease the level of tub gene expression. Such methods can also be useful for agricultural applications in which a more favorable fat:level body mass ratio (i.e., a decreased ratio) is desired.

With respect to an increase in the level of normal tub gene expression and/or tub gene product activity, tub gene nucleic acid sequences, described, above, in Section 5.1, can, for example, be utilized for the treatment of body weight disorders, including obesity. Such treatment can be administered, for example, in the form of gene replacement therapy. Specifically, one or more copies of a normal tub gene or a portion of the tub gene that directs the production of a tub gene product exhibiting normal tub gene function, may be inserted into the appropriate cells within a patient, using vectors which include, but are not limited to adenovirus, adeno-associated virus, and retrovirus vectors, in addition to other particles that introduce DNA into cells, such as liposomes.

Because the tub gene is expressed in the brain, including the hypothalamus, such gene replacement therapy techniques should be capable delivering tub gene sequences to these cell types within patients. Thus, the techniques for delivery of tub gene sequences should be able to readily cross the blood-brain barrier, which are well known to those of skill in the art (see, e.g., PCT application, publication No. WO89/10134, which is incorporated herein by reference in its entirety), or, alternatively, should involve direct administration of such tub gene sequences to the site of the cells in which the tub gene sequences are to be expressed. With respect to delivery which is capable of crossing the blood-brain barrier, viral vectors such as, for example, those described above, are preferable.

Additional methods which may be utilized to increase the overall level of tub gene expression and/or tub gene product activity include the introduction of appropriate tub-expressing cells, preferably autologous cells, into a patient at positions and in numbers which are sufficient to ameliorate the symptoms of body weight disorders, including obesity. Such cells may be either recombinant or non-recombinant.

Among the cells which can be administered to increase the overall level of tub gene expression in a patient are normal cells, preferably hypothalamus cells, which express the tub gene. Among the hypothalamic cells which can be administered are hypothalamic cell lines, which include, but are not limited to the GT1-1 cell line (Melcangi, R. C. et al., 1995, Endocrin. 136:679–686).

Alternatively, cells, preferably autologous cells, can be engineered to express tub gene sequences which may then be introduced into a patient in positions appropriate for the amelioration of body weight disorder symptoms. Alternately, cells which express the tub gene in a wild type in MHC matched individuals, i.e., non-tub individual, and may include, for example, hypothalamic cells. The expression of the tub gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, F., U.S. Pat. No. 5,399,349.

When the cells to be administered are non-autologous cells, they can be administered using well known techniques which prevent a host immune response against the introduced cells from developing. For example, the cells may be introduced in an encapsulated form which, while allowing for an exchange of components with the immediate extra-cellular environment, does not allow the introduced cells to be recognized by the host immune system.

Additionally, compounds, such as those identified via techniques such as those described, above, in Section 5.4.2, which are capable of modulating tub gene product activity can be administered using standard techniques which are well known to those of skill in the art. In instances in which the compounds to be administered are to involve an interaction with brain cell types such as, for example, hypothalamic cell types, the administration techniques should include well known ones which allow for a crossing of the blood-brain barrier.

5.5. High-Throughput Screening Assays for Drugs useful in Regulation of Body Weight At least two different assay systems, described in the subsections below, can be designed and used as high-throughput screening assays to identify compounds or compositions that modulate or alter tub gene product activity, and therefore, modulate weight control. The screening assays described herein may be used singly or in combination with other assays, including animal models, to identify compounds which modulate tub gene product activity.

The systems described below may be formulated into kits. To this end, the tub gene product, either wild type or mutant, or cells expressing the tub gene product, either wild type or mutant, can be packaged in a variety of containers, e.g., vials, tubes, microtitre well plates, bottles and the like. Other reagents can be included in separate containers and provided with the kit, e.g., positive controls samples, negative controls samples, SH2 containing peptides and/or proteins, reporter constructs, buffers, cell culture media, etc.

In addition, animal-based systems or models for a body weight disorder may be used to identify compounds capable of ameliorating symptoms of the disorder. Such animal models may be used as test substrates for the identification of drug pharmaceuticals, therapies and interventions, including compounds, small molecules, ribozymes and antisense molecules that may be effective in treating such disorders. Any compound tested in the high-throughput screening assays as may be tested in animals. In particular, any compound identified in the high-throughput assays as altering tub gene product activity may further be tested in an animal. For example animal models may be exposed to a compound suspected of exhibiting an ability to ameliorate symptoms, at a sufficient concentration and for a sufficient time to elicit such an amelioration of a tub gene related disorder in the exposed animals. The response of the animals to the exposure may be monitored by assessing the reversal of such symptoms or any other way found suitable to assay the effects of such compounds in animals or humans.

5.5.1. Cell-Based Assays

In accordance with the invention, a cell-based assay system can be used to screen for compounds that modulate the activity of tub gene product and thereby, modulate body weight. To this end, cells, or lysates thereof, that endogenously express tub gene product, either wild type or mutant, can be used to screen for compounds useful in the alteration or modulation of tub gene product activity. Cells isolated from transgenic animals engineered to express the tub gene product or primary cells expressing the tub gene product isolated from animal or human tissue may be used for screening purposes. Alternatively, cell lines genetically engineered to express the tub gene product as described in Section 5.2 above, or lysates thereof, may be used for screening purposes. Preferably, host cells genetically engineered to express a functional insulin receptor and/or reporter genes regulated by insulin or lysates thereof, may be used for screening purposes.

In utilizing such cell systems, the cells expressing tub gene product and an insulin receptor are exposed to a test compound or to vehicle controls (e.g., placebos). After exposure, no cells are stimulated with insulin or IGF-1 the cells can then be assayed to measure the expression and/or activity of components of the signal transduction pathway of the insulin receptor, or the activity of the signal transduction pathway itself can be assayed. In this regard, any intermediate step in the signal transduction pathway can be measured or assayed to determine the effect of the test compound on the activity of the tub gene product in the signal transduction pathway. For example, after exposure, cell lysates can be assayed for induction of phosphotidylinositol turnover. The ability of a test compound to increase levels of phosphotidylinositol turnover measured by calcium flux, different than those levels seen with cells treated with a vehicle control indicates that the test compound modulates signal transduction mediated by stimulation of tub gene product.

For example, to determine phosphotidylinositol turnover measured by calcium flux, a bioluminescence assay may be utilized such as those described in Brownstein, I. et al. (1994, Biotechniques 17:172–177). The assay utilizes cells, or lysates thereof, which have been transfected with DNA vectors encoding the insulin receptor with or without DNA vectors encoding tub gene product. The cells are labeled with a calcium sensitive bioluminescent protein. Test compounds or vehicle controls are added to the cells. The cells are stimulated with insulin or insulin growth factor-1 (IGF-1) for approximately 30 minutes. The cells are assayed for bioluminescence. The assay may be performed in a 96 well-based plate to enable high-throughput screening. Such assays provide a simple, sensitive, easily automatable detection system for pharmaceutical screening.

In another embodiment, constructs containing an insulin or IGF-responsive element, such as the NPY promoter, linked to any of a variety of different reporter genes may be introduced into cells expressing the insulin receptor with or without tub gene product. Such reporter genes may include but are not limited to chloramphenicol transferase (CAT), luciferase, GUS, growth hormone or placental alkaline phosphatase (SEAP). Alkaline phosphatase or luciferase assays are particularly useful in the practice of the invention as the enzyme is secreted from the cell and/or is easily assayed. Wherein a NPY promoter is used, the cells are stimulated with nerve growth factor (NGF) for a minimum of six hours. Following exposure of the cells to test compound and subsequently insulin or IGF-1 the level of reporter gene expression may be quantitated to determine the test compound's ability to regulate tub gene product activity. Alkaline phosphatase activity may be assayed from tissue culture supernatant. In addition, alkaline phosphatase or luciferase activity may be measured by calorimetric, bioluminescent or chemiluminescent assays such as those described in Brownstein, I. et al. (1994, Biotechniques 17:172–177). Such assays provide a rapid and simple, detection system for pharmaceutical screening.

In another embodiment of the present invention, subcellular localization of tub gene product can be assayed following exposure to a test compound. As demonstrated by the Applicants, following stimulation of cells with insulin the level of tub gene product found in the nucleus decreases and levels of tub gene product found in the cytoplasm increase. As an example of this embodiment, cells engineered to express green fluorescent protein (GFP)-tub may be stimulated with insulin or IGF-1 and exposed to test compound. Thus, following exposure of the cells to the test compound, the levels of tub gene product in the nucleus can be measured to determine the test compound's ability to regulate tub gene product activity and localization and to identify those compounds which result in the cytoplasmic accumulation of tub gene product.

In yet another embodiment, subcellular localization of tub gene product following exposure to test compounds may also be determined by measuring the phosphorylation of tub gene product's tyrosine residues and/or serine/threonine residues. As an example, cells expressing insulin receptor and tub gene product are serum starved and exposed to test compound and are stimulated with insulin or IGF-1 test compound in a 96-well plate. The cells are lysed and centrifuged to remove the nucleus and cellular debris. The cell lysate is added to a second 96-well plate which contains immobilized SH2 containing peptides or immobilized anti-phosphotyrosine antibody. In accordance with the present invention, SH2 containing peptides comprise any peptide or protein which contains an SH2 binding domain including, but not limited to the following proteins or fragments thereof, PLC gamma, Abl, Lck, Hck, Fgr, BLk, Src, Fyn, Yes and Lyn kinases. To detect cytoplasmic tub gene product an anti-tub gene product antibody, tagged with a radioactive label, is added. The assay may be performed in a 96-well plate to enable high-throughput screening and 96 well-based scintillation counting instruments may be used for readout.

5.5.2. Cell-Free Assays

In addition to cell based assays, non-cell based assay systems may be used to identify compounds that regulate or alter the activity of tub gene product. In accordance with the invention, recombinantly expressed tub gene products, including phosphorylated tub gene products, or cell lysates obtained from cells that express tub gene products may be used in the screening assays described herein. Such compounds may act as agonists or antagonists of tub gene product activity and may be used in the treatment of body weight disorders.

In one embodiment of the cell free assays of the invention, the interaction of tub gene product with SH2 domains of proteins such as PLC gamma (carboxy terminal SH2), Abl, Lck, Src, etc. following exposure to test compounds. To determine these interactions, a scintillation proximity assay (SPA) may be utilized (SPA kit is provided by Amersham Life Sciences, Ill.). The assay utilizes the SH2 domain of proteins such as PLC gamma (the carboxy terminal SH2), Abl, Lck and Src or other relevant SH2 domains immobilized on the surface of a 96-well plate. Test compounds are added which are either agonists or antagonists. Tyrosine phosphorylated tub gene product is added to the assay system. tub gene product binding to the immobilized SH2 domains is measured by scintillation proximity assay. The assay may be performed in 96-well plates to enable high-throughput screening and 96 well-based scintillation counting instruments such as those manufactured by Wallace or Packard may be used for readout.

Alternatively, in yet another embodiment of the cell free assays of the present invention, activation of tub gene product following exposure to a test compound may be determined by measuring the tyrosine phosphorylated state of tub gene product. As an example, tub gene product may be immobilized to the surface of 96-well plates. The immobilized tub gene product is exposed to cellular extracts obtained from cells stimulated with insulin with or without the test compound. Following incubation, the cell extract is removed and the tyrosine phosphorylated state of tub gene product is determined by the ability of an antibody which recognize phosphorylated tyrosine residues to specifically bind the immobilized tub gene product. The interaction between tub gene product and the antibody may be determined by scintillation proximity assay. Such assays provide high-throughput assays which serve as simple, easily automatable detection systems for pharmaceutical screening.

5.6. Pharmaceutical Preparations and Methods of Administration

The compounds that are determined to affect tub gene expression or gene product activity can be administered to a patient at therapeutically effective doses to treat or ameliorate weight disorders, including obesity. A therapeutically effective dose refers to that amount of the compound sufficient to result in amelioration of symptoms of body weight disorders.

5.6.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_5$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.6.2. Formulations and use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

6. EXAMPLE: GENETIC MAPPING OF THE tub LOCUS

In the Example presented herein, studies are described which, first, define the genetic interval within which the tub gene lies, and, second, successfully narrow the interval to approximately 0.25 cM.

6.1. Materials and Methods

The tubby phenotype. The tubby phenotype was assessed by weighing the mice. Females weighing less than 35 grams at 150 days were classified as normal (i.e., either +/+ or tub/+), while those weighing greater than 43 grams were typed as tub/tub. Males weighing more than 55 grams at 150 days were classified as tub/tub, while males weighing less than 55 grams were classified as unknown.

The markers used to genotype the crosses were those identified and mapped at the Whitehead Institute at the Massachusetts Institute of Technology (Dietrich et al., 1992, Genetics 131:423–447).

The European backcross mapping panel (Breen et al., 1994, Human Mol. Genet. 3:621–627), which consists of a C57BL/6J×Mus Spretus backcross, was used to order markers within the tub gene interval.

Hbb protein polymorphism typing is described in Whitney, J. B. III, 1978, Biochem. Genet. 16:667–672.

Mouse crosses were performed according to standard procedures.

6.2. Results

The murine tub gene had previously been mapped to 2.4 cM ±1.4 cM distal of the hemoglobin beta locus (Hbb) on mouse chromosome 7 (Jones, J. M. et al., 1992, Genomics 14:197–199). 2.4 cM represents a genetic distance measurement corresponding to 3 observed genetic crossovers in 125 opportunities. On average, in the mouse genome, this is equivalent to a physical distance of approximately 4.8 million base pairs. This level of genetic resolution, however, was not satisfactory for the cloning of the tub gene. Further, the region of chromosome 7 containing the tub gene was not well defined, and no defined markers existed which flanked the tub locus.

Described herein, therefore, are genetic crosses which: 1) define the chromosomal region surrounding the tub gene, and 2) narrow the interval within which the tub gene is determined to lie to 0.25 cM.

Specifically, two large crosses segregating the tubby phenotype were set up and performed, and were typed with available genetic markers known to map within the relevant region of chromosome 7.

First, an intercross of [C57BL/6J-tub×DBA/2J] $F_1$ hybrid mice was set up. These hybrid mice were the progeny derived from the mating of two inbred stains, C57BL/6J-tub/tub and DBA/2J-+/+. In total, 417 $F_2$ progeny, representing 838 independent meioses, were analyzed. Typing all informative markers against this cross identified a genomic region of approximately 4 megabases between the markers D7Mit17 and D7Mit281 which contained the tub gene. Two $F_2$ progeny showed recombination events between D7Mit17 and the tub locus, thereby establishing this marker as proximal to the tub locus. Five recombinant $F_2$ progeny demonstrated that the tub locus lies proximal to the D7Mit281 marker, thus placing the tub locus between the D7Mit17 and D7Mit281 markers, as shown in FIG. 1. The distance between the markers D7Mit17 and D7Mit281 was determined to be about 2.0 cM, thereby narrowing the interval within which the tub gene must lie to this 2.0 cM region.

The tub genetic interval was further narrowed by exploiting a by product of the way in which tub stock is maintained. tub heterozygotes must be identified in order to easily maintain the stock because tub homozygotes have reduced fertility. In order to maintain such heterozygotes, a C57BL/6J-tub strain was crossed with the congenic C57BL/6J-Hbb$^P$ strain. This congenic strain is presumed to be genetically identical to the C57BL/6J strain except for a genomic segment from a wild mouse strain surrounding and including the Hbb locus. As a result, the C57BL/6J-Hbb$^P$ strain has an Hbb allele (Hbb$^P$) which can be distinguished electrophoretically from the C57BL/6J Hbb allele (Hbb$^S$). Because the Hbb locus is closely linked to the tub locus, those animals found to be Hbb$^P$/Hbb$^S$ were presumed to be heterozygous at the tub locus as well (a subset of animals were tested for the tubby phenotype later, to assure that no recombination between the Hbb and tub loci had taken place).

Because the two markers under selection for heterozygosity in such a maintenance scheme are Hbb and tub, the genomic region between these two loci also remains heterozygous as the stock is propagated. However, with each successive generation, this region will narrow, and the region outside this interval will become homozygous for C57BL/6J alleles.

By genotyping of the parental strains C57BL/6J and C57BL/6J-Hbb$^P$, the boundaries of the original congenic interval surrounding the Hbb locus were established. Proximal of the tub locus, the congenic interval includes the markers D7Mit17, 39, 33, 37 and 38. The congenic interval extends distally beyond the marker D7Mit222 and includes the markers D7Mit130 and 53.

The genotyping of the C57BL/6J-tub/+-Hbb$^S$/Hbb$^P$ strains generated herein, led to the finding that the markers D7Mit39, 53 and 22 were homozygous for C57BL/6J alleles in each of the animals of this strain which were tested. This showed that the congenic interval had been narrowed, through subsequent generations, to an interval between D7Mit39 and D7Mit53 (D7Mit39 is 0.3 cM proximal to D7Mit17). Because the tub locus is, by necessity, heterozygous in these animals, it must also, therefore, lie within this D7Mit39-to-D7Mit53 interval. Based on the typing of 982 progeny of the European backcross mapping panel (Breen et al., 1994, Human Mol. Genet. 3:621–627), this interval was estimated to be approximately 0.5 cM.

Next, the tub maintenance stock was used as a cross. Because heterozygous mice of this stock (C57BL/6J-tub/+) were heterozygous for markers within the congenic interval, such a cross represented an $F_1$ intercross segregating tubby in a manner analogous to the tub/DBA/2J intercross. 394 meioses were genotyped and a single recombinant mouse was identified, demonstrating that the tub locus lies proximal to the D7Mit130 marker. Thus, at this point in the genetic mapping, the proximal boundary of the tub interval was D7Mit17, as defined by the recombinants isolated from the [C57BL/6J-tub×DBA/2J] $F_1$ intercross and the distal boundary of the tub interval was D7Mit130, as shown by the recombinant of this C57BL/6J-tub/+ intercross. The total number of meioses genotyped at this point was 1232: 838 meioses in the [C57BL/(3J-tub×DBA/2J] $F_1$ intercross and 394 meioses in the maintenance stock intercross.

The size of this region was estimated to be approximately 0.25 cM on the European backcross panel. On average in the mouse genome, such a genetic distance corresponds to a physical distance of approximately 500 kb. This finding led to efforts to clone the intervening DNA in an attempt to isolate the tub gene.

7. EXAMPLE: PHYSICAL MAPPING OF THE tub GENE INTERVAL

As a step toward identifying the tub gene, the Example presented herein describes the physical mapping of the D7Mit17 to D7Mit53 interval within which the tub gene was determined to lie.

7.1. Materials and Methods

Yeast artificial chromosome (YAC) libraries. Two mouse genomic YAC libraries were screened in an effort to identify specific YACs containing genomic DNA from the tub region. The first YAC library, the Whitehead Mouse YAC Library I, was obtained from Research Genetics (Huntsville, Ala.). The second YAC library, the St. Mary's/ICRF YAC library, was a composite library made of YACs constructed at St. Mary's Hospital (London, England) and of YACs constructed at the Imperial Cancer Research Fund laboratories and it was obtained from St. Mary's Hospital.

The YAC libraries were screened by PCR amplification of DNA pools representing the libraries. A description of a screening protocol can be found in Research Genetics Catalog No. 95020.

The terminal sequences of the YACs were isolated by vectorette PCR according to Riley et al., 1990, Nucl. Acids Res. 18.2887–2890). Sequencing was performed according to standard procedures.

YAC ends were mapped according to the protocol described by Tuffrey et al., 1993, Hum. Mut. 2:368–374 for single-stranded conformational polymorphism (SSCP) analysis, using SSCPs identified between C57BL/6J and Mus spretus (the two mouse strains used to generate the European Backcross mapping panel). Utilizing the YAC end SSCPs it was possible to determine that the ends of the YACs mapped between the D7Mit17 and D7Mit53 markers.

P1 bacteriophage. A mouse genomic P1 bacteriophage library (Pierce, J. C. et al., 1992, Mamm. Genome 3:550–558) was screened using the Genome Systems screening service. For screening, the ura end of the M72 YAC (M72R) was identified via vectorette PCR (Riley et al., 1990, Nucl. Acids Res. 18:2887–2890). M72R was sequenced and two PCR fragments were chosen from this sequence, as shown below:

M72R-f (SEQ ID NO:40): 5'-TGC GCA GAA ACA ATC ACC TA-3'; and

M72R-r (SEQ ID NO:41): 5'-CAA GAC GTG AAC CTG GA-3'

The two primers amplify a 129 bp fragment from mouse genomic DNA. The primers were used by Genome Systems screening service to screen the mouse genomic P1 library.

Bacterial Artificial Chromosomes (BACs). A MIT/Research mouse BAC library obtained from Research Genetics (Catalog No. 96023) was screened according to manufacturer's suggested screening protocol.

7.2. Results

Described herein are results which describe the physical mapping of the tub region. This region is shown in FIG. 1. In FIG. 1, genetic markers are indicated above the top line, while YACs spanning the region are shown below this. The checkered P1 and BAC clones were analyzed by sequence sampling and exon trapping (see Section 8, below). Overlaps between clones were identified by PCR amplification of clones with physical markers in the region. The tub gene, as described, below, in this section, was mapped between D7Mit17 and D7Mit53.

The markers D7Mit 127, 219, 63, 280, 236 and 130 were mapped between the D7Mit17 and D7Mit53 markers on the European Backcross panel (Breen et al., 1994, Human Mol. Genet. 3:621–627). These markers, including the D7Mit17 and D7Mit53 markers, were used, therefore, to screen the MIT YAC library.

Screening with these markers resulted in the identification of a set of YACs which constituted two contigs. Specifically, the contig around D7Mit17 included YACs M65, M70 and M72, while the contig around D7Mit53 included M49, M79 and M31.

In order to clone the gap between the two YAC contigs, physical PCR markers at the ends of the YACs were established, via vectorette PCR (Riley, 1990, Nucl. Acids Res. 18:2887–2890), with which to rescreen the YAC library. The resulting PCR products were sequenced and PCR screening primers were chosen. The trp ends of YACs M70 and M31 were isolated (trp ends will be referred to herein as the left end of the YACs, e.g., M70L, while the ura ends will be referred to herein as the right ends), and were genetically mapped, as described, above, in Section 6.1, to the tub region of mouse chromosome 7 in order to show that they were not derived from chimeric YACs. These ends were then used to screen the St. Mary's/ICRF YAC library.

One YAC, M84, was identified by both M70L and M31L. Thus, a single contig spanning the D7Mit17 to D7Mit53 was established. The minimal contig consisted of M65, M72, M84, M31, M79 and M49, as shown in FIG. 1.

In order to further aid in gene identification and to confirm the integrity of the YAC contig described above, P1 bacteriophage and bacterial artificial chromosomes (BACS) were established for the interval between D7Mit17 and D7Mit130. These P1 clones and BACs overlap to form three contigs separated by two gaps, as shown in FIG. 1.

8. EXAMPLE: IDENTIFICATION OF A CANDIDATE tub GENE

In the Example presented herein, a gene is identified, via exon trapping and sequence sampling, within the cloned DNA described in the Example presented, above, in Section 7, which corresponds to a candidate tub gene. Specifically, Section 8.1 describes the exon trapping and sequencing analyses, while Section 8.2 describes the cloning of putative tub gene cDNA clones.

8.1. Exon Trapping and Sequence Sampling of Tub Gene Interval DNA Materials and Methods Eleven P1 (P1, P2, P3, P4, P6, P7, P8, P10, P11, P13 and P14) and twelve BAC (B1, B2, B3, B4, B5, B6, B7, B9, B12, B13, B14 AND B15) clones were subcloned into the D-pSPL3, vector, exon trapped and sequence sampled, as described below.

Exon trapping. The exon trapping analysis was performed using Gibco BRL Exon Trapping System (Cat. No. 18449-017) and using the D-pSPL3 vector, a modified version of the pSPL3 vector (Gibco BRL Life Sciences). In this system, exons are trapped from genomic DNA subcloned into the vector as a result of the interaction between the vector splice site and splice sites flanking exons in the genomic DNA.

D-pSPL3 was derived from the splicing vector pSPL3 (Gibco BRL Life Sciences) by deletion of the NdeI (1119)-NheI (1976) fragment in the HIV tat intron to eliminate the cryptic splice-donor site at position 1134 in the pSPL3 sequence. Stocks of BamHI-cut and PstI-cut D-pSPL3 DNA were prepared by digesting 50–100 µg DNA with the corresponding enzyme and dephosphorylating the linearized vector with calf intestinal alkaline phosphatase as specified by the manufacturers (New England Biolabs and Boerhinger Mannheim, respectively). The linearized vector was purified away from uncut plasmid DNA by agarose gel electrophoresis and electroelution and assayed to assess the level of uncut and self-ligated vector as described elsewhere (Pulido and Duyk, 1994, in Current Protocols in Human Genetics, Wiley Pub., pp 2.2.1–2.3.1).

Briefly, P1 and BAC clone DNA was prepared from overnight cultures (100 ml LB/kanamycin 25 µg/ml) by standard alkaline lysis, treated with RNase A, purified by phenol/chloroform/isoamyl alcohol (25:24:1) extraction, ethanol precipitated, rinsed in 70% ethanol, dried and resuspended in 400 µl deionized water.

5–10 µg P1/BAC DNA was cut with either BamHI and BglII, or PstI, as specified by the manufacturer (New England Biolabs, Beverly, Mass.). The digested DNA was phenol extracted, ethanol precipitated and resuspended in 50 µl deionized water.

Exon trapping was then completed as described in the Gibco BRL Exon Trapping Manual. Briefly, the D-pSPL3 clones were transfected into COS-7 cells. RNA was isolated and first strand cDNA was synthesized. Two rounds of nested PCR specifically amplified transcripts derived from the D-pSPL3 clones. These PCR products were cloned into the vector pAMP10. Clones from this pAMP10 library of trapped fragments were then analyzed by PCR to determine insert sizes. Clones with insert sizes greater than 150 bp were sequenced using M13 forward and reverse primers. One of the D-pSPL3 subclones was designated ium008p004, and was sequenced.

A 90 bp fragment, designated P8X1, was PCR amplified using the sequence of this subclone insert. The P8X1 fragment was generated using two PCR primers which were designed using the ium008p004 sequence as follows:

P8X1F1 (SEQ ID NO:42): 5'-GCG GAT ACA GAC TCT CTC AT-3'

P8X1R1 (SEQ ID NO:43): 5'-GAG GAC AAA TGT CCT AGG CT-3'

The 90 bp P8X1 DNA fragment was PCR amplified from first strand cDNA made from C57BL/6J mouse brain RNA. Standard cDNA synthesis and PCR procedures were utilized.

Sequence sampling. Sequence sampling is a technique for rapidly determining whether coding sequences were present in a nucleic acid sample of interest (See Claverie, J. M., 1994, Genomics 23:575–581). The inserts in D-pSPL3 clones described above were sequenced in both orientations using the following primers:

SPL3A (SEQ ID NO:44): 5'-CAT GCT CCT TGG GAT GT-3'

SPL3C (SEQ ID NO:45): 5'-TGA GGA TTG CTT AAA GA-3'

After vector trimming and quality assessment, the resulting sequences were compared to nucleic acid and protein databases using BLAST algorithms (Altschul, S. F. et al., 1990, J. Mol. Biol. 215:403–410).

Results

In order to look for genes within the cloned DNA, described, above, in Section 7, within the interval containing the tub gene, P1 and BAC clones were subcloned into the D-pSPL3 vector and exon trapped and sample sequenced, as described, above, in the Materials and Methods portion of this section. One of the D-pSPL3 subclones, designated ium008p004, was derived from a D-pSPL3 library made from the P8 clone (see FIG. 1). A 327 base pair portion of the P1 insert in ium008p004 was sequenced. The protein sequence encoded by this portion of ium008p004 showed homology to two translated sequences in the GenBank nucleic acid database. Two primers were selected from the region of homology and used to amplify a DNA fragment of 90 bp, called P8X1, having the following sequence (SEQ ID NO:46):

```
5' GAGACAAATG  TCCTAGGCTT  CAAGGGACCT  CGGAAGATGA  GTGTGATCGT
   CCCAGGCATG  AACATGGTTC  ATGAGAGAGT  CTGTATCCGC  3'
```

The ium008p004 homologies were to Genbank sequences Z48334 and X69827. Z48334 is the partial sequence of a *Caenorhabditis elegans* cosmid, F10B5. One of the putative genes identified within this sequence contains a 425 amino acid open reading frame, designated F10B5.4 (Wilson R. et al, 1994, Nature 368:32–38). X69827 is a mouse 981 bp partial cDNA with a potential open reading frame of 323 amino acids. This sequence has been shown to have similarity to the family of phosphodiesterase proteins (Vambutas, V. and Wolgemuth, D. J., 1994, Biochim. Biophys. Acta. 1217:203–206).

The above sequence was flanked by consensus splice sites, further demonstrating that the sequence is from an exon, or a coding region, of a gene. The homology to a known gene, as described above, coupled with the presence of consensus splice sites strongly suggested that this region of the ium008p004 clone corresponded to a portion of the coding region of a gene. Given its location within the interval in which the tub gene is located, this putative gene, which was designated CBT9, represented a tub gene candidate.

8.2. Isolation of CBT9 cDNA Clones Materials and Methods cDNA cloning. In order to isolate a longer cDNA of the CBT9 gene, the P8X1 fragment was used as a probe to screen a Stratagene (La Jolla, Calif.) mouse brain cDNA library (#936309). For hybridization, Amersham Rapid Hyb Buffer (Cat. No. RPN1639) was utilized according to manufacturer's protocol. A final washing stringency of was 2×SSC/0.1% SDS at 65° C. was attained and autoradiography was performed overnight. One million clones were screened. Among the clones identified was the fume009 clone, a 1.15 kb cDNA, which was then sequenced.

The fume009 clone was used to screen a mouse hypothalamus cDNA library. This library was constructed from poly-A$^+$ RNA from 6 week old C57BL/6J mice. First and second strand cDNA was made from the poly-A$^+$ RNA using standard procedures. cDNA was ligated into Uni-ZAP XR lambda vector and packaged using a Stratagene kit (Cat. No. 237611). Identical washing conditions as described above were utilized. The screen identified a 6.0 kb clone, designated fumh019, which was sequenced. The fumh019 cDNA clone contains the entire CBT9 gene coding region. The CBT9 sequence is further discussed, below, in the Example presented in Section 12.

Results

In order to isolate CBT9 cDNA clone, the P8X1 fragment was used, as described, above, in the Materials and Methods portion of this section, to screen a mouse brain cDNA library. This screen resulted in the isolation of the fume019 1.15 kb cDNA clone.

The fume019 cDNA clone was then used, as described, above, in the Materials and Methods portion of this section, to screen a mouse hypothalamus cDNA library. This screen resulted in the isolation of a 6.0 kb cDNA clone, designated fumh019.

The fumh019 cDNA clone was sequenced and was determined to contain the entire CBT9 coding region. The CBT9 nucleotide and amino acid sequence are described, below, in the Example presented, below, in Section 12.

9. EXAMPLE: CHARACTERIZATION OF THE EXPRESSION OF THE CBT9 GENE

In the Example presented herein, Northern analysis data is described which characterizes the CBT9 gene (see Section 8, above). Specifically, experiments are presented herein which evaluate the expression of CBT9 in a number of mouse tissues obtained from wild type and tub mice. The results presented herein are consistent with the CBT9 gene being the tub gene.

9.1. Materials and Methods

Northern analysis. The P8X1 DNA fragment and the fume009 cDNA clone were used to probe Northern blots containing total mouse RNA.

Total RNA from tub and wild type (C57BL/6J) mice was isolated and utilized for the Northern analysis. All mice were sacrificed by carbon dioxide asphyxiation. Tissues were dissected on ice, snap-frozen in liquid nitrogen and stored at −80° C. Total RNA was isolated using RNazolB (TelTest, Inc.) The total RNA samples were resuspended in RNase-free DEPC-treated water and quantitated by optical density measurement.

For the Northern blots, long total RNA of each sample was loaded onto a formaldehyde gel. The gel was blotted onto a nylon membrane using standard Northern transfer techniques. The blot: was hybridized with P8X1 which had been radiolabelled by random priming using a Gibco-BRL kit (Cat. No. 18187–013) according the manufacturer's recommended protocol. For hybridization, Amersham Rapid Hyb Buffer (Cat. No. RPN1639) was utilized according to manufacturer's protocol. A final washing stringency of 0.1× SSC/0.1% SDS at 65° C. was attained, and autoradiography was performed overnight.

The Northern blot depicted in FIG. 2 was loaded as follows: lane 1, wild type brain without hypothalamus; lane 2, tub brain without hypothalamus; lane 3, wild type hypothalamus; lane 4, tub hypothalamus; lane 5, wild type heart; lane 6, tub heart; lane 7, wild type lung; lane 8, tub lung; lane 9, wild type liver; lane 10, tub liver; lane 11, wild type kidney; lane 12, tub kidney; lane 13, wild type spleen; lane 14, tub spleen; lane 15, wild type stomach; lane 16, tub stomach; lane 17, wild type muscle; lane 18, tub muscle; lane 19, wild type fat; lane 20, tub fat; lane 21, wild type testis; lane 22, tub testis; lane 23, RNA molecular weight standards, the sizes of which are indicated by the lines at the right hand side of the blot. Specifically, the sizes are 9.49 kb, 7.46 kb, 4.40 kb, 2.37 kb, 1.35 kb and 0.24 kb. The crosses indicate the positions of the 28 S and 18S ribosomal RNA molecules. "Wild type" refers to C57BL/6J mice.

The Northern blot depicted in FIG. 3 was loaded as follows: lane 1, RNA molecular weight standards, the sizes of which are indicated by the lines at the side of the blot (specifically, such sizes are 9.49 kb, 7.46 kb, 4.40 kb, 2.37 kb, 1.35 kb and 0.24 kb); lane 2, wild type brain without hypothalamus; lane 3, tub brain without hypothalamus; lane 4, wild type hypothalamus; lane 5, tub hypothalamus; lane 6, wild type heart; lane 7, tub heart; lane 8, wild type lung; lane 9, tub lung; lane 10, wild type liver; lane 11, tub liver; sane 12, wild type kidney; lane 13, tub kidney; lane 14, wild type spleen; lane 15, tub spleen; lane 16, wild type stomach; lane 17, tub stomach; lane 18, wild type muscle; lane 19, tub muscle; lane 20, wild type fat; lane 21, tub fat; lane 22, wild type testis; lane 23, tub testis. The crosses indicate the positions of the 28S and 18S ribosomal RNA molecules. "Wild type" refers to C57BL/6J mice.

9.2. Results

As shown in FIG. 2, a CBT9 transcript of approximately 7.0 kb is present in the hypothalamus without brain (lane 2) and in the hypothalamus (lane 4) RNA samples derived from the wild type C57BL/6J mice as detected by the P8X1 probe. No CBT9 transcript is detectable in other total RNA samples derived from wild type mouse tissues.

As is further shown in FIG. 2, a CBT9 transcript of approximately 7.5 kb, i.e., approximately 0.5 kb larger than the transcript seen in the wild type tissues, is present in both the brain without hypothalamus (lane 3) and hypothalamus (lane 5) RNA samples derived from the tub mice as detected by the P8X1 probe. No CBT9 transcript is detectable in other samples of total RNA derived from tub mouse tissues.

It should additionally be noted that the abundance of the transcript detected by the P8X1 probe in tub RNA samples is approximately 5-fold greater than it is in RNA samples from wild type (C57BL/6J) mice.

In addition, the fume009 clone was used as a probe to verify the results, described above, which were obtained using the P8X1 fragment as a probe. As shown in FIG. 3, Northern analysis using such a fume009 sequence to probe total RNA from tub and wild type mouse tissue samples yielded the same CBT9 results which were observed using the P8X1 probe. Specifically, a transcript of the same increased size was seen in the total RNA samples derived from tub homozygous mice and the same up regulation was observed in the amount of tub RNA present in total RNA samples derived from tub homozygous animals relative to wild type animals.

A Northern blot analysis of total RNA derived from an animal genotypically shown to be heterozygous for the tub mutation revealed, as expected from the above results, the presence of both the 7.5 kb and 7.0 kb transcripts in total brain RNA. In addition, a moderate up regulation (approximately two-fold) of CBT9 transcript levels relative to CBT9 levels in wild type animals, was observed.

The results of these Northern analyses strongly suggest that a defect within the CBT9 gene results in the tubby phenotype. Specifically, the difference in size observed between the CBT9 transcript in wild type and in tub RNA is consistent with a mutation resulting in the inclusion of exogenous nucleic acid into the tub mRNA. Second, the approximately 5-fold up regulation of CBT9 RNA levels in the RNA samples derived from the tub/tub homozygotes relative to levels observed in RNA samples derived from the wild type mice suggests that such high levels of this transcript are related to the obesity phenotype seen in tubby animals. This may be the result of a negative feedback loop induced by the absence or malfunction of the protein encoded by the mutant tub (CBT9) gene. Third, in total mouse RNA, the CBT9 gene is expressed in the brain, including the hypothalamus, a region of the brain which is known to be involved in the control of body weight (Bray, G. A., 1992, Progress in Brain Res. 93:333–341). Finally, the moderate up regulation seen in the heterozygous animals is consistent with the recessive inheritance pattern of the tubby phenotype, in which heterozygotes are not obese, but, nonetheless, have been shown to exhibit some phenotypic differences relative to homozygous wild type control animals (Nishina, P. M. et al., 1994, Metabolism 43:554–558).

10. EXAMPLE: CBT9 SOUTHERN BLOT ANALYSIS

In the Example presented herein, the results of a Southern blot analysis are described which indicate that homologs of the murine CBT9 gene are present and have been conserved in other mammalian species.

10.1. Material and Methods

Southern blot analysis. Two PCR primers were designed from the CBT9 nucleotide coding sequence, as follows:

P8X9F1 (SEQ ID NO:47): 5'-GGA CAA GAA GGG GAT GGA C-3'

P8X10R1 (SEQ ID NO:48): 5'-CCG TGG ATG ATC TGG AAG T-3'

The primers were used to amplify, via RT-PCR, a 650 bp cDNA fragment (designated P8X9–10) from C57BL/6J mouse whole brain RNA. Standard RT-PCR conditions were utilized. The band was gel-purified and random-prime radiolabelled, as described above.

The resulting probe was hybridized to a Southern blot of EcoRI-digested genomic DNA (BIOS Laboratories; #EBM-100E) from various mammals. Each lane was loaded with 8 µg of digested genomic DNA. For hybridization, Amersham Rapid Hyb Buffer (Cat. No. RPN1639) was utilized according to manufacturer's protocol. A final washing stringency of 0.5×SSC/0.1% SDS at 65° C. was attained, and blots were exposed overnight with an intensifying screen at −80° C.

The lanes of the Southern blot depicted in FIG. 5 were loaded as follows: lane 1, markers: lambda DNA digested with HindIII (band sizes are as indicated in the figure); lane 2, mouse; lane 3, hamster; lane 4, rat; lane 5, rabbit; lane 6, dog; lane 7, cat; lane 8, cow; lane 9, sheep; lane 10, pig; lane 11, marmoset; lane 12, human.

10.2. Results

A Southern blot analysis was conducted using a CBT9 probe (P8X9–10; see Section 10.1 for details) and a DNA blot containing EcoRI-digested mammalian genomic DNA of various species, as described above, in Section 10.1. As is shown in FIG. 5, the CBT9 probe detects homologous sequences in each of the mammalian DNA sample represented on the blot. This result provides additional evidence that the CBT9 sequence used as a probe is part of a gene and, additionally, demonstrates that the sequences show a high level of conservation among a wide range of mammalian species.

11. EXAMPLE: CBT9 IN SITU HYBRIDIZATION ANALYSIS

In the Example presented herein, the results of an in situ hybridization analysis are described which verify that the CBT9 gene is expressed in the brain. Primary CBT9 gene expression occurred within the hippocampus, hypothalamus and cortex. Weaker hybridization could be seen throughout the brain.

11.1. Materials and Methods

In situ Hybridization Localization: Brains from 6 month-old C57 BL/6J mice were removed flash frozen at −80° C. and stored at −80° C. until use. 10 µm frozen sections of brains were post-fixed with 4% PFA/PBS for 15 minutes. After washing with PBS, sections were digested with 1 µg/ml proteinase K at 37° C. for 15 minutes, and again incubated with 4% PFA/PBS for 10 minutes. Sections were then washed with PBS, incubated with 0.2N HCl for 10 minutes, washed with PBS, incubated with 0.25% acetic anhydride/1M triethanolamine for 10 minutes, washed with PBS and dehydrated with 70% ethanol and 100% ethanol. Hybridizations were performed with $^{35}$S-radiolabelled (5×10$^7$ cpm/ml) cRNA probes encoding a 1.15 kb segment of the coding region of the mouse clone fume009 in the presence of 50% formamide, 10% dextran sulfate, 1×Denhardt's solution, 600 mM NaCl, 10 mM DTT, 0.25% SDS and 100 µg/ml tRNA for 18 hours at 55° C. After hybridization, slides were washed with 5×SSC at 55° C., 50% formamide/2×SSC at 55° C. for 30 minutes, 10 mM Tris- HCl(pH 7.6)/500 mM NaCl/1 mM EDTA (TNE) at 37° C. for 10 minutes, incubated in 10 µg/ml RNase A in TNE at 37° C. for 30 minutes, washed in TNE at 37° C. for 10 minutes, incubated once in 2×SSC at 50° C. for 30 minutes, twice in 0.2×SSC at 50° C. for 30 minutes, and dehydrated with 70% ethanol and 100% ethanol. Localization of mRNA transcripts was detected by film emulsion autoradiography followed by dipping slides in photo-emulsion for precise autoradiographic localization.

11.2. RESULTS

The fume009 cDNA clone was used as a probe for an in situ hybridization analysis. Specifically, the 1.15 kb fume009 probe was hybridized to sections of wild type C57BL/6J mice. As shown in FIG. 5, the CBT9 transcript is expressed in the hypothalamus and other regions of the brain, consistent with the above-described Northern analysis data, which was presented in Section 9, above.

Specifically, an mRNA transcript hybridizing to the 1.15 kB fume009 antisense cRNA probe was localized to discrete regions of the brain of both C57BL/6J wild type mice (FIG. 5) and tub homozygous mice. Signal was observed in the hypothalamus adjacent to the 3rd ventricle in two "nuclear bodies" (indicated by dense clustering of nuclei) as well as at the base of the hypothalamus adjacent to the optic chiasm in the tissue from both mice. Thus, expression in the hypothalamus is highest in the paraventricular, ventromedial and arcuate nuclei.

In addition, signal was detected in scattered cells in the subcortical temporal lobe and in hippocampus in the tissue sections from both mice. FIG. 5 shows the regions of localization of tub gene transcript in the brain of C57BL/6J mice (the arrows indicate those regions where signal was detected). Weaker hybridization was observed throughout the brain. No distinct signal was observed in heart, spleen, liver, lung, skeletal muscle, pancreas, small intestine and stomach of either the C57 BL/6J wild type mice or tub homozygous mice.

12. EXAMPLE: IDENTIFICATION OF CBT9 AS THE tub GENE

Presented in this Example is, first, a mutational analysis) of the CBT9 gene, which compares CBT9 gene sequences within nucleic acid derived from wild type and tub animals. Specifically, a CBT9 splice site mutation is identified within tub genomic DNA which is absent from wild type genomic DNA. Second, the nucleotide and derived amino acid sequence of the CBT9 gene is presented. The results disclosed herein, coupled with the results presented, above, in Sections 6 to 11, identify the CBT9 gene to be the tub gene.

12.1. Materials and Methods

PCR, analysis. A number of primers were designed to amplify the entire open reading frame of CBT9 from tub and wild type mice in order to identify the location of the mutation in the tub gene. The following two primers amplified different sized cDNA fragments when amplifying tub-derived versus wild type-derived nucleic acid:

PX1R (SEQ ID NO:49): 5'-TGA GAC AAA TGT CCT AGG CT-3' (corresponding to CBT9 base pair 1113 to 1132);

PX12R (SEQ ID NO:50): 5'-TGG ACA GAG CAA TGG CGA AG-3' (corresponding to CBT9 base pair 1489 to 1470)

Standard PCR conditions and sequencing procedures were utilized.

12.2. Results

12.2.1. CBT9 Mutational Analysis

In order to more definitively show that the CBT9 gene corresponded to the tub gene, a PCR study was conducted to define the mutation causing the CBT9 transcript size change observed in tub mice relative to the CBT9 transcript size observed in RNA of wild type mice. Of the PCR primer pairs utilized, only one resulted in a size differential between the fragment amplified using tub-derived nucleic acid and the fragment amplified using wild type-derived nucleic acid (see Section 10.1 for details).

Specifically, utilizing this primer pair (i.e., PX1R and PX12R) a cDNA was amplified from wild type (C57BL/6J) brain RNA which was about 350 bp, while a cDNA fragment was amplified from tub brain RNA which was about 800 bp. The amplification of both wild type (C57BL/6J) and tub genomic DNA resulted in a band of approximately 900 bp.

It should be noted that the size differential, approximately 450 bp, between the tub and wild type cDNA amplified fragments roughly corresponds to the difference in transcript size (i.e., 7 vs. 7.5 kb) observed between tub and wild type RNA in the CBT9 Northern analysis described, above, in the Example presented in Section 9. By sequencing (see below) it was determined that the precise size difference between the tub and wild type cDNA amplified sequences was 398 bp.

The 900 bp fragment amplified from genomic DNA reveals the presence of a second intron within the amplified region. Only one of these introns (of approximately 100 bp in length) was processed correctly in the tub animals, as discussed below.

The cDNA and genomic amplified fragments in the region of the mutation were sequenced and the wild type- and tub-derived sequences were aligned, as shown in FIGS. 7A–7D. For orientation of the genomic sequence depicted in FIGS. 7A–7D with the full length CBT9 cDNA coding sequence shown in FIGS. 6A–6D, bases 1–12 and 411–437 in FIGS. 7A–7D correspond to bases 1373–1384 and 1385–1411 of FIGS. 6A–6D. In FIGS. 7A–7D, the two top sequences are from genomic DNA derived from tub and wild type C57BL/6J mice, as indicated. The bottom two sequences are derived from cDNA from tub and wild type mice, as indicated. The vertical arrow shows the position of the tub mutation. The horizontal box indicates the consensus splice site sequence in C57BL/6J which is abolished in the tub genomic DNA. The asterisks indicate the intron which is erroneously not spliced out of the mature tub mRNA.

The portion of the CBT9 gene sequence in FIGS. 7A–7D depicts only the genomic region near the mutation site. This alignment revealed a single base pair difference of a G to T transversion in the first base of the splice site (GTGACT; see boxed region of FIG. 1) of the intron between base 1384 and 1385 of the open reading frame of the genomic DNA. This mutation abolishes the splice site, resulting in retention of an intron of approximately 450 bp in the amplified cDNA derived from the tub RNA. To confirm that the identified sequence change did not simply represent a polymorphism, the splice site was sequenced in 32 additional mouse strains. In each of the strains, the DNA sequence at the putative mutation site was identical to that observed in the wild type C57BL/6J strain.

FIG. 8 depicts a schematic representation of the splicing defect within the CBT9 in tub mice. The top half of the figure shows the normal, wild type splicing of the intron from C57BL/6J RNA and the predicted carboxy terminus of the wild type CBT9 protein. The G to T mutation of the first base of the intron within the CBT9 gene in tub mice abolishes splicing of this intron, causing the intron to be retained within the mature mRNA. The predicted tub mutant CBT9 protein, therefore, is abnormal. Specifically, due to translation of intronic sequence, this mutant tub gene product lacks the final 44 amino acid residues of the normal CBT9 protein and, instead, contains 24 intron-encoded amino acid residues at its carboxy terminus which are erroneously added to the tub protein until a stop codon within the intronic sequence is reached.

12.2.2. CBT9 Nucleotide and Amino Acid Sequence

As discussed in Section 8.2, above, the fumh019 CBT9 cDNA clone was sequenced. Sequencing revealed that the fumh019 cDNA clone contained the entire CBT9 open reading frame.

The nucleotide sequence and amino acid sequence of CBT9 is shown in FIGS. 6A–6D. The CBT9-encoded protein is 505 amino acid residues in length. CBT9 is a novel gene, with no identical sequences present in published databases. The entire CBT9 coding region of the Mus spretus and A/J mouse strains were sequenced and no non-conservative amino acid changes in either strain as compared to the C57BL/6J tub sequence were found.

The CBT9 gene product is a hydrophilic protein, with an estimated pI of 9.2, which lacks any obvious secretary sequence, mitochondrial transit peptide or transmembrane domain. The gene product contains a region consisting of two runs of serine amino acid residues separated by eight acidic amino acid residues (amino acid residues 191–211), which could serve as a hinge between domains of the protein. In addition, two potential dibasic protease cleavage sites are present at amino acid positions 302 and 383, and two potential glycosylation sites are present at amino acid positions 205 and 426.

The carboxy half of the CBT9 gene product shows similarity to several sequences in the public protein databases and/or encoded by sequences present in public nucleotide databases, including p4–6, a mouse testis cDNA (Genbank X69827); F10B5.4 (Genbank Z48334), a *C. elegans* genomic sequence; DM87D3S (Genbank Z50688) a Drosophila STS; and ys86c0.4.r1 (Genbank H92408), a human retinal cDNA; as well as several rice, maize and Arabidopsis ESTs. With the exception of the mouse testis cDNA p4–6, none of these sequences has been functionally characterized. p4–6 was isolated by screening of a cDNA library with a rat phosphodiesterase probe (Vambutas, V. & Wolgemuth, D. J. 1994, Biochim. Biophys. Acta 1217:203–206).

Upon alignment of the CBT9 gene product and the sequences showing similarity to CBT9, certain regions were shown to be completely conserved. Specifically, the two dibasic protease cleavage amino acid residues and the cysteine amino acid at the penultimate CBT9 position are all completely conserved among all the CBT9-related sequences.

The data presented in Sections 6 to 11 above, including mapping data, and Northern and in situ analyses, and the mutational analysis data presented in this Section demonstrating that the tubby phenotype is associated with a splicing defect within the CBT9 gene which results in a major alteration of the carboxy terminus of the CBT9 gene product, represent conclusive evidence that the CBT9 gene is the tub gene. Specifically, CBT9 maps within the 0.25 cM interval that the tub gene has been shown, herein, to map. Further, the CBT9 gene is expressed in the brain, including the hypothalamus, a region known to be involved in body weight control. Additionally, the CBT9 transcript in tub animals is larger than the CBT9 transcript found in wild type C57BL/6J animals and it has been shown herein that this increase in size is due to a single base mutation in a CBT9 splice site which results in the incorrect splicing of the RNA such that a 398 nucleotide intron remains within the mature mRNA. As a result, the protein which is translated from such a mutant transcript exhibits an abnormal carboxy terminus. Presumably as a result of this defect, the CBT9 mRNA is upregulated approximately 5-fold in homozygous tub/tub mice. The heterozygous tub/+ mice showed a more modest upregulation, as would be expected, given the heterozygous tub phenotype. In summary, therefore, the CBT9 gene has successfully been identified to be the tub gene.

13. EXAMPLE: CLONING AND CHARACTERIZATION OF THE HUMAN tub GENE

The Example presented herein describes the successful cloning and characterization of the human tub gene, which is involved in the control of human body weight. Both the human tub gene and gene product exhibit a striking level of similarity to the murine tub gene and gene product.

13.1. Materials and Methods

P8X5-1 tub probe generation: The 950 base pair P8X5-1 tub gene cDNA probe was generated by standard PCR amplification of the murine cDNA clone fumh019, described, above, in Section 8. The following primers were utilized for the amplification:

P8X5R1 (SEQ ID NO:51): 5'-CCG ACT CGA TTG CCA GTG TA -3'

P8X1F1 (SEQ ID NO:52): 5'-GCG GAT ACA GAC TCT CTC AT -3'

Upon amplification, the probe was gel purified and radiolabelled according to standard protocols.

cDNA screening: Screening was performed on a human fetal brain cDNA library (Clontech #HL1149x). Hybridization was performed for 4 hours at 65° C. using Amersham Rapid Hyb buffer (Cat. #RPN1639) according to the manufacturer's protocol. A final washing stringency of 1.0×SSC/ 0.1% SDS at 50° C. for 20 minutes was achieved. Autoradiography was performed overnight.

DNA sequencing: Standard DNA sequencing techniques were utilized for the sequencing of the resulting putative human tub cDNA clones.

13.2. Results

The 950 base pair P8X5-1 murine tub gene probe, described, above, in Section 13.1, was used to screen a human fetal brain cDNA library for clones corresponding to the human tub gene. Screening conditions were as described, above, in Section 13.1.

Screening of the human cDNA library yielded thirteen independent positive clones. Among these clones were those designated CBT9H1, CBT9H2 and CBT9H3, which have been deposited with the ATCC. Sequencing revealed that the entire coding region of the human tub gene was contained within these partially overlapping clones.

The nucleotide and derived amino acid sequences of the human tub gene are shown in FIGS. 9A–9D . As shown in FIGS. 9A–9D, the human tub gene encodes a 506 amino acid protein. The human tub gene product encodes a hydrophilic protein exhibiting an estimated pI of 9.2 which lacks any obvious secretory sequence, mitochondrial transit peptide or transmembrane domain. The gene product contains a region consisting of two runs of serine amino acid residues separated by a acidic amino acid residues (amino acid 191–211) which could serve as a hinge between domains of the protein. In addition, there are two potential dibasic protease cleavage sites at amino acid positions 301–306 and 381–384, as well as two potential N-glycosylation sites at amino acid residues 206 and 427.

The human tub gene and gene product exhibit a striking similarity to the murine tub gene and gene product. Specifically, the human tub gene is 89% identical, at the nucleotide level, to the murine tub gene. Further, the 506 amino acid human tub gene product exhibits a 94% identity to the 505 amino acid murine tub gene product. Amino acid residue 201 represents the only amino acid insertion between the two tub gene product sequences. Specifically, the human tub amino acid residue 201 corresponds to an insertion between murine amino acid residues 200 and 201. The carboxy half of the tub gene product is particularly highly conserved. The final 260 amino acid residues of the human and mouse tub gene products differ by only a single residue. Specifically, murine tub gene product amino acid residue 399 is a cysteine, while the corresponding human tub gene product amino acid residue 400 is serine.

In summary, the results presented herein represent the successful cloning of the human tub gene.

14. EXAMPLE: HUMAN AND MURINE tub GENE ALTERNATIVE SPLICING

The Example presented herein describes the discovery that both the human and murine tub genes produce alternatively spliced transcripts. Specifically, it is shown that tub transcripts are produced which either contain or are lacking the sequence corresponding to tub exon 5. Quantitative variation between the relative amounts of alternatively spliced species produced is also described.

14.1. Material and Methods

RT-PCR. First strand cDNA was synthesized from total RNA using SuperScript (Gibco-BRL) according to supplier's protocol. Subsequent PCR conditions were as follows: Hot start with 0.5 U AmpliTaq, followed by 30 cycles at 94° C. for 1 minute, 55° C. for 1 minute and 72° C. for 1 minute. Products were electrophoresed on 2% agarose gels. RT-PCR products to be sequenced were run on LMP agarose, excised, digested with β-Agarase (New England Biolabs), precipitated and resuspended in water. The same conditions were utilized for amplification of both human and mouse RNA populations.

The primers utilized for mouse sequence amplification were derived from murine tub exons 4 and 6: P8X5 R (SEQ ID NO:53): 5'-CCG ACT CGA TTG CCA GTG TA -3'; and CBT9R5 (SEQ ID NO:54): 5'-GGA GCT GTT TTC ATC CTC ATC -3'.

The primers utilized for human sequence amplification were derived from human tub exons 4 and 6: hCBT9F11 (SEQ ID NO:55): 5'-GAA GGA GAA GAA GGG AAA GC-3'; and hCBT9R11 (SEQ ID NO:56): 5'-GGG TGT TAC TAT TTA GCT GG-3'.

Other techniques. All other techniques were performed according to standard procedures and/or as described in the Examples presented above. Primers used for genomic PCR amplification were derived from tub exons 4 and 5: X4F1 (SEQ ID NO:57): 5'-TTC AAG AGG CCG ACT CGA TT -3'; and X5R1 (SEQ ID NO: 58): 5'-TTC CTC TGC ATC GTG GCA C -3'.

14.2. Results

RT-PCR from mouse brain RNA using primers derived from exons 4 and 6, as described in Section 14.1, above, resulted in the amplification of two products. Sequencing of these products showed that they differ by the presence or absence of sequence corresponding to exon 5. RT-PCR of RNA from C57BL/6J mice consistently yielded more of the amplified product containing exon 5. This result was shown to be true for 7 other strains tested.

RT-PCR performed using brain RNA derived from the Mus spretus strain, however, invariably showed a greater abundance of the product lacking exon 5. This was demonstrated in 6 independent M. spretus mice. This quantitative pattern was also found to be exhibited in M. castaneous mice. Genomic PCR revealed that the intron preceding exon 5 was 0.5 kb shorter in both M. spretus and M. castaneous strains. Sequencing of a portion of this intron showed that its donor, acceptor and branch point sequences were not affected by the sequence missing in these strains.

RT-PCR of total human RNA from several tissues was performed with two primers from exons 4 and 6 using the same conditions as for mouse RNA. The amplification primers were hCBT9F11 and hCBT9R11, as described, above, in Section 14.1. Amplification produced two amplified fragments of 281 bp and 113 bp. Sequencing revealed that the larger band represented a transcript containing exon 5, while the smaller fragment was missing the sequence corresponding to exon 5. Thus, the human tub gene, also exhibits alternate splicing of exon 5. Both the human and mouse exon 5 is 168 base pairs long. Because this length is a multiple of 3, the reading frame of the transcripts lacking exon 5 is conserved.

It is possible that variant splicing may result in proteins with qualitatively or quantitatively distinct activities. The differential regulation of alternate splicing may result in individuals with differential susceptibilities to obesity. For example, in place of the constitutive obesity associated with the tub mutation, alleles which yield a higher amount of protein encoded by transcripts lacking exon 5 relative to the level encoded by transcripts containing exon 5 may confer a greater susceptibility to obesity only in the context of a particular environmental and genetic background.

15. EXAMPLE: RECOMBINANT EXPRESSION OF tub GENE PRODUCTS

The Example presented in this Section describes the recombinant expression of murine and human tub gene products.

15.1. Materials and Methods

Bacterial expression

Murine tub subcloning. cDNA sequence containing the entire murine tub coding region was subcloned into bacterial expression vector pET29*. pET29* is a modified pET29a vector (Novagen, Inc., Madison Wis.) containing an altered Shine-Dalgarno sequence for optimal initiation of translation (Chen, H. et al., 1994, Nuc. Acids Res. 22:4953–4957).

In order to subclone the tub coding sequence into the pET29* vector, site directed mutagenesis was performed on an existing tub cDNA to create a tub sequence with appropriate restriction sites. Specifically, single stranded DNA was rescued from CJ 236 E. coli transformed with pMal-c2 (New England Biolabs, Beverley Mass.) plasmid containing a PCR-derived tub cDNA by infection with K07 M13 helper phage. The single stranded DNA was used as a template for site directed mutagenesis which yielded amplified tub fragments containing altered ends (Kunkel, T. A., 1985, Proc. Natl. Acad. Sci. USA 82:488–491). The 5' end of the amplified fragment was altered such that the tub initiation codon was contained within an NdeI site (i.e., CATATG), while the 3' end was altered such that part of the tub termination codon was contained within an EcoRI site (i.e., TGAATTC) The resulting tub cDNA was excised as a 5' NdeI to 3' EcoRI fragment and ligated into NdeI/EcoRI-digested pET29* vector, to yield the murine pET29*-tub expression construct.

In order to produce the murine tub-HIS$_6$ expression construct, codons for six histidine residues were fused in-frame at the 3' end of the tub cDNA sequence. Site directed mutagenesis was employed as described above, except that the primers utilized yielded fragments containing the six histidine codons inserted just 5' of the EcoRI site at the 3' end of the cDNA (i.e., CACCACCACCACCACCACTGAATTC) (SEQ ID NO:59). The resulting mutagenized fragment was excised and ligated into pET29* as described above to yield the murine pET29*-tub-HIS$_6$ expression construct.

Human tub subcloning. The entire coding region of the human tub sequence was also inserted into the pET29* expression vector in both native and HIS$_6$ fusion forms. For insertion into pET29*, a human tub cDNA in pMal-C2 was modified via site directed mutagenesis to create 5' NdeI and 3' EcoRI restriction sites, as described for the murine tub sequence, above, to yield the human pET29*-tub expression construct.

For construction of the human tub HIS$_6$ construct, six histidine codons were introduced just 5' of the EcoRI site by a three part ligation. Specifically, a 5' ApaLI-3' EcoRI restriction fragment encoding the last 25 amino acids of the murine pET29*-tub-HIS$_6$ was exchanged for the equivalent fragment of the human tub gene sequence in human pET29*-tub construct, to yield the human pET29*-tub-HIS$_6$ expression construct. It should be noted that, although the human and mouse tub genes have differing primary sequences, the amino acid residues they encode within this carboxy-terminal region are identical.

Expression of recombinant tub proteins. Host bacteria BL21(DE3) (Novagen, Inc., Madison Wis.) were chemically transformed with each of the expression constructs described above (i.e., murine pET29*-tub, murine pET29*-tub-HIS$_6$, human pET29*-tub or human pET29*-tub-HIS$_6$) and grown in 6 liters BHI (Brain Heart Infusion broth) cultures to mid-log phase (OD$_{595}$=1.0) at 37° C.

T7 RNA polymerase and, concomitantly, tub protein expression, was induced by the addition of IPTG to a final concentration of 0.5 mM. Two hours post-induction, bacteria were collected by centrifugation and frozen.

Mammalian expression

Murine tub subcloning. To prepare murine tub cDNA containing the entire tub coding region, the 5' end of the murine tub cDNA in the murine pET29*-tub construct was mutagenized to remove the NdeI restriction site, and replaced with a BamHI restriction site and a Kozak box (Kozak, M. 1987, Nuc. Acid Res. 15:8125–8132) for efficient initiation of translation in mammalian cells. After modification, the sequence just 5' of the tub start codon was as follows: GGATCCACCATG (SEQ ID NO:82) (the start codon is underlined).

The modified sequence was digested with BamHI and EcoRI to excise the region to be subcloned. After excision, the murine tub cDNA was ligated into the transient expression vector pN8ε (to yield the pN8ε-tub construct) and into the stable retroviral expression vector pWZLblast (to yield the pWZLblast-tub construct). Transcription in pN8ε is directed from the human CMV immediate early promoter, while transcription from pWZLblast is initiated in the promoter embedded Moloney Leukemia Virus LTR.

Constructs for the expression of epitope tagged recombinant tub gene product were generated, in which a DNA fragment encoding three tandem copies of the influenza virus hemagglutinin peptide YPYDVPDYA was fused in-frame with the NH$_2$ terminus of the tub cDNA in pN8ε-tub. Specifically, the triple flu epitope was amplified from the plasmid pBS HA$^3$ via PCR with primers possessing 5' HindIII and 3' BamHI restriction sites. The PCR product was purified, HindIII/BamHI digested and ligated into HindIII/BamHI digested pN8ε-tub. The correct sequence of the fusion construct (designated pN8ε3Xflu-tub) was verified.

Expression of recombinant tub proteins. Transient expression is achieved by transfection of pN8ε-tub or pN8ε3Xflu-tub expression constructs into 293 EBNA cells (Invitrogen Corp.) via lipofection (Lipofectamine; Life Technologies Corp.). Analyses performed 72 hours post-lipofection.

Stably infected polyclonal pools of NIH 3T3 cells harboring pWLZblast-tub proviruses are generated by transiently transfecting ΩE producer cells (Morgenstern, J. P. & Land, H., 1990, Nuc. Acids Res. 18:3587–3596) with calcium phosphate and harvesting recombinant retrovirus 48 hours later. The virus is then used to infect target NIH 3T3 fibroblasts overnight at which time the infected cells are split 1:10 into medium supplemented with blasticidin HCl (ICN Corp.) at a concentration of 10 μg/ml. Colonies of blasticidinS HCl-resistant cells which appear within roughly two week, are pooled and lysed for analysis.

15.2. Results

Described herein is the successful expression of recombinant murine and human tub gene products in mammalian and/or bacterial systems. With respect to bacterial expression, both native and HIS$_6$ fusion (i.e., a fusion protein containing six carboxy-terminal histidine amino acid residues following the native tub amino acid sequence) tub gene products have been expressed. Details regarding the creation of tub expression constructs and production of gene products using these constructs are described, above, in Section 15.1.

Aliquots of bacterial lysates (representing approximately 10$^{-5}$ of the total 6 liter preparation were analyzed using standard SDS polyacrylamide gel electrophoresis, as depicted in FIG. 11. A protein with a molecular weight of approximately 57 kD was readily apparent in proteins obtained from induced bacteria containing murine pET29*-tub. 57 kD was the approximate molecular weight one would predict for the murine tub protein, with its 505 amino acid residues. Likewise, a protein with a molecular weight of approximately 57 kD was readily apparent in proteins obtained from induced bacteria containing human pET29*-tub. 57 kD was the approximate molecular weight one would predict for the 506 amino acid residue human tub gene product.

A protein exhibiting a slightly increased molecular weight was readily apparent in proteins obtained from induced bacteria containing either human or murine pET29*-HIS$_6$. The slight increase in molecular weight was expected given the additional six histidine residues present in these tub-HIS$_6$ fusion proteins.

Constructs for the expression of epitope-tagged murine tub protein were utilized to demonstrate successful mammalian expression of recombinant tub gene product. Specifically, the pN8ε3Xflu-tub expression construct was introduced, via lipofection, into 293 EBNA cells, as described, above, in Section 15.1. After lipofection, immunoprecipitation followed by Western blot detection with the monoclonal antibody 12CA5 (directed against the flu hemagglutinin peptide; Boehringer Mannhein Corp.) was performed. Western blotting revealed the presence of a protein exhibiting a molecular weight of approximately 59 kD (i.e., a size expected of the full length tub gene product fused the triple flu hemagglutinin peptide sequence). No such protein was detected in control transfections with non-hemagglutinin tagged pN8ε-tub constructs.

In summary, the results described herein indicate that recombinant murine and human tub gene products have successfully been expressed in bacterial and/or mammalian systems.

16. EXAMPLE: IDENTIFICATION AND CHARACTERIZATION OF A tub GENE HOMOLOG

The Example presented in this Section describes the identification and characterization of a human tub gene homolog, referred to herein as human tub homolog 1.

The mouse tub gene nucleotide sequence was utilized as a database query using the Blastx program (1993, Nature Genetics 3:266–272), which resulted in the identification of a human EST (GenBank Accession No. H92408) which exhibited a 75.3% identity over 85 derived amino acid residues. The EST was originally derived from a human retinal library (Soares, B. and Benaldo, F.).

Upon identification of the EST, the corresponding clone was obtained from Genbank and sequenced. A number of errors in the sequence listed in the database were found. These included a deletion of bp 33 from the Genbank sequence, incorrect base pair insertions (Genbank sequence bps 330, 339, 359, 366, 375 and 384), incorrect sequence at bps 133–137 (ACCGA in Genbank sequence, as opposed to the correct GGCCG sequence) and incorrect bp 398 (T in Genbank as opposed to the correct G).

The identified sequence was used to screen a retinal cDNA library, which resulted in the identification of several positive clones. FIGS. 12A–12C depicts nucleotide sequence of the tub homolog identified via this screening effort, which is referred to herein as human tub homolog 1. The sequence depicted in FIGS. 12A–12C codes for a substantial portion of the human tub homolog 1 protein, the derived amino acid sequence of which is also depicted in FIGS. 12A–12C. The sequence exhibits a 73.9% identity over 216 derived amino acid residues.

The EST derived from the human tub homolog 1 gene was mapped in the human by PCR typing of the Genebridge (G4) radiation hybridization panel. Typing of the DNA and comparison to radiation hybrid map data at the Whitehead Institute Center for Genome Research (WICGR) tightly linked the EST to an anonymous STS, WI-4186, on human chromosome 6.

Additionally, the EST was genetically mapped in the mouse using a C57BL/6J ×Mus spretus interspecific backcross. Genotyping of 100 meioses demonstrated linkage to a region on mouse chromosome 17 between D17Mit48 and D7Mit 9.

Human multiple tissue northern blots (Cat. No. 7766-1 and 7760-1; Clonetech, Palo Alto Calif.) containing 2 μg of poly A+ RNA per lane were probed with the approximately 1.35 kb EcoRI-NotI fragment of the sequence obtained from Genbank containing the human tub homolog 1 insert. The filters were prehybridized in 5 mls of Church buffer at 65° C. for 1 hour, after which 100 ng of $^{32}$P-labelled probe was added. Probe was made using Stratagene Prime-It kit (Cat. No. 300392; Stratagene, La Jolla Calif.). Hybridization was allowed to proceed at 65° C. for approximately 18 hours. Final washes of the filters was in 0.1% SDS, 0.2×SSC solution for 65° C. Washed filters were exposed to a phosphoimager for 4 hours.

The Northern analysis was performed using a 1.35 kb probe as described in Section 16.1, above, containing human tub homolog 1 sequence encoding 285 amino acids plus 3'-untranslated sequence to the poly-A sequence was performed. Tissues tested included brain, lung, liver, kidney, spleen, thymus, muscle, prostate, testis and fat. A message of approximately 2 kb was apparent in the lanes containing RNA from skeletal muscle and testis.

17. CHARACTERIZATION OF THE REGULATION OF tub GENE PRODUCT ACTIVITY IN RESPONSE TO INSULIN The Example presented herein describes the discovery that tub gene product is a substrate for receptor protein-tyrosine kinases. Specifically, in response to insulin stimulation, the tub gene product becomes a substrate for protein-tyrosine kinases and interacts with SH2 containing signaling proteins.

17.1. Materials and Methods

Cell culture

CHO-IR cells, stably expressing the wild type human insulin receptor (approximately 80000 receptors/cell), were grown in RPMI supplemented with 10% FCS and 400 μg/ml G418 (Gibco BRL, Gaithersburb Md.) (White et al, 1987, J. Biol. Chem. 262:9769–9777). 3T3-IR cells, stably expressing the wild type human insulin receptor, were grown in DMEM supplemented with 10% FCS and 200 μg/ml G418 (Gibco BRL, Gaithersburb Md.).

Antibodies

Anti-tub gene product antibody is a rabbit polyclonal, raised against full length His6-tagged wild type tub gene product; Anti-HA antibody is a mouse monoclonal (clone 12CA5), (Boehringer Mannheim, Indianapolis, Ind.); Anti-phosphotyrosine antibody is a mouse monoclonal (clone RC20H) (Transduction Laboratories, Lexington, Ky.) or (clone 4G10) (Upstate Biotechnology Inc., Lake Placid, N.Y.); Anti-PLCγ1 is a mouse monoclonal (Clone 10) (Transduction Laboratories, Lexington, Ky.) or rabbit polyclonal (Santa Cruz Biotechnology, Santa Cruz, Calif.).

Plasmids and cDNAs:cDNAs

The mouse wild type-tub cDNA was amplified by PCR from mouse brain total cDNA library. In order to enhance the translation efficiency of the cDNA, site directed mutagenesis was used to place a "Kozak" translation initiation consensus motif at the ATG of the cDNA (GGATCCACCATG). In addition to the mutation, for ease of subcloning, an EcoR I site was introduced just 3' of the cDNA's termination codon.

The mutant Mouse tub cDNA was assembled by swapping an Eag I to EcoR I restriction site at the 3' end of the above wild type tub cDNA with an analogous restriction fragment from a partial mutant tub cDNA. PCR was carried out on tub mouse total brain cDNA to amplify a partial cDNA comprising the 3' end of the mutant tub cDNA (commencing 5' at the Eag I site of both mutant and wild type tub and proceeding to the termination codon of mutant tub, with an EcoR I site introduced at the 3' end of the cDNA for convenience of subcloning). The partial cDNA was subcloned, and its sequence verified. At this point the carboxy terminus of wild type tub was exchanged for that of mutant tub by the aforementioned swapping of 5'-Eag I to EcoR I-3' restriction fragments.

Expression Plasmids cDNA isolated from both the wild type and mutant tubby mice were respectively introduced as 5'-Bam HI>EcoR I-3' restriction fragments into the pN8ε transient expression vector.

To aid in the detection of the tub gene product during transfections, both the wild type and mutant tub cDNA were respectively introduced as 5'-Bam HI>EcoR I-3' restriction fragments into the pN8ε 3xHA. transient expression vector. This variant of the pN8ε vector fuses 3 consecutive flu hemagglutinin HA epitopes (YPYDVPDYA) (SEQ ID NO:60) in frame with the $NH_2$-termini of the proteins. The resultant proteins are referred to HA-tub or Mut-tub.

In order to visualize the subcellular localization of the tub gene product during transfections, both the wild type and mutant tub cDNAs were respectively introduced as 5'-Bam HI>EcoR I-3' restriction fragments into the pN8ε KGFP transient expression vector. This variant of the PN8ε vector fuses a modified green fluorescent protein (GFP) cDNA in frame with the $NH_2$-termini of the proteins. The resultant proteins are referred to as GFP-WT-tub or GFP-Mut-tub.

To assess the nature of tyrosine phosphorylation of the tub gene product in cells stimulated by growth factors, series of phenylalanine (F) residues were substituted for the native tyrosine (Y) residues within the protein. All tyrosine to phenylalanine substitutions were carried out by site directed mutagenesis (Kunkel, 1985, Proc. Natl. Acad. Sci. USA 82:488–492) on the pN8ε HA-tub expression vector. Initially, three carboxy terminal tyrosine (Y) residues were replaced with phenylalamine (F): $Y_{483}$, $Y_{481}$, and $Y_{464}$ (referred to as HA-tub Y3>F).

GST-SH2 Fusion Proteins

1—p85 (PI 3-kinase regulatory subunit) N-terminal and C-terminal SH2 domains (Kapeller et al., 1995 J. Biol. Chem. 270:25985–25991; Yoakim et al., 1992 J. Virol 66:5485–5491)

2—PLCγ1 N-terminal and C-terminal SH2 domains (Anderson et al., 1990 Science 250:979–982)

3—Grb2-SH2) (Lowenstein et al., 1992 Cell 70:431–442; Rozakis-Adcock et al., 1992 Nature 360:689–692; Skolnik et al. 1993 (Science 260:1953–1955)

4—Lck-SH2 (Prasad et al., 1993 Mol. Cell. Biol. 13:7708–7717; Reynolds et al., 1992 Oncogene 7:1949–1955)

5—Abl-SH2 (Mayer et al., 1991 Proc. Natl. Acad. Sci. USA 88:627–631; Zhu et al., 1993 J. Biol. Chem. 268:1775–1779)

6—Src-SH2 (Anderson et al., 1990 Science 250:979–982; Waksman et al., 1992 Nature 358:646–653)

*E. coli* DH5α were transformed with plasmids containing the above GST-SH2 fusion proteins. Cells were grown in LB urea broth induced with IPTG (0.5 mM) and lysed as described (Ausubel et al., 1991 Current Protocols in Molecular Biology, Greene Publishing Assoc. and Wiley-Neuroscience). The GST fusion proteins were purified on GSH- sepharose beads as suggested by Pharmacia Biotech (Piscataway, N.J.)

Transfection, Immunoprecipitation/GST-SH2 precipitation and Immunoblotting

The CHO-IR cells were split 1:5 into 100 mm plates (10 ml RPMI/10% FCS) 24 hrs prior to transfection. The lipofectamine method was used to transfect CHO-IR cells with either empty pN8ε vector or pN8ε containing the different HA-tagged forms of tub (8 μg DNA/transfection) as indicated in each experiment. The media was replaced 24 hours post-transfection with serum-free RPMI and the cells were maintained in serum-free media for at least 16 hours. Following stimulation with the indicated growth factors, the cells were washed twice in ice cold PBS and incubated for 10 min with rocking at 4° C., with 100 μl lysis buffer (20 mM Hepes, pH 7.5, 0.3M NaCl, 0.2 mM EDTA, 1.5 mM MgCl12, 1 mM DTT, 1 mM Na vanadate, 10 mM NaF, 10% glycerol, 1% Triton X-100, 1 mM PMSF and 1 μg/ml of leupeptin, pepstatin and aprotinin). The plates were further incubated with 300 μl equilibration buffer (20 mM Hepes, pH 7.5, 0.2 mM EDTA, 2.5 mM MgCl2, 1 mM DTT, 1 mM Na vanadate, 10 mM NaF, 10% glycerol, 0.5% Triton X-100, 1 mM PMSF and 1 μg/ml of leupeptin, pepstatin and aprotinin), with 10 min rocking at 4° C. The lysates were placed into eppendorf tubes followed by high speed centrifugation. A 60 μl aliquot was taken from the cleared whole cell lysate (WCL) and mixed with 20 μl 4xloading buffer and placed at 20° C. until further use. The remainder of the lysate was then incubated for 2 hrs, rocking at 4° C., with either anti-HA (10 μl; 12CA5,), anti-tub (5 μl; polyclonal, raised against recombinant His-tagged wt-tub) or anti-phosphotyrosine (5 μl clone; 4G1O, Upstate Biotechnology Inc., Lake Placid, N.Y.) in the presence of protein A-sepharose beads (Pharmacia, Columbia, Md.), as indicated. Alternatively, the lysates were incubated with 5 μg of GSH-sepharose bound GST or GST-SH2 fusion proteins. The precipitates were then washed three times with High salt wash buffer (20 mM Hepes, pH 7.5, 0.3M NaCl, 2.5 mM MgCl2, 0.5% Triton X-100) and twice with Low salt wash buffer (20 mM Hepes, pH 7.5, 0.05M NaCl, 2.5 mM MgCl2, 0.5% Triton X-100). 5 μl 4xloading buffer was added to the precipitates. The whole cell lysates and precipitates were resolved by 10% SDS-PAGE and transferred onto nitrocellulose membranes by electrophoresis. The membranes were then incubated with Ponceau S (Sigma, St Louis, Mo.) to determine the quality of protein transfer and then blocked in TBS (10 mM TrisBase, 150 mM NaCl) containing 5% non-fat dry milk. The membranes were then incubated with primary antibody, as indicated in each experiment, for 1 hour at room temperature, in TBS/1% BSA (Bovine Serum Albumin) followed by Horseradish peroxidase-linked secondary antibody. The blots were developed by ECL (Amersham, Arlington Heights, Ill.)

Subcellular Localization Assays

CHO-IR cells were plated onto coverslips in 6 well plates and transfected with nucleotide sequences encoding the wild type and mutant forms of (1.5 μg/transfection) by Lipofectamine as described above. The cells were maintained in RPMI/10% FCS 5% $CO_2$ at 37° C. The wells were washed twice with PBS, 48 hrs post-transfection, and fixed for 10 min in 3.7% formaldehyde (1:10 v/v in PBS), followed by three washes with PBS. The cells were then permeabilized by a 1 minute incubation with PBS-containing 0.2% Triton X-100, followed by three washes with PBS and further incubation with PBS-containing 1% BSA for 10 min at room temperature. The cells were washed once with PBS and incubated with Phalloidin (Molecular Probes, Eugene Oreg. (0.01 mg/ml in PBS/1% BSA) for 30 min at 37° C. and the plates wrapped in aluminum foil to keep them dark. The wells were then washed three times with PBS and the coverslips mounted with vectashield (Vector Laboratories, Burlingame, Calif.). Expression of GFP-fusion proteins and their subcellular localization was examined by fluorescent and confocal microscopy.

In-Situ Hybridization Method used for the embryonic expression of tub mRNA

Probe generation

Oligos were designed to the tub sequence contained in the fume009 clone. The 5' tub sequence was CCGACTCGAT- TGCCAGTGTA (SEQ ID NO:16). To this the T3 polymerase sequence AATTAACCCTCACTAAAGGG (SEQ ID NO:76) was added for a complete oligo sequence of AAT-TAACCCTCACTAAAGGGCCGA CTCGATTGCCAGT-GTA (SEQ ID NO:77). The 3' tub sequence was CGGATA-CAGACTCTCTCAT (SEQ ID NO:78) (complementary). To this the T7 polymerase sequence TAATACGACTCAC-TATAGGG (SEQ ID NO:79) was added for a complete oligo sequence of TAATACGACTCACTATAGGGCGGATA CAGACTCTCTCAT (SEQ ID NO:80).

The resulting predominant PCR product was then capable of being transcribed in the sense or antisense direction. A cRNA probe was transcribed incorporating $^{35}$S UTP.

Tissue

Embryonic day 17 Swiss-Webster were collected and fresh frozen on dry ice. The embryos were then cut serially in the sagittal position at 10 μm thickness onto glass slices and stored at −80° C. until processed for in situ hybridization. In situ hybridization was performed by methods well known to those of skill in the art (see e.g., Current Protocols in Molecular Biology, ed. Ausubel et al., 1995 John Wiley & Sons, Inc.)

17.2. Results

The analysis of predicted amino acid sequence (mouse and human tub, Klein et al., 1996 Cell 85:281–290; Noben-Trauth et al., 1996 Nature 380:534–538) revealed several serine/threonine phosphorylation sites and tyrosine phosphorylation sites located at amino acid positions 12, 74, 83, 230, 311, 327, 343, 371, 438, 465, 481 and 483. Several of the tyrosine residues lie in SH2-docking sequences. The tyrosine phosphorylation motifs fit the consensus sequence for phosphorylation by receptor protein-tyrosine kinases, such as the insulin receptor. In addition, the tub gene product contains a nuclear localization sequence at amino acids 301–307. Further, the tub gene product contains two putative dibasic proteolytic cleavage sites at amino acids 300–305 and 380–383; and putative lipid acceptor sites at amino acids 501–505.

In situ hybridization analysis for the murine embryonic expression of tub mRNA revealed that tub is expressed predominantly in neuronal derived tissue. A strong signal was observed in all zones of the developing cerebral cortex, including the neopallial cortex, intermediate zone, ventricular zone, olfactory lobe, olfactory epithelium, midbrain, medulla oblongata, spinal cord, right trigerminal ganglion, left trigerminal ganglion, Rathke's pouch, dorsal root ganglia, enteric nervous. System (surrounding intestine denoted by puncuate signal) and the vena cava.

Cell lysates obtained from CHO-IR cells transiently expressing HA-tub, Mut-tub, Y3/F-tub or C/S-tub, were stimulated or not with insulin (100 nM for 10 min at 37° C.) and examined for the presence of the tub gene product by immunoprecipitation and Western blot analysis. The results demonstrate that all HA-tagged forms of the tub gene product are expressed and migrate, as a 60 kDa polypeptide. Insulin stimulation did not change the expression levels of the different HA-tagged versions of the tub gene products.

Analysis of anti-phosphotyrosine immuno-precipitation (FIG. 13A, B) and anti-phosphotyrosine immunoblot demonstrated that several proteins become tyrosine-phosphorylated in response to insulin, IGF-1 and PDGF, including their respective receptors. Anti-tub immunoblot of anti-phosphotyrosine immunoprecipitates revealed that the tub gene product was phosphorylated only when cells were treated with insulin and IGF-1 but not with PDGF (FIG. 13A, B). This result suggest that the tub gene product is a substrate for insulin and IGF-1 receptors but not for PDGF receptor.

CHOIR cells transiently transfected with HA-tub, Mut-tub, Y3/F-tub and C/S-tub when stimulated with insulin (100 nM for 15 min at 37° C.) showed that only tub and Y3/F-tub become tyrosine phosphorylated and responds to insulin. All HA-tagged versions of the tub gene product were expressed at comparable levels as revealed.

This result shows that Mut-tub does not undergo tyrosine phosphorylation in response to insulin. This mutant may be defective in transmitting downstream signals originating at the insulin receptor level. The wild type tub gene product (HA-tub) and the mutant tub gene product (Mut-tub) behave differently. Wild type tub may have a key function for example, in propagation of a signaling cascade. The carboxy terminal tyrosines are not the key sites of phosphorylation by the insulin receptor. Replacement of the penultimate cysteine residue by serine abolishes tub gene product tyrosine phosphorylation, although all putative tyrosine phosphorylation sites remain intact. This result shows that the lack of the penultimate cysteine, and not the absence of the carboxy terminal tyrosines, as the reason why Mut-tub does not undergo tyrosine phosphorylation in response to insulin.

CHO-IR and 3T3-IR cells transiently expressing GFP or GFP-tub, HA-tub, Mut-tub, Y3/F-tub and C/S-tub were fixed and stained with phalloidin to highlight the actin network, as described in Experimental Procedures, and examined by fluorescent and confocal microscopy.

In cells growing in serum continuously, GFP staining is found homogeneously throughout the cell and HA-tub and Y3/F-tub are found in the cytosol and plasma membrane. The cytosolic staining is diffuse whereas the plasma membrane staining is patchy, indicating that the tub gene product is targeted to certain areas of the plasma membrane. Some cells revealed nuclear staining whereas in other cells transfected with wild type or Y3/F-tub, the tub gene product was completely excluded from the nucleus. Mut-tub and C/S-tub were found exclusively in the nucleus.

In serum starved cells, homogenous GFP staining was observed. WT-tub and Y3/F-tub demonstrate heavy nuclear staining and are also present in the cytoplasm and in patches at the plasma membrane. Mut-tub and C/S-tub are found exclusively in the nucleus. This result indicates that the wild type tub gene product and the mutant tub gene product have distinct subcellular localization patterns. It also explains why the mutant form of the tub gene product does not become tyrosine phosphorylated in response to insulin. The exclusive nuclear localization of Mut-tub precludes it from being a substrate for the insulin receptor. That is also the reason why the C/S-tub does not become tyrosine phosphorylated in response to insulin.

These results indicate that the penultimate residue, a cysteine (aa 504), has been identified as the key residue in tub that determines its subcellular localization, this cysteine may be an acceptor site for lipid modification, either prenylation or palmitylation. This sequence (KLACE) is not found in any other cellular proteins but other tub gene product family members.

The subcellular localization of the tub gene product varies according to the culture conditions. In starved cells, the tub gene product is found mostly in the nucleus with some cytosolic and membrane staining whereas when serum is added back, after a few hours, tub translocates from the nucleus to the cytosol and plasma membrane. tub gene product subcellular localization can be linked to the cell cycle. In addition, the tub gene product, itself can have a chaperon like function, shuttling proteins to different cellular compartments.

CHO-IR cells, transiently expressing HA-tagged WT-tub, were treated or not with insulin (100 nM) for 15 min at 37° C. The pre-cleared lysates were then incubated with GST or GST-SH2 fusion proteins bound to GSH- sepharose beads. After extensive washes, precipitated proteins were resolved by SDS-PAGE and analyzed by immunoblot for the presence of tub gene product. As shown in FIG. 14A, the tub gene product was precipitated by PLCγ-CSH2, Lck-SH2, Abl-SH2 and Src-SH2 and the association was enhanced when cells were pre-treated with insulin, confirming that this is a phosphotyrosine-mediated interaction. The tub gene product, however, was not pulled down by p85-NSH2, p85-CSH2, PLCγ-NSH2 or Grb2-SH2, indicating that this is a specific interaction mediated by the property of different SH2 domains to recognize distinct phosphotyrosine-containing sequences. The same membrane was also probed with an anti-phosphotyrosine antibody (FIG. 14B) and show that all SH2 domains used in this experiment pulled down phosphotyrosine-containing proteins from the cellular lysates, demonstrating that all SH2 domains are functional. The first two lanes shows that the same amount of tub gene product is present in both insulin stimulated and control cells.

To further understand the interaction of the tub gene product with PLCγ it was determined whether Mut-tub, Y3/F-tub and C/S-tub also interact with PLCγ-CSH2 and endogenous PLCγ. As shown in FIG. 15A, Y3/F-tub associates with PLCγ-CSH2 as well as the wild type tub gene product and that interaction is enhanced by insulin treatment. Very little C/S-tub is found in the complex (FIG. 15A), although they are all expressed at the same levels (FIG. 15B). Surprisingly, however, PLCγ-CSH2 precipitated large amounts of Mut-tub from both control and insulin-stimulated CHO-IR cells (FIG. 15A). Co-immunoprecipitation experiments revealed that both the wild type tub gene product and Y3/F-tub, but not C/S-tub, associate with endogenous PLCγ and that this interaction is slightly increased by insulin. Unexpectedly, Mut-tub gene product also associates with endogenous PLCγ and that interaction is greatly enhanced by insulin pre-treatment (15, upper panel). These results are compatible with our previous findings: both the wild type form of the tub gene product and Y3/F-tub are phosphorylated on tyrosine residues in response to insulin, and therefore can associate with SH2 domains, whereas C/S-tub is not. In addition the result matches the subcellular localization: both WT-tub and Y3/F-tub are present in the cytosol and at the plasma membrane, where lipid substrates are located, has been shown to be key for its function. Therefore, it is not surprising that C/S-tub gene product is neither precipitated by GST-PLCγ-CSH2 nor does it associate with endogenous PLCγ.

18. DEPOSIT OF MICROORGANISMS

The following microorganisms were deposited with the American Type Culture Collection (ATCC) 10801 University Boulevard, Manassas, Va. 20110-2209, on the dates indicated and were assigned the indicated accession numbers:

| Microorganism | Clone | ATCC Access. No. | Deposit Date |
|---|---|---|---|
| H019 (E. coli) | fumh019 | 69856 | June 29, 1995 |
| E/P8 (E. coli) | P8 | 69858 | June 30, 1995 |
| E/P6 (E. coli) | P6 | 69857 | June 30, 1995 |
| E/B13 (E. coli) | B13 | 69859 | June 30, 1995 |
| CBT9H1 (E. coli) | CBT9H1 | 97222 | July 10, 1995 |
| CBT9H2 (E. coli) | CBT9H2 | 97221 | July 10, 1995 |
| CBT9H3 (E. coli) | CBT9H3 | 69874 | July 28, 1995 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for identifying compounds that modulate tub protein activity, comprising:
   (a) contacting a cell expressing a tub protein, an extract thereof, or an isolated tub protein, in the presence or absence of a test compound with a SH2 containing peptide,
   (b) determining whether the test compound alters the interaction of the tub protein with the SH2 containing peptide, and
   (c) selecting the test compound that alters the interaction of the tub protein with the SH2 containing peptide
   wherein the tub protein comprises:
   (i) the amino acid sequence shown in SEQ ID NO:2,
   (ii) amino acid residues 1–133 shown in SEQ ID NO:2,
   (iii) amino acid residues 190–505 shown in SEQ ID NO:2,
   (iv) amino acid residues 1–133 and 190–505 shown in SEQ ID NO:2,
   (v) the amino acid sequence shown in SEQ ID NO:8,
   (vi) amino acid residues 1–133 shown in SEQ ID NO:8,
   (vii) amino acid residues 190–506 shown in SEQ ID NO:8,
   (viii) amino acid residues 1–133 and 190–506 shown in SEQ ID NO:8,
   (ix) an amino acid sequence encoded by the nucleic acid insert of the clone contained in ATCC Deposit No. 69856,
   (x) the amino acid sequence encoded by the nucleic acid insert of the clone contained in ATCC Deposit No. 97222,
   (xi) the amino acid sequence encoded by the nucleic acid insert of the clone contained in ATCC Deposit No. 97221,
   (xii) the amino acid sequence encoded by the nucleic acid insert of the clone contained in ATCC Deposit No. 69874,
   (xiii) the amino acid sequence encoded by the nucleic acid insert of the clone contained in ATCC Deposit No. 69857,
   (xiv) an amino acid sequence encoded by the nucleic acid insert of the clone contained in ATCC Deposit No. 69858, or
   (xv) an amino acid sequence encoded by the nucleic acid insert of the clone contained in ATCC Deposit No. 69859.

2. The method of claim 1 in which the SH2 containing peptide is selected from the group comprising PLC gamma, Abl, Lck, Hck, Fgr, BLk, Src, Fyn, Yes and Lyn kinase.

3. The method of claim 1 in which at least one tyrosine residue of the tub protein is phosphorylated.

4. The method of claim 1 in which the tub protein is contained in an isolated cellular extract.

5. The method of claim 1 which the tub protein is expressed recombinantly.

6. The method of claim 1 in which the tub protein is phosphorylated.

7. A method for identifying compounds that modulate tub protein activity, comprising:
   (a) contacting a cell expressing a tub protein, an extract thereof, or an isolated tub protein, in the presence or absence of a test compound with a SH2 containing peptide,
   (b) determining whether the test compound alters the interaction of the tub protein with the SH2 containing peptide, and
   (c) selecting the test compound that alters the interaction of the tub protein with the SH2 containing peptide,
   wherein the tub protein is encoded by an allele of a nucleotide sequence encoding:
   (i) the amino acid sequence shown in SEQ ID NO:2,
   (ii) amino acid residues 1–133 shown in SEQ ID NO:2,
   (iii) amino acid residues 190–505 shown in SEQ ID NO:2,
   (iv) amino acid residues 1–133 and 190–505 shown in SEQ ID NO:2,
   (v) the amino acid sequence shown in SEQ ID NO:8,
   (vi) amino acid residues 1–133 shown in SEQ ID NO:8,
   (vii) amino acid residues 190–506 shown in SEQ ID NO:8,
   (viii) amino acid residues 1–133 and 190–506 shown in SEQ ID NO:8,
   (ix) an amino acid sequence encoded by the nucleic acid insert of the clone contained in ATCC Deposit No. 69856,
   (x) the amino acid sequence encoded by the nucleic acid insert of the clone contained in ATCC Deposit No. 97222,
   (xi) the amino acid sequence encoded by the nucleic acid insert of the clone contained in ATCC Deposit No. 97221,
   (xii) the amino acid sequence encoded by the nucleic acid insert of the clone contained in ATCC Deposit No. 69874,
   (xiii) the amino acid sequence encoded by the nucleic acid insert of the clone contained in ATCC Deposit No. 69857,
   (xiv) an amino acid sequence encoded by the nucleic acid insert of the clone contained in ATCC Deposit No. 69858, or
   (xv) an amino acid sequence encoded by the nucleic acid insert of the clone contained in ATCC Deposit No. 69859,
   and wherein said allele is encoded by a tub gene locus and said nucleotide sequence hybridizes under stringent wash condition, 0.1×SSC, 0.1% SDS at 65° C., to the complement of a nucleotide sequence encoding any of (i)–(xv).

8. The method of claim 7 in which the SH2 containing peptide is selected from the group comprising PLC gamma, Abl, Lck, Hck, Fgr, BLk, Src, Fyn, Yes, and Lyn kinase.

9. The method of claim 7 in which at least one tyrosine residue of the tub protein is phosphorylated.

10. The method of claim 7 in which the tub protein is contained in an isolated cellular extract.

11. The method of claim 7 in which the tub protein is expressed recombinantly.

12. The method of claim 7 in which the tub protein is phosphorylated.

* * * * *

SEQUENCE LISTING ( 1 ) GENERAL INFORMATION:

( i i i ) NUMBER OF SEQUENCES: 82

( 2 ) INFORMATION FOR SEQ ID NO:1:

( i ) SEQUENCE CHARACTERISTICS:
        ( A ) LENGTH: 1804 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 139..1653

( x i ) SEQUENCE DESCRIPTION: SEQ ID NO:1:

```
CTGCAGGATT  CGGCACGAGC  AGCGGTCGGG  CCGGGGAGGA  TGCGGCCCGG  GGCGGCCCGA         60

GAGTTGAGCA  GGGTCCCCGC  GCCAGCCCCG  AGCGGTCCCG  GCCACCGGAG  CCGCAGCCGC        120
```

| | | | | | | | | | | | | | | | |
|---|---|---|---|---|---|---|---|---|---|---|---|---|---|---|---|
| CGCCCCGCCC | CCGGGAGA | ATG | ACT | TCC | AAG | CCG | CAT | TCC | GAC | TGG | ATT | CCT | | | 171 |
| | | Met | Thr | Ser | Lys | Pro | His | Ser | Asp | Trp | Ile | Pro | | | |
| | | 1 | | | 5 | | | | | | 10 | | | | |
| TAC | AGT | GTC | CTA | GAT | GAT | GAG | GGC | AGC | AAC | CTG | AGG | CAG | CAG | AAG | CTC | 219 |
| Tyr | Ser | Val | Leu | Asp | Asp | Glu | Gly | Ser | Asn | Leu | Arg | Gln | Gln | Lys | Leu |
| | | | 15 | | | | | 20 | | | | | 25 | | |
| GAC | CGG | CAG | CGG | GCC | CTG | TTG | GAA | CAG | AAG | CAG | AAG | AAG | AAG | CGC | CAA | 267 |
| Asp | Arg | Gln | Arg | Ala | Leu | Leu | Glu | Gln | Lys | Gln | Lys | Lys | Lys | Arg | Gln |
| | | 30 | | | | | 35 | | | | | 40 | | | |
| GAG | CCC | TTG | ATG | GTA | CAG | GCC | AAT | GCA | GAT | GGA | CGG | CCC | CGG | AGT | CGG | 315 |
| Glu | Pro | Leu | Met | Val | Gln | Ala | Asn | Ala | Asp | Gly | Arg | Pro | Arg | Ser | Arg |
| | 45 | | | | | 50 | | | | | 55 | | | | |
| CGA | GCC | CGG | CAG | TCA | GAG | GAG | CAA | GCC | CCC | CTG | GTG | GAG | TCC | TAC | CTC | 363 |
| Arg | Ala | Arg | Gln | Ser | Glu | Glu | Gln | Ala | Pro | Leu | Val | Glu | Ser | Tyr | Leu |
| 60 | | | | | 65 | | | | | 70 | | | | | 75 |
| AGC | AGC | AGT | GGC | AGC | ACC | AGC | TAC | CAA | GTT | CAA | GAG | GCC | GAC | TCG | ATT | 411 |
| Ser | Ser | Ser | Gly | Ser | Thr | Ser | Tyr | Gln | Val | Gln | Glu | Ala | Asp | Ser | Ile |
| | | | | 80 | | | | | 85 | | | | | 90 | |
| GCC | AGT | GTA | CAG | CTG | GGA | GCC | ACC | CGC | CCA | CCA | GCA | CCA | GCT | TCA | GCC | 459 |
| Ala | Ser | Val | Gln | Leu | Gly | Ala | Thr | Arg | Pro | Pro | Ala | Pro | Ala | Ser | Ala |
| | | | 95 | | | | | 100 | | | | | 105 | | |
| AAG | AAA | TCC | AAG | GGA | GCG | GCT | GCA | TCT | GGG | GGC | CAG | GGT | GGA | GCC | CCT | 507 |
| Lys | Lys | Ser | Lys | Gly | Ala | Ala | Ala | Ser | Gly | Gly | Gln | Gly | Gly | Ala | Pro |
| | | 110 | | | | | 115 | | | | | 120 | | | |
| AGG | AAG | GAG | AAG | AAG | GGA | AAG | CAT | AAA | GGC | ACC | AGC | GGG | CCA | GCA | ACT | 555 |
| Arg | Lys | Glu | Lys | Lys | Gly | Lys | His | Lys | Gly | Thr | Ser | Gly | Pro | Ala | Thr |
| | 125 | | | | | 130 | | | | | 135 | | | | |
| CTG | GCA | GAA | GAC | AAG | TCT | GAG | GCC | CAA | GGC | CCA | GTG | CAG | ATC | TTG | ACT | 603 |
| Leu | Ala | Glu | Asp | Lys | Ser | Glu | Ala | Gln | Gly | Pro | Val | Gln | Ile | Leu | Thr |
| 140 | | | | | 145 | | | | | 150 | | | | | 155 |
| GTG | GGA | CAG | TCA | GAC | CAC | GAC | AAG | GAT | GCG | GGA | GAG | ACA | GCA | GCC | GGC | 651 |
| Val | Gly | Gln | Ser | Asp | His | Asp | Lys | Asp | Ala | Gly | Glu | Thr | Ala | Ala | Gly |
| | | | | 160 | | | | | 165 | | | | | 170 | |
| GGG | GGC | GCA | CAG | CCC | AGT | GGG | CAG | GAC | CTC | CGT | GCC | ACG | ATG | CAG | AGG | 699 |
| Gly | Gly | Ala | Gln | Pro | Ser | Gly | Gln | Asp | Leu | Arg | Ala | Thr | Met | Gln | Arg |
| | | | 175 | | | | | 180 | | | | | 185 | | |
| AAG | GGC | ATC | TCC | AGC | AGC | ATG | AGC | TTT | GAC | GAG | GAC | GAG | GAT | GAG | GAT | 747 |
| Lys | Gly | Ile | Ser | Ser | Ser | Met | Ser | Phe | Asp | Glu | Asp | Glu | Asp | Glu | Asp |
| | | 190 | | | | | 195 | | | | | 200 | | | |
| GAA | AAC | AGC | TCC | AGC | TCC | TCC | CAG | CTA | AAC | AGC | AAC | ACC | CGC | CCT | AGT | 795 |
| Glu | Asn | Ser | Ser | Ser | Ser | Ser | Gln | Leu | Asn | Ser | Asn | Thr | Arg | Pro | Ser |
| | 205 | | | | | 210 | | | | | 215 | | | | |
| TCT | GCC | ACT | AGC | AGA | AAG | TCC | ATC | CGG | GAG | GCA | GCT | TCA | GCC | CCC | AGC | 843 |
| Ser | Ala | Thr | Ser | Arg | Lys | Ser | Ile | Arg | Glu | Ala | Ala | Ser | Ala | Pro | Ser |
| 220 | | | | | 225 | | | | | 230 | | | | | 235 |
| CCA | GCC | GCC | CCA | GAG | CCA | CCA | GTG | GAT | ATT | GAG | GTC | CAG | GAT | CTA | GAG | 891 |
| Pro | Ala | Ala | Pro | Glu | Pro | Pro | Val | Asp | Ile | Glu | Val | Gln | Asp | Leu | Glu |
| | | | | 240 | | | | | 245 | | | | | 250 | |
| GAG | TTT | GCA | CTG | AGG | CCA | GCC | CCA | CAA | GGG | ATC | ACC | ATC | AAA | TGC | CGC | 939 |
| Glu | Phe | Ala | Leu | Arg | Pro | Ala | Pro | Gln | Gly | Ile | Thr | Ile | Lys | Cys | Arg |
| | | | 255 | | | | | 260 | | | | | 265 | | |
| ATC | ACT | CGG | GAC | AAG | AAG | GGG | ATG | GAC | CGC | GGC | ATG | TAC | CCC | ACC | TAC | 987 |
| Ile | Thr | Arg | Asp | Lys | Lys | Gly | Met | Asp | Arg | Gly | Met | Tyr | Pro | Thr | Tyr |
| | | 270 | | | | | 275 | | | | | 280 | | | |
| TTT | CTG | CAC | CTA | GAC | CGT | GAG | GAT | GGC | AAG | AAG | GTG | TTC | CTC | CTG | GCG | 1035 |
| Phe | Leu | His | Leu | Asp | Arg | Glu | Asp | Gly | Lys | Lys | Val | Phe | Leu | Leu | Ala |
| | 285 | | | | | 290 | | | | | 295 | | | | |
| GGC | AGG | AAG | AGA | AAG | AAG | AGT | AAA | ACT | TCC | AAT | TAC | CTC | ATC | TCT | GTG | 1083 |
| Gly | Arg | Lys | Arg | Lys | Lys | Ser | Lys | Thr | Ser | Asn | Tyr | Leu | Ile | Ser | Val |
| 300 | | | | | 305 | | | | | 310 | | | | | 315 |

| | | | | | | | | | | | | | | | | |
|---|---|---|---|---|---|---|---|---|---|---|---|---|---|---|---|---|
| GAC | CCA | ACA | GAC | TTG | TCT | CGG | GGA | GGC | GAT | AGC | TAT | ATC | GGG | AAA | TTG | 1131 |
| Asp | Pro | Thr | Asp | Leu | Ser | Arg | Gly | Gly | Asp | Ser | Tyr | Ile | Gly | Lys | Leu | |
| | | | | 320 | | | | 325 | | | | | | 330 | | |
| CGG | TCC | AAC | CTG | ATG | GGC | ACC | AAG | TTC | ACC | GTT | TAT | GAC | AAT | GGC | GTC | 1179 |
| Arg | Ser | Asn | Leu | Met | Gly | Thr | Lys | Phe | Thr | Val | Tyr | Asp | Asn | Gly | Val | |
| | | 335 | | | | | | 340 | | | | | 345 | | | |
| AAC | CCT | CAG | AAG | GCA | TCC | TCT | TCC | ACG | CTG | GAA | AGC | GGA | ACC | TTG | CGC | 1227 |
| Asn | Pro | Gln | Lys | Ala | Ser | Ser | Ser | Thr | Leu | Glu | Ser | Gly | Thr | Leu | Arg | |
| | | 350 | | | | | 355 | | | | | 360 | | | | |
| CAG | GAG | CTG | GCA | GCG | GTG | TGC | TAT | GAG | ACA | AAT | GTC | CTA | GGC | TTC | AAG | 1275 |
| Gln | Glu | Leu | Ala | Ala | Val | Cys | Tyr | Glu | Thr | Asn | Val | Leu | Gly | Phe | Lys | |
| | 365 | | | | | 370 | | | | | 375 | | | | | |
| GGA | CCT | CGG | AAG | ATG | AGT | GTG | ATC | GTC | CCA | GGC | ATG | AAC | ATG | GTT | CAT | 1323 |
| Gly | Pro | Arg | Lys | Met | Ser | Val | Ile | Val | Pro | Gly | Met | Asn | Met | Val | His | |
| 380 | | | | | 385 | | | | | 390 | | | | | 395 | |
| GAG | AGA | GTC | TGT | ATC | CGC | CCC | CGC | AAT | GAA | CAT | GAG | ACC | CTG | TTA | GCA | 1371 |
| Glu | Arg | Val | Cys | Ile | Arg | Pro | Arg | Asn | Glu | His | Glu | Thr | Leu | Leu | Ala | |
| | | | | 400 | | | | | 405 | | | | | 410 | | |
| CGC | TGG | CAG | AAC | AAG | AAC | ACG | GAG | AGC | ATC | ATT | GAG | CTG | CAG | AAC | AAG | 1419 |
| Arg | Trp | Gln | Asn | Lys | Asn | Thr | Glu | Ser | Ile | Ile | Glu | Leu | Gln | Asn | Lys | |
| | | | 415 | | | | | 420 | | | | | 425 | | | |
| ACG | CCA | GTC | TGG | AAT | GAT | GAC | ACA | CAG | TCC | TAT | GTA | CTT | AAC | TTC | CAC | 1467 |
| Thr | Pro | Val | Trp | Asn | Asp | Asp | Thr | Gln | Ser | Tyr | Val | Leu | Asn | Phe | His | |
| | | 430 | | | | | 435 | | | | | 440 | | | | |
| GGC | CGT | GTC | ACA | CAG | GCT | TCT | GTG | AAG | AAC | TTC | CAG | ATC | ATC | CAC | GGC | 1515 |
| Gly | Arg | Val | Thr | Gln | Ala | Ser | Val | Lys | Asn | Phe | Gln | Ile | Ile | His | Gly | |
| | 445 | | | | | 450 | | | | | 455 | | | | | |
| AAT | GAC | CCG | GAC | TAC | ATC | GTC | ATG | CAG | TTT | GGC | CGG | GTA | GCA | GAA | GAT | 1563 |
| Asn | Asp | Pro | Asp | Tyr | Ile | Val | Met | Gln | Phe | Gly | Arg | Val | Ala | Glu | Asp | |
| 460 | | | | | 465 | | | | | 470 | | | | | 475 | |
| GTG | TTC | ACC | ATG | GAT | TAC | AAC | TAC | CCA | CTG | TGT | GCA | CTG | CAG | GCC | TTC | 1611 |
| Val | Phe | Thr | Met | Asp | Tyr | Asn | Tyr | Pro | Leu | Cys | Ala | Leu | Gln | Ala | Phe | |
| | | | | 480 | | | | 485 | | | | | 490 | | | |
| GCC | ATT | GCT | CTG | TCC | AGC | TTT | GAC | AGC | AAG | CTG | GCC | TGC | GAG | | | 1653 |
| Ala | Ile | Ala | Leu | Ser | Ser | Phe | Asp | Ser | Lys | Leu | Ala | Cys | Glu | | | |
| | | | 495 | | | | 500 | | | | 505 | | | | | |

```
TAGAGGCCCC CCACTGCCGT TAGGTGGCCC AGTCCGGAGT GGAGCTTGCC TGCCTGCCAA    1713

GACAGGCTG  CCTACCCTCT GTTCATAGGC CCTCTATGGG CTTTCTGGTC TGACCAACCA    1773

GAGATTGGTT TGCTCTGCCT CTGCTGCTTG A                                   1804
```

( 2 ) INFORMATION FOR SEQ ID NO:2:

( i ) SEQUENCE CHARACTERISTICS:
        ( A ) LENGTH: 505 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Thr | Ser | Lys | Pro | His | Ser | Asp | Trp | Ile | Pro | Tyr | Ser | Val | Leu | Asp |
| 1 | | | | 5 | | | | | 10 | | | | | 15 | |
| Asp | Glu | Gly | Ser | Asn | Leu | Arg | Gln | Gln | Lys | Leu | Asp | Arg | Gln | Arg | Ala |
| | | | | 20 | | | | | 25 | | | | | 30 | |
| Leu | Leu | Glu | Gln | Lys | Gln | Lys | Lys | Arg | Gln | Glu | Pro | Leu | Met | Val | |
| | | | 35 | | | | | 40 | | | | | 45 | | |
| Gln | Ala | Asn | Ala | Asp | Gly | Arg | Pro | Arg | Ser | Arg | Arg | Ala | Arg | Gln | Ser |
| | 50 | | | | | 55 | | | | | 60 | | | | |
| Glu | Glu | Gln | Ala | Pro | Leu | Val | Glu | Ser | Tyr | Leu | Ser | Ser | Ser | Gly | Ser |

|   | 65 |   |   |   | 70 |   |   |   | 75 |   |   |   | 80 |
|---|---|---|---|---|---|---|---|---|---|---|---|---|---|

Thr Ser Tyr Gln Val Gln Glu Ala Asp Ser Ile Ala Ser Val Gln Leu
             85                    90                 95

Gly Ala Thr Arg Pro Pro Ala Pro Ala Ser Ala Lys Lys Ser Lys Gly
           100               105           110

Ala Ala Ala Ser Gly Gly Gln Gly Ala Pro Arg Lys Glu Lys Lys
        115           120           125

Gly Lys His Lys Gly Thr Ser Gly Pro Ala Thr Leu Ala Glu Asp Lys
    130               135              140

Ser Glu Ala Gln Gly Pro Val Gln Ile Leu Thr Val Gly Gln Ser Asp
145              150            155               160

His Asp Lys Asp Ala Gly Glu Thr Ala Ala Gly Gly Gly Ala Gln Pro
           165               170           175

Ser Gly Gln Asp Leu Arg Ala Thr Met Gln Arg Lys Gly Ile Ser Ser
           180               185           190

Ser Met Ser Phe Asp Glu Asp Asp Glu Asp Glu Asn Ser Ser Ser
        195           200            205

Ser Ser Gln Leu Asn Ser Asn Thr Arg Pro Ser Ser Ala Thr Ser Arg
    210               215              220

Lys Ser Ile Arg Glu Ala Ser Ala Pro Ser Pro Ala Ala Pro Glu
225              230            235           240

Pro Pro Val Asp Ile Glu Val Gln Asp Leu Glu Glu Phe Ala Leu Arg
           245              250           255

Pro Ala Pro Gln Gly Ile Thr Ile Lys Cys Arg Ile Thr Arg Asp Lys
           260               265           270

Lys Gly Met Asp Arg Gly Met Tyr Pro Thr Tyr Phe Leu His Leu Asp
        275           280            285

Arg Glu Asp Gly Lys Lys Val Phe Leu Leu Ala Gly Arg Lys Arg Lys
    290               295              300

Lys Ser Lys Thr Ser Asn Tyr Leu Ile Ser Val Asp Pro Thr Asp Leu
305              310            315           320

Ser Arg Gly Gly Asp Ser Tyr Ile Gly Lys Leu Arg Ser Asn Leu Met
           325              330           335

Gly Thr Lys Phe Thr Val Tyr Asp Asn Gly Val Asn Pro Gln Lys Ala
           340              345           350

Ser Ser Ser Thr Leu Glu Ser Gly Thr Leu Arg Gln Glu Leu Ala Ala
        355           360           365

Val Cys Tyr Glu Thr Asn Val Leu Gly Phe Lys Gly Pro Arg Lys Met
    370               375              380

Ser Val Ile Val Pro Gly Met Asn Met Val His Glu Arg Val Cys Ile
385              390            395           400

Arg Pro Arg Asn Glu His Glu Thr Leu Leu Ala Arg Trp Gln Asn Lys
           405              410           415

Asn Thr Glu Ser Ile Ile Glu Leu Gln Asn Lys Thr Pro Val Trp Asn
           420              425           430

Asp Asp Thr Gln Ser Tyr Val Leu Asn Phe His Gly Arg Val Thr Gln
        435           440            445

Ala Ser Val Lys Asn Phe Gln Ile Ile His Gly Asn Asp Pro Asp Tyr
    450               455              460

Ile Val Met Gln Phe Gly Arg Val Ala Glu Asp Val Phe Thr Met Asp
465              470            475           480

Tyr Asn Tyr Pro Leu Cys Ala Leu Gln Ala Phe Ala Ile Ala Leu Ser
           485              490           495

Ser Phe Asp Ser Lys Leu Ala Cys Glu
500                         505

( 2 ) INFORMATION FOR SEQ ID NO:3:

( i ) SEQUENCE CHARACTERISTICS:
       ( A ) LENGTH: 437 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:3:

| | | | | | | |
|---|---|---|---|---|---|---|
| ACGGCAATGA | CCTTGAGTGT | TGCCACTCCC | TGTTTTTGAT | GTTGTACGCA | TGGTGCCCAG | 60 |
| CCCCCACCCC | ACCCCCAATC | CCCTGATCTG | GTCCATATCA | GCCAGTGATG | GGATGTGGGT | 120 |
| ATATGGCTTT | TGTTAGAACT | TTCTAACTGT | AGTGATCTAG | AGTCCTGCCC | CTAGTGCCCT | 180 |
| GCATGTCTGG | GGCTTGGGAA | TACCCTTTAA | ATGGATGTCT | TTTCTCTCCT | GGGCCCTGCT | 240 |
| GTCTGTGTGC | ATCTCCCCCC | TTCACCCTCT | TGCTTCATAA | TGTTTCTCTT | GAACCTTTGT | 300 |
| TTTCTTCATC | CTTTCGATCT | CTTTGGCATT | TCTGCTTTCT | CCTTCCCTCT | TGTGGCCCAT | 360 |
| GTCTTACCTG | GTCTCCCTGT | CTCCACCATT | CTTGCTTGTG | CATTCCACAG | CGGACTACAT | 420 |
| CGTCATGCAT | TTTGGCC | | | | | 437 |

( 2 ) INFORMATION FOR SEQ ID NO:4:

( i ) SEQUENCE CHARACTERISTICS:
       ( A ) LENGTH: 437 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:4:

| | | | | | | |
|---|---|---|---|---|---|---|
| ACGGCAATGA | CCGTGAGTGT | TGCCACTCCC | TGTTTTTGAT | GTTGTACGCA | TGGTGCCCAG | 60 |
| CCCCCACCCC | ACCCCCAATC | CCCTGATCTG | GTCCATATCA | GCCAGTGATG | GGATGTGGGT | 120 |
| ATATGGCTTT | TGTAAGAACT | TTCTAACTGT | AGTGATCTAG | AGTCCTGCCC | CTAGTGCCCT | 180 |
| GCATGTCTGG | GGCTTGGGAA | TACCCTTTAA | ATGGATGTCT | TTTCTCTCCT | GGGCCCTGCT | 240 |
| GTCTGTGTGC | ATCTCCCCCC | TTCACCCTCT | TGCTTCATAA | TGTTTCTCTT | GAACCTTTGT | 300 |
| TTTGTTCATC | CTTTCGATCT | CTTTGGCATT | TCTGCTTTCT | CCTTCCCTCT | TGTGGCCCAT | 360 |
| GTCTTACCTG | GTCTCCCTGT | CTCCACCATT | CTTGCTTGTG | CATTCCACAG | CGGACTACAT | 420 |
| CGTCATGCAG | TTTGGCC | | | | | 437 |

( 2 ) INFORMATION FOR SEQ ID NO:5:

( i ) SEQUENCE CHARACTERISTICS:
       ( A ) LENGTH: 437 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:5:

| | | | | | | |
|---|---|---|---|---|---|---|
| ACGGCAATGA | CCTTGAGTGT | TGCCACTCCC | TGTTTTTGAT | GTTGTACGCA | TGGTGCCCAG | 60 |
| CCCCCACCCC | ACCCCCAATC | CCCTGATCTG | CTCCATATCA | GCCAGTGATG | GGATGTGGGT | 120 |
| ATATGGCTTT | TGTTAGAACT | TTCTAACTGT | AGTGATCTAG | AGTCCTGCCC | CTAGTGCCCT | 180 |

-continued

| | | | | | |
|---|---|---|---|---|---|
| GCATGTCTGG | GGCTTGGGAA | TACCCTTTAA | ATGGATGTCT | TTTCTCTCCT | GGGCCCTGCT | 240
| GTCTGTGTGC | ATCTCCCCCC | TTCACCCTCT | TGCTTCATAA | TGTTTCTCTT | GAACCTTTGT | 300
| TTTGTTCATC | CTTTCGATCT | CTTTGGCATT | TCTGCTTTCT | CCTTCCCTCT | TGTGGCCCAT | 360
| GTCTTACCTG | GTCTCCCTGT | CTCCACCATT | CTTGCTTGTG | CATTCCACAG | CGGACTACAT | 420
| CGTCATGCAG | TTTGGCC | | | | | 437

( 2 ) INFORMATION FOR SEQ ID NO:6:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:6:

ACGGCAATGA CCCGGACTAC ATCGTCATGC AGTTTGGCC            39

( 2 ) INFORMATION FOR SEQ ID NO:7:

( i ) SEQUENCE CHARACTERISTICS:
    ( A ) LENGTH: 2040 base pairs
    ( B ) TYPE: nucleic acid
    ( C ) STRANDEDNESS: single
    ( D ) TOPOLOGY: linear ( i i ) MOLECULE TYPE: DNA ( i x ) FEATURE:
    ( A ) NAME/KEY: CDS
    ( B ) LOCATION: 153..1670

( x i ) SEQUENCE DESCRIPTION: SEQ ID NO:7:

```
TGGCGTGCAG CAGGGGCCTC GGCGGGGCCC AGCCCNCCGG TCCCGGGGAG GATACGTCCC           60

GGGGGCGGCC CGGGAGCTGA GCAGGCCCCC CGCGCCGGCC CCTCCGGGCC CCGGCCTCCA          120

GAGCCGCAGC CACCGCCCCG CCCCCGAGAG AC ATG ACT TCC AAG CCG CAT TCC            173
                                   Met Thr Ser Lys Pro His Ser
                                    1               5

GAC TGG ATT CCC TAC AGT GTC TTA GAT GAT GAG GGC AGA AAC CTG AGG           221
Asp Trp Ile Pro Tyr Ser Val Leu Asp Asp Glu Gly Arg Asn Leu Arg
         10              15                  20

CAG CAG AAG CTT GAT CGG CAG CGG GCC CTG CTG GAG CAG AAG CAG AAG           269
Gln Gln Lys Leu Asp Arg Gln Arg Ala Leu Leu Glu Gln Lys Gln Lys
     25              30                  35

AAG AAG CGC CAG GAG CCC CTG ATG GTG CAG GCC AAT GCA GAT GGG CGG           317
Lys Lys Arg Gln Glu Pro Leu Met Val Gln Ala Asn Ala Asp Gly Arg
 40              45                  50                  55

CCC CGG AGC CGG CGG GCC CGG CAG TCA GAG GAA CAA GCC CCC CTG GTG           365
Pro Arg Ser Arg Arg Ala Arg Gln Ser Glu Glu Gln Ala Pro Leu Val
                 60                  65                  70

GAG TCC TAC CTC AGC AGC AGT GGC AGC ACC AGC TAC CAA GTT CAA GAG           413
Glu Ser Tyr Leu Ser Ser Ser Gly Ser Thr Ser Tyr Gln Val Gln Glu
             75                  80                  85

GCC GAC TCA CTC GCC AGT GTG CAG CTG GGA GCC ACG CGC CCA ACA GCA           461
Ala Asp Ser Leu Ala Ser Val Gln Leu Gly Ala Thr Arg Pro Thr Ala
             90                  95                 100

CCA GCT TCA GCC AAG AGA ACC AAG GCG GCA GCT ACA GCA GGG GGC CAG           509
Pro Ala Ser Ala Lys Arg Thr Lys Ala Ala Ala Thr Ala Gly Gly Gln
        105                 110                 115

GGT GGC GCC GCT AGG AAG GAG AAG AAG GGA AAG CAC AAA GGC ACC AGC           557
Gly Gly Ala Ala Arg Lys Glu Lys Lys Gly Lys His Lys Gly Thr Ser
```

-continued

```
                  120                            125                            130                             135
GGG  CCA  GCA  GCA  CTG  GCA  GAA  GAC  AAG  TCT  GAG  GCC  CAA  GGC  CCA  GTG                                  605
Gly  Pro  Ala  Ala  Leu  Ala  Glu  Asp  Lys  Ser  Glu  Ala  Gln  Gly  Pro  Val
                    140                           145                           150

CAG  ATT  CTG  ACT  GTG  GGC  CAG  TCA  GAC  CAC  GCC  CAG  GAC  GCA  GGG  GAG                                  653
Gln  Ile  Leu  Thr  Val  Gly  Gln  Ser  Asp  His  Ala  Gln  Asp  Ala  Gly  Glu
               155                           160                           165

ACG  GCA  GCT  GGT  GGG  GGC  GAA  CGG  CCC  AGC  GGG  CAG  GAT  CTC  CGT  GCC                                  701
Thr  Ala  Ala  Gly  Gly  Gly  Glu  Arg  Pro  Ser  Gly  Gln  Asp  Leu  Arg  Ala
               170                           175                           180

ACG  ATG  CAG  AGG  AAG  GGC  ATC  TCC  AGC  AGC  ATG  AGC  TTT  GAC  GAG  GAT                                  749
Thr  Met  Gln  Arg  Lys  Gly  Ile  Ser  Ser  Ser  Met  Ser  Phe  Asp  Glu  Asp
     185                           190                           195

GAG  GAG  GAT  GAG  GAG  GAG  AAT  AGC  TCC  AGC  TCC  TCC  CAG  CTA  AAT  AGT                                  797
Glu  Glu  Asp  Glu  Glu  Glu  Asn  Ser  Ser  Ser  Ser  Ser  Gln  Leu  Asn  Ser
200                           205                           210                           215

AAC  ACC  CGC  CCC  AGC  TCT  GCT  ACT  AGC  AGG  AAG  TCC  GTC  AGG  GAG  GCA                                  845
Asn  Thr  Arg  Pro  Ser  Ser  Ala  Thr  Ser  Arg  Lys  Ser  Val  Arg  Glu  Ala
                         220                           225                           230

GCC  TCA  GCC  CCT  AGC  CCA  ACA  GCT  CCA  GAG  CAA  CCA  GTG  GAC  GTT  GAG                                  893
Ala  Ser  Ala  Pro  Ser  Pro  Thr  Ala  Pro  Glu  Gln  Pro  Val  Asp  Val  Glu
               235                           240                           245

GTC  CAG  GAT  CTT  GAG  GAG  TTT  GCA  CTG  AGG  CCG  GCC  CCC  CAG  GGT  ATC                                  941
Val  Gln  Asp  Leu  Glu  Glu  Phe  Ala  Leu  Arg  Pro  Ala  Pro  Gln  Gly  Ile
          250                           255                           260

ACC  ATC  AAA  TGC  CGC  ATC  ACT  CGG  GAC  AAG  AAA  GGG  ATG  GAC  CGG  GGC                                  989
Thr  Ile  Lys  Cys  Arg  Ile  Thr  Arg  Asp  Lys  Lys  Gly  Met  Asp  Arg  Gly
          265                           270                           275

ATG  TAC  CCC  ACC  TAC  TTT  CTG  CAC  CTG  GAC  CGT  GAG  GAT  GGG  AAG  AAG                                 1037
Met  Tyr  Pro  Thr  Tyr  Phe  Leu  His  Leu  Asp  Arg  Glu  Asp  Gly  Lys  Lys
280                           285                           290                           295

GTG  TTC  CTC  CTG  GCG  GGA  AGG  AAG  AGA  AAG  AAG  AGT  AAA  ACT  TCC  AAT                                 1085
Val  Phe  Leu  Leu  Ala  Gly  Arg  Lys  Arg  Lys  Lys  Ser  Lys  Thr  Ser  Asn
                    300                           305                           310

TAC  CTC  ATC  TCT  GTG  GAC  CCA  ACA  GAC  TTG  TCT  CGA  GGA  GGG  GAC  AGC                                 1133
Tyr  Leu  Ile  Ser  Val  Asp  Pro  Thr  Asp  Leu  Ser  Arg  Gly  Gly  Asp  Ser
               315                           320                           325

TAT  ATC  GGG  AAA  CTG  CGG  TCC  AAC  TTG  ATG  GGC  ACC  AAG  TTC  ACT  GTT                                 1181
Tyr  Ile  Gly  Lys  Leu  Arg  Ser  Asn  Leu  Met  Gly  Thr  Lys  Phe  Thr  Val
          330                           335                           340

TAT  GAC  AAT  GGA  GTC  AAC  CCT  CAG  AAG  GCC  TCA  TCC  TCC  ACT  TTG  GAA                                 1229
Tyr  Asp  Asn  Gly  Val  Asn  Pro  Gln  Lys  Ala  Ser  Ser  Ser  Thr  Leu  Glu
     345                           350                           355

AGT  GGA  ACC  TTA  CGT  CAG  GAG  CTG  GCA  GCT  GTG  TGC  TAC  GAG  ACA  AAC                                 1277
Ser  Gly  Thr  Leu  Arg  Gln  Glu  Leu  Ala  Ala  Val  Cys  Tyr  Glu  Thr  Asn
360                           365                           370                           375

GTC  TTA  GGC  TTC  AAG  GGG  CCT  CGG  AAG  ATG  AGC  GTG  ATT  GTC  CCA  GGC                                 1325
Val  Leu  Gly  Phe  Lys  Gly  Pro  Arg  Lys  Met  Ser  Val  Ile  Val  Pro  Gly
                    380                           385                           390

ATG  AAC  ATG  GTT  CAT  GAG  AGA  GTC  TCT  ATC  CGC  CCC  CGC  AAC  GAG  CAT                                 1373
Met  Asn  Met  Val  His  Glu  Arg  Val  Ser  Ile  Arg  Pro  Arg  Asn  Glu  His
               395                           400                           405

GAG  ACA  CTG  CTA  GCA  CGC  TGG  CAG  AAT  AAG  AAC  ACG  GAG  AGT  ATC  ATC                                 1421
Glu  Thr  Leu  Leu  Ala  Arg  Trp  Gln  Asn  Lys  Asn  Thr  Glu  Ser  Ile  Ile
          410                           415                           420

GAG  CTG  CAA  AAC  AAG  ACA  CCT  GTC  TGG  AAT  GAT  GAC  ACA  CAG  TCC  TAT                                 1469
Glu  Leu  Gln  Asn  Lys  Thr  Pro  Val  Trp  Asn  Asp  Asp  Thr  Gln  Ser  Tyr
     425                           430                           435

GTA  CTC  AAC  TTC  CAT  GGG  CGC  GTC  ACA  CAG  GCC  TCC  GTG  AAG  AAC  TTC                                 1517
Val  Leu  Asn  Phe  His  Gly  Arg  Val  Thr  Gln  Ala  Ser  Val  Lys  Asn  Phe
```

```
                440                                 445                                 450                                 455
CAG  ATC  ATC  CAT  GGC  AAT  GAC  CCG  GAC  TAC  ATC  GTG  ATG  CAG  TTT  GGC                1565
Gln  Ile  Ile  His  Gly  Asn  Asp  Pro  Asp  Tyr  Ile  Val  Met  Gln  Phe  Gly
                    460                                 465                           470

CGG  GTA  GCA  GAG  GAT  GTG  TTC  ACC  ATG  GAT  TAC  AAC  TAC  CCG  CTG  TGT                1613
Arg  Val  Ala  Glu  Asp  Val  Phe  Thr  Met  Asp  Tyr  Asn  Tyr  Pro  Leu  Cys
                    475                                 480                           485

GCA  CTG  CAG  GCC  TTT  GCC  ATT  GCC  CTG  TCC  AGC  TTC  GAC  AGC  AAG  CTG                1661
Ala  Leu  Gln  Ala  Phe  Ala  Ile  Ala  Leu  Ser  Ser  Phe  Asp  Ser  Lys  Leu
          490                           495                           500

GCG  TGC  GAG  TAGAGGCCTC  TTCGTGCCCT  TTGGGGTTGC  CCAGCCTGGA                                  1710
Ala  Cys  Glu
          505

GCGGAGCTTG  CCTGCCTGCC  TGTGGAGACA  GCCCTGCCTA  TCCTCTGTAT  ATAGGCCTTC                         1770

CGCCAGATGA  AGCTTTGGCC  CTCAGTGGGC  TCCCTGGCCC  AGCCAGCCAG  GAACTGGCTC                         1830

CTTTGGCTCT  GCTACTGAGG  CAGGGGAGTA  GTGGAGAGCG  GGTGGGTGGG  TGTTGAAGGG                         1890

ATTGAGAATT  AATTCTTTCC  ATGCCACGAG  GATCAACACA  CACTCCCACC  CTTGGGTAGT                         1950

AAGTGGTTGT  TGTNAGTCGG  TACTTTACCA  AAGCTTGAGC  AACCTCTTCC  AAGCTTGGGA                         2010

AAGGGCCGCA  AAAAGGCATT  AGGAGGGGAG                                                             2040
```

( 2 ) INFORMATION FOR SEQ ID NO:8:

( i ) SEQUENCE CHARACTERISTICS:
        ( A ) LENGTH: 506 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:8:

```
Met  Thr  Ser  Lys  Pro  His  Ser  Asp  Trp  Ile  Pro  Tyr  Ser  Val  Leu  Asp
 1                    5                        10                         15

Asp  Glu  Gly  Arg  Asn  Leu  Arg  Gln  Gln  Lys  Leu  Asp  Arg  Gln  Arg  Ala
                20                        25                        30

Leu  Leu  Glu  Gln  Lys  Gln  Lys  Lys  Arg  Gln  Glu  Pro  Leu  Met  Val
               35                        40                        45

Gln  Ala  Asn  Ala  Asp  Gly  Arg  Pro  Arg  Ser  Arg  Arg  Ala  Arg  Gln  Ser
     50                        55                        60

Glu  Glu  Gln  Ala  Pro  Leu  Val  Glu  Ser  Tyr  Leu  Ser  Ser  Gly  Ser
 65                       70                        75                        80

Thr  Ser  Tyr  Gln  Val  Gln  Glu  Ala  Asp  Ser  Leu  Ala  Ser  Val  Gln  Leu
                    85                        90                        95

Gly  Ala  Thr  Arg  Pro  Thr  Ala  Pro  Ala  Ser  Ala  Lys  Arg  Thr  Lys  Ala
               100                       105                       110

Ala  Ala  Thr  Ala  Gly  Gly  Gln  Gly  Gly  Ala  Ala  Arg  Lys  Glu  Lys  Lys
               115                       120                       125

Gly  Lys  His  Lys  Gly  Thr  Ser  Gly  Pro  Ala  Ala  Leu  Ala  Glu  Asp  Lys
     130                       135                       140

Ser  Glu  Ala  Gln  Gly  Pro  Val  Gln  Ile  Leu  Thr  Val  Gly  Gln  Ser  Asp
145                       150                       155                       160

His  Ala  Gln  Asp  Ala  Gly  Glu  Thr  Ala  Ala  Gly  Gly  Gly  Glu  Arg  Pro
                    165                       170                       175

Ser  Gly  Gln  Asp  Leu  Arg  Ala  Thr  Met  Gln  Arg  Lys  Gly  Ile  Ser  Ser
               180                       185                       190

Ser  Met  Ser  Phe  Asp  Glu  Asp  Glu  Glu  Asp  Glu  Glu  Glu  Asn  Ser  Ser
               195                       200                       205
```

| | | | | | | | | | | | | | | |
|---|---|---|---|---|---|---|---|---|---|---|---|---|---|---|
| Ser | Ser | Ser | Gln | Leu | Asn | Ser | Asn | Thr | Arg | Pro | Ser | Ser | Ala | Thr | Ser |
| | 210 | | | | 215 | | | | | 220 | | | | | |
| Arg | Lys | Ser | Val | Arg | Glu | Ala | Ala | Ser | Ala | Pro | Ser | Pro | Thr | Ala | Pro |
| 225 | | | | | 230 | | | | | 235 | | | | | 240 |
| Glu | Gln | Pro | Val | Asp | Val | Glu | Val | Gln | Asp | Leu | Glu | Glu | Phe | Ala | Leu |
| | | | | 245 | | | | | 250 | | | | | 255 | |
| Arg | Pro | Ala | Pro | Gln | Gly | Ile | Thr | Ile | Lys | Cys | Arg | Ile | Thr | Arg | Asp |
| | | | 260 | | | | | 265 | | | | | 270 | | |
| Lys | Lys | Gly | Met | Asp | Arg | Gly | Met | Tyr | Pro | Thr | Tyr | Phe | Leu | His | Leu |
| | | | 275 | | | | 280 | | | | | 285 | | | |
| Asp | Arg | Glu | Asp | Gly | Lys | Lys | Val | Phe | Leu | Leu | Ala | Gly | Arg | Lys | Arg |
| | | 290 | | | | 295 | | | | | 300 | | | | |
| Lys | Lys | Ser | Lys | Thr | Ser | Asn | Tyr | Leu | Ile | Ser | Val | Asp | Pro | Thr | Asp |
| 305 | | | | | 310 | | | | | 315 | | | | | 320 |
| Leu | Ser | Arg | Gly | Gly | Asp | Ser | Tyr | Ile | Gly | Lys | Leu | Arg | Ser | Asn | Leu |
| | | | | 325 | | | | | 330 | | | | | 335 | |
| Met | Gly | Thr | Lys | Phe | Thr | Val | Tyr | Asp | Asn | Gly | Val | Asn | Pro | Gln | Lys |
| | | | 340 | | | | | 345 | | | | | 350 | | |
| Ala | Ser | Ser | Ser | Thr | Leu | Glu | Ser | Gly | Thr | Leu | Arg | Gln | Glu | Leu | Ala |
| | | 355 | | | | | 360 | | | | | 365 | | | |
| Ala | Val | Cys | Tyr | Glu | Thr | Asn | Val | Leu | Gly | Phe | Lys | Gly | Pro | Arg | Lys |
| | 370 | | | | | 375 | | | | | 380 | | | | |
| Met | Ser | Val | Ile | Val | Pro | Gly | Met | Asn | Met | Val | His | Glu | Arg | Val | Ser |
| 385 | | | | | 390 | | | | | 395 | | | | | 400 |
| Ile | Arg | Pro | Arg | Asn | Glu | His | Glu | Thr | Leu | Leu | Ala | Arg | Trp | Gln | Asn |
| | | | | 405 | | | | | 410 | | | | | 415 | |
| Lys | Asn | Thr | Glu | Ser | Ile | Ile | Glu | Leu | Gln | Asn | Lys | Thr | Pro | Val | Trp |
| | | | 420 | | | | | 425 | | | | | 430 | | |
| Asn | Asp | Asp | Thr | Gln | Ser | Tyr | Val | Leu | Asn | Phe | His | Gly | Arg | Val | Thr |
| | | | 435 | | | | | 440 | | | | | 445 | | |
| Gln | Ala | Ser | Val | Lys | Asn | Phe | Gln | Ile | Ile | His | Gly | Asn | Asp | Pro | Asp |
| | | 450 | | | | | 455 | | | | | 460 | | | |
| Tyr | Ile | Val | Met | Gln | Phe | Gly | Arg | Val | Ala | Glu | Asp | Val | Phe | Thr | Met |
| 465 | | | | | 470 | | | | | 475 | | | | | 480 |
| Asp | Tyr | Asn | Tyr | Pro | Leu | Cys | Ala | Leu | Gln | Ala | Phe | Ala | Ile | Ala | Leu |
| | | | | 485 | | | | | 490 | | | | | 495 | |
| Ser | Ser | Phe | Asp | Ser | Lys | Leu | Ala | Cys | Glu | | | | | | |
| | | | 500 | | | | | 505 | | | | | | | |

( 2 ) INFORMATION FOR SEQ ID NO:9:

( i ) SEQUENCE CHARACTERISTICS:
       ( A ) LENGTH: 605 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:9:

```
AGCCTACAGT   TTAAACAGTC   GACTCTAGAC   TTAATTAAGG   NTCCGGNGCG   CCCCCGGGTA        60
CCGAGCTCTG   GTCTCACCCA   CTGCCTGTTT   CTCTCTCTCC   ATCTGGGGAT   GTTTCCTGAG       120
CAGTTCAAGA   GGCCGACTCA   CTCGCCAGTG   TGCAGCTGGG   AGCCACGCGC   CCAACAGCAC       180
CAGCTTCAGC   CAAGAGAACC   AAGGCGGCAG   CTACAGCAGG   GGGCCAGGGC   GGCGCCGCTA       240
GGAAGGAGAA   GAAGGGAAAG   CACAAAGGTC   AGCTCACATT   CTCTACAGCC   CTGCCCAGCA       300
```

| | | | | | | |
|---|---|---|---|---|---|---|
| GGCCTGGCCT | CCACTGTAGG | GCTGGGGAAG | GTTTGTCCTC | CTGACTTGGA | GGGGAGGGAT | 360 |
| AGGATGAACA | GCCTCAGGGA | AGACACAGAC | TGCCACTCTG | GGCACCCCCT | CAGGTGGCTC | 420 |
| ACAGGCCTCA | TCTAGCTTGG | GAGGTGCCTG | GGCTGCCTCT | GGGTGTGGGC | ATGCCTACCA | 480 |
| ACACTGCCAG | GAAGTGAAGT | CCTGCTCAGC | TTTGGCCCAG | AACCACCGTC | CCNANCTTNA | 540 |
| GTTACTTTGG | CCTTGAGGAA | CCTTTATNAT | GACCCCNTNA | AGGAGGATTT | TAACCAAGCT | 600 |
| GGATT | | | | | | 605 |

( 2 ) INFORMATION FOR SEQ ID NO:10:

( i ) SEQUENCE CHARACTERISTICS:
        ( A ) LENGTH: 826 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

| | | | | | | |
|---|---|---|---|---|---|---|
| TTCAAGGGCC | AAAGTTTTTT | AATGATGTAT | GGGAGTTAAT | GAAGGNGGTA | TGTGGGTNTG | 60 |
| TTNGNGGAAG | AAAACACCAG | CATTGATGGT | TGTAGNTGKT | GGTGTCCAKG | AATGATTGCT | 120 |
| GGCCTTGCCT | ATGGTNTGGA | TCAGTCCTTG | TTNTCCCATC | TTGTTTTTC | CCATGTGCAG | 180 |
| TTGGTTTTTG | TAGATGGCTG | CCGTCTGCTT | TAAAGGACGT | GAGGTGTTGT | AAACCAACCC | 240 |
| TCGGCAATTA | ATTTGGGGGA | AGAGCAGAAG | AAATGAAGCC | CAACATCCCT | TACTAGCTTA | 300 |
| CCAGTTGTTA | ACAGGCTGGT | GCAATCATTA | GTTTATAAA | AATCAGTTTT | GCAAATAAAG | 360 |
| TTTTGCAGAG | GGTTTCCCCA | CTCTTCCCTC | ATCCCCTTCA | TGGACGTCTG | AGAATCCAGG | 420 |
| CCCTCCTCTC | CTCCTCCTGG | ATGTAACTCA | GGCGTGTCCG | TGGCCTGCAG | GCACCAGCGG | 480 |
| GCCAGCAGCA | CTGGCAGAAG | ACAAGWCTGA | GGCCCAAGGC | CCAGTGCAGA | TTCTGACTGT | 540 |
| GGGCCAGTCA | GACCACGCCC | AGGACGCAGG | GGAGACGGCA | GCTGGTGGGG | GCGAACGGCC | 600 |
| CAGCGGGCAG | GATCTCCGTK | CCACGATGCA | GAGGAAGGGT | GAGCCCATG | GGGGCCCAGT | 660 |
| GATACCCCCA | AAACTCAGTC | CCAGGTTCTC | AGATGCACCT | TTCTCTGGA | GCATGGNCTT | 720 |
| CCTGTGTCCA | AACCCCTCCC | TGGCAATGGT | GGGTGAGGGT | GGGGCACACT | TCGGAGACAA | 780 |
| ATNAGAAACT | CTTAGGCAGG | GNCCCTGCTA | AGGCCCCAGG | GAGGCC | | 826 |

( 2 ) INFORMATION FOR SEQ ID NO:11:

( i ) SEQUENCE CHARACTERISTICS:
        ( A ) LENGTH: 1943 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

| | | | | | | |
|---|---|---|---|---|---|---|
| TTAAACAGTC | GACTCTAGAC | TTAATTAAGG | ATCCGGCGCG | CCCCCGGGTA | CCGAGCTCAG | 60 |
| TGCAGGCCTT | GATACACAAG | AGACAGTGGT | AGGGTGSCTG | CTAGGTAGTG | GGGTAATGTA | 120 |
| GGGACTGAGC | TGAAACTGGG | TGGTGGGGAT | ATATCCTGAG | GATTGTGGCC | AGCCCGGCT | 180 |
| CATGTGTGTA | CCTGAGAGAA | TATCCTTTTA | TATCTGGACA | TGTGTGGGAA | TATATGTGTG | 240 |
| AATGGGAGTC | TATATGTGTA | GATATGGCTA | AGAGTGTGTG | CATAAGTTTG | TGGGGTACA | 300 |
| GGTGAGTCAG | TGTCTGAACA | TGAGTATGTG | ACCATGTGTA | TTTCAGGGGC | AGGGTAGACT | 360 |
| TCTCCTCATT | CATCCCTTCT | TCTTCTCTCC | TTGGCCCAGG | CATCTCCAGC | AGCATGAGCT | 420 |

| | | | | | | |
|---|---|---|---|---|---|---|
| TTGACGAGGA | TGAGGAGGAT | GAGGAGGAGA | ATAGCTCCAG | CTCCTCCCAG | CTAAATAGTA | 480 |
| ACACCCGCCC | CAGCTCTGCT | ACTAGCAGGA | AGTCCGTCAG | GGTGAGTGAG | TGAGTCTGCA | 540 |
| TCCACAGCAG | TTTTTGGAGG | ACTGCTCATC | CGTTAGAGGT | GGACTGCATG | TGAAGAGATG | 600 |
| GACTCGTATG | CCTTTAGGAG | CTTCTCTGCT | GGCCTCTTAC | GTCCCTCTAC | CTTGCCTCCT | 660 |
| AACCTCTTCA | GCTAGGCCAG | CAGGGTGATG | TATGGGGGA | GATGCAGTTG | ACAGGATGA | 720 |
| CCTCTGAGGA | CCTCCCGTAT | CTCCCATCTC | CACCTCTAGG | AACTGTTGAG | GGCAGGGCTG | 780 |
| GGAAGATAGC | TTCTGACCCC | AGGCCCAGGC | TGGCCAGGCC | CCAATCCCAG | GATCCTTCCC | 840 |
| TCTCTCCCAC | CGCCACGTTA | GGAGGCAGAT | TTGGATCCCA | GACCACCAAT | TTGGGCTGCT | 900 |
| TAGGGTCCTT | GGGGCTCAGG | CACCTATTCT | GCATCCCCAT | AGGAGGCAGC | CTCAGCCCCT | 960 |
| AGCCCAACAG | CTCCAGAGCA | ACCAGTGGAC | GTTGAGGTCC | AGGATCTTGA | GGAGTTTGCA | 1020 |
| CTGAGGCCGC | CCCCCCAGGG | TATCACCATC | AAATGCCGCA | TCACTCGGGA | CAAGAAAGGG | 1080 |
| ATGGACCGGG | GCATGTACCC | CACCTACTTT | CTGCACCTGG | ACCGTGAGGA | TGGGAAGAAG | 1140 |
| GTAAGGTTGG | TCTGGGCATG | TTATCATCTA | GGCTTTACAG | CCCTTTGAAA | TCCTAGGGGC | 1200 |
| TGAAATGTGA | CTGGAAGTCT | CATATCTACC | GCTGACCTCT | CAGTTCCTCA | AAGAAACTGC | 1260 |
| CTTCGTGTCT | GGTCTGTGCA | CATCTTTGTG | TTTTCCAGTG | CATTTGTGTG | TGTGCACATA | 1320 |
| TGTGCGTTTG | GGAGCTGACG | CAACGGAGAG | AGTCTGTGTG | AGTGGCTCTC | ATGACTGTGT | 1380 |
| GCAGACCAGA | GGCTGAGTCT | GGAATATGAC | CTCATTCCAC | TCCCCAAGGT | GTTCCTCCTG | 1440 |
| GCGGGAAGGA | AGAGAAAGAA | GAGTAAAACT | TCCAATTACC | TCATCTCTGT | GGACCCAACA | 1500 |
| GACTTGTCTC | GAGGAGGGGA | CAGCTATATC | GGGAAACTGC | GGGTACTAGC | ATTCCCCCAG | 1560 |
| GAAGCAGGCG | GGAGTGGGAG | GGAGGGGCAG | GGGCAAGCTG | TCTGTAGAGG | GCCTGAATCT | 1620 |
| TCCTGAAGGA | GATCTAGGCC | AGGGATGGAT | ACTCTCCCAG | GATCCTCTCT | GATAATCACA | 1680 |
| TCCAACTGGA | GGCCTATGTC | TATGCCAGCC | TAGAGCCAGA | CTTGGAGATG | GGACTCACAC | 1740 |
| ACCCGACCCC | AAGCTGTTCC | CAGGAGGTGG | GTGCAGGCCC | ACCAAGAGTG | ATGGATCAA | 1800 |
| CCCCAGGGTG | TCACTGATAA | CGCAGGCCAC | CATGGAAGAG | TTGCCTTGGC | TCCATGGTCA | 1860 |
| ATGCCAAGGG | ACAGGGCTGA | GAGTGAGCTC | GGTACCCGGG | GGCGCKCCGG | ATCCTTAATT | 1920 |
| AAGTCTAGAG | TCGACTGTTT | AAG | | | | 1943 |

( 2 ) INFORMATION FOR SEQ ID NO:12:

( i ) SEQUENCE CHARACTERISTICS:
        ( A ) LENGTH: 881 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

| | | | | | | |
|---|---|---|---|---|---|---|
| GATTTAGNGG | AACACAGCAN | CTTGNGGGTG | GGANGGCAGT | GGTGAAGGGG | CAGGAAGGCT | 60 |
| CTGAGCCTAG | GCCTCCAGGT | GGGGGCAGTG | GGGAGGTAGG | GTTTGCTGAG | GAACTGAGTA | 120 |
| CCAGATTTGG | GGAGCATAAA | TAAAGATGAG | AGGTCAGGAG | CTAAAGCTGG | AGATGGGGCT | 180 |
| GGACTGAGAC | TTAGGCTGGC | TGCGACAGAG | GAGATCTCAT | CCTCTCTCCA | CGGGTGCTAA | 240 |
| GCCTCTTCCA | CTGTCTTATC | AGATGCCATT | CTGTTTGCTC | ACCTCCCATG | AGGAGAACTC | 300 |
| CCATGTTCCC | CCAGATAAAT | CTYCTGAAGA | ATCCTGATTG | ACCTCCCTGA | ATTGCTCTCA | 360 |
| CTGAACTGAA | ATGCACTTTG | AGTCAACTCA | GAGCAAGTCC | AGGCCTTCTG | CCCACGAAGT | 420 |

| | | | | | | |
|---|---|---|---|---|---|---|
| GTCTTCAAAG | ATGTGGATTC | AGTGAGCAGT | ATGCCTCCCT | GGGCCTGCTC | CTGTTCCAGC | 480 |
| CCAGAATGTT | TTGCAGGCTC | CTCATAGGAC | AGACGATGAG | CTGTTCCCTG | CTTCTGGGGC | 540 |
| AGAGGGTGCA | TGACTCTATA | CTGATTGTGC | CTTTATTTCA | GGTCCAACTT | GATGGGCACC | 600 |
| AAGTTCACTG | TTTATGACAA | TGGAGTCAAC | CCTCAGAAGG | CCTCATCCTC | CACTTTGGAA | 660 |
| AGTGGAACCT | TACGTCAGGA | GCTGGCAGCT | GTGTGCTACG | TGAGTCCTAG | GTTCGGGGGT | 720 |
| CTCTGATTTC | CAAGGTAGAT | ATGAAATCCA | GGACTTGATG | CCTGATCTAG | GGGCTATCCC | 780 |
| ATCCATCTTA | GTGGGTAGAC | AAGGCTGTGT | GGAGAGGGGC | TGTCCTCTGT | GGAGTGTTCC | 840 |
| TGGCCTAGGA | CAGGGGCTCT | GGCTCTCTCC | TCCTGACTTC | A | | 881 |

(2) INFORMATION FOR SEQ ID NO:13:

(i) SEQUENCE CHARACTERISTICS:
        (A) LENGTH: 1622 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

| | | | | | | |
|---|---|---|---|---|---|---|
| AGTAGTTTGC | CGGAYCGAAG | TGGAAGAACA | RCATTCCCGT | GAGCAGAACC | AAGGATGACG | 60 |
| CATAAGAGGA | GCTAGTTCTG | GCAGGGTAGA | GACCCCAGGG | GCTCAGTTCT | GGCCCGTGTT | 120 |
| AGGTTTAGAG | GGATGTGTGT | TAGACTTCGG | AGTGGAGATG | GTGGGAACTA | GCTCTTCCTC | 180 |
| TTTATTCCCG | TCCCCCCCAC | CTTCTCCAGT | AGGTAAATAG | ACGCCTCAGG | TGGCCAGTGT | 240 |
| TGCGTTCTCT | TTCCCAGGAG | ACAAACGTCT | TAGGCTTCAA | GGGVCCTCGG | AAGATGAGCG | 300 |
| TGATTGTCCC | AGGCATGAAC | ATGGTTCATG | AGAGAGTCTC | TATCCGCCCC | CGCAACGTGA | 360 |
| GTGTCTACCC | CTTCCTCCCC | TCTTTCCCCA | TCATCCTAGT | CTCTGCATGA | GCTTCTAAGG | 420 |
| GCAGAACTCC | AGCTGATGTG | TATATGTGGA | GGGGTACCAT | GTGAGAAAGC | CCTGGAGGTC | 480 |
| TAGGGAAATC | CAAGGACCCC | CATTCCCGGG | ATAGATCCCT | TTCTGGGGTG | GTCATGGTGC | 540 |
| CAAAGGCCTG | GGCCTGGCTC | AGGTGAGGCT | GCCCTCCCAG | GAGCATGAGA | CACTGCTAGC | 600 |
| ACGCTGGCAG | AATAAGAACA | CGGAGTGTAT | CATCGAGCTG | CAAAACAAGA | CACCTGTCTG | 660 |
| GAATGATGAC | ACACAGTCCT | ATGTACTCAA | CTTCCATGGG | CGCGTCACAC | AGGCCTCCGT | 720 |
| GAAGAACTTC | CAGATCATCC | ATGGCAATGA | CCGTGAGTGT | TTCTGTCCCT | ACTCATTATG | 780 |
| GTCCGTAGGA | TACCCAAGGC | CCTTAGCGTA | GGGTTCAGCC | CACCTAGCCC | TGCCTACACT | 840 |
| GGCTAGAGTT | TAAGAATGTG | AGCTATACAG | CTAAGGTTAG | ATGTATGGAA | CTTTCTAACC | 900 |
| CTAATGACTG | GGAGGTCCTG | GAAGAACCTT | CTTTGSAGCC | CTGGTCCTAG | ATTCTGTGTA | 960 |
| TTCAACGGAG | TCTCAGGCAC | GGGAACACCC | TTTAAAGGA | CTTTTCCTCT | TTTCTGTCCC | 1020 |
| CTGGTGTTCA | CATGCATCTT | ACTTTGTCCT | TTGSCATCTG | CCACCTCTTT | CCTGCCACTT | 1080 |
| CTCCCAATTG | GCCTTTGTTT | TACTTCCCTT | TGTGATTCCC | CTGGCATCTC | TGCTTCTCAC | 1140 |
| TTGTTCTTCC | CTCATGTGGT | TTGGGTGTCT | GTCTATCCTT | CCCTGGCTCT | ACCATTCCTG | 1200 |
| TCCTGTCCTT | TTCTCTGTCT | GTGCCTGTGC | TTGGCCCCAG | CGGACTACAT | CGTGATGCAG | 1260 |
| TTTGGCCGGG | TAGCAGAGGA | TGTGTTCACC | ATGGATTACA | ACTACCCGCT | GTGTGCACTG | 1320 |
| CAGGCCTTTG | CCATTGCCCT | GTCCAGCTTC | GACAGCAAGC | TGGCGTGCGA | GTAGAGGCCT | 1380 |
| CTTCGTGCCC | TTTGGGGTTG | CCCAGCCTGG | AGCGGAGCTT | GCCTGCCTGC | CTGTGGAGAC | 1440 |
| AGCCCTGCCT | ATCCTCTGTA | TATAGGCCTT | CCGCCAGATG | AAGCTTTGGC | CCTCAGTGGG | 1500 |
| CTCCCTGGCC | CAGCCAGCCA | GGAACTGGCT | CCTTTGCCTC | TGCTACTGAG | GCAGGGAGT | 1560 |

```
AGTGGAGAGC GGGTGGGTGG GTGTGAAGGG ATGAGAATAA TTCTTTCCAT GCCACGAGAT    1620

CC                                                                   1622
```

( 2 ) INFORMATION FOR SEQ ID NO:14:

( i ) SEQUENCE CHARACTERISTICS:
        ( A ) LENGTH: 1338 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..855

( x i ) SEQUENCE DESCRIPTION: SEQ ID NO:14:

```
GTG  ATA  AAG  AAC  AGC  AAT  CAA  AAG  GGC  AAA  GCC  AAA  GGA  AAA  GGC  AAA    48
Val  Ile  Lys  Asn  Ser  Asn  Gln  Lys  Gly  Lys  Ala  Lys  Gly  Lys  Gly  Lys
 1              5                        10                       15

AAG  AAA  GCG  AAG  GAG  GAG  AGG  GCC  CCG  TCT  CCC  CCC  GTG  GAG  GTG  GAC    96
Lys  Lys  Ala  Lys  Glu  Glu  Arg  Ala  Pro  Ser  Pro  Pro  Val  Glu  Val  Asp
               20                        25                       30

GAA  CCC  CGG  GAG  TTT  GTG  CTC  CGG  CCT  GCC  CCC  CAG  GGC  CGC  ACG  GTG   144
Glu  Pro  Arg  Glu  Phe  Val  Leu  Arg  Pro  Ala  Pro  Gln  Gly  Arg  Thr  Val
                    35                        40                       45

CGC  TGC  CGG  CTG  ACC  CGG  GAC  AAA  AAG  GGC  ATG  GAT  CGA  GGC  ATG  TAT   192
Arg  Cys  Arg  Leu  Thr  Arg  Asp  Lys  Lys  Gly  Met  Asp  Arg  Gly  Met  Tyr
     50                        55                        60

CCC  TCC  TAC  TTC  CTG  CAC  CTG  GAC  ACG  GAG  AAG  AAG  GTG  TTC  CTC  TTG   240
Pro  Ser  Tyr  Phe  Leu  His  Leu  Asp  Thr  Glu  Lys  Lys  Val  Phe  Leu  Leu
 65                       70                        75                       80

GCT  GGC  AGG  AAA  CGA  AAA  CGG  AGC  AAG  ACA  GCC  AAT  TAC  CTC  ATC  TCC   288
Ala  Gly  Arg  Lys  Arg  Lys  Arg  Ser  Lys  Thr  Ala  Asn  Tyr  Leu  Ile  Ser
                    85                        90                       95

ATC  GAC  CCT  ACC  AAT  CTG  TCC  CGA  GGA  GGG  GAG  AAT  TTC  ATC  GGG  AAG   336
Ile  Asp  Pro  Thr  Asn  Leu  Ser  Arg  Gly  Gly  Glu  Asn  Phe  Ile  Gly  Lys
               100                       105                      110

CTG  AGG  TCC  AAC  CTC  CTG  GGG  AAC  CGC  TTC  ACG  GTC  TTT  GAC  AAC  GGG   384
Leu  Arg  Ser  Asn  Leu  Leu  Gly  Asn  Arg  Phe  Thr  Val  Phe  Asp  Asn  Gly
          115                       120                      125

CAG  AAC  CCA  CAG  CGT  GGG  TAC  AGC  ACT  AAT  GTG  GCA  AGC  CTT  CGG  CAG   432
Gln  Asn  Pro  Gln  Arg  Gly  Tyr  Ser  Thr  Asn  Val  Ala  Ser  Leu  Arg  Gln
     130                      135                      140

GAG  CTG  GCA  GCT  GTG  ATC  TAT  GAA  ACC  AAC  GTG  CTG  GGC  TTC  CGT  GGC   480
Glu  Leu  Ala  Ala  Val  Ile  Tyr  Glu  Thr  Asn  Val  Leu  Gly  Phe  Arg  Gly
145                      150                      155                      160

CCC  CGG  CGC  ATG  ACC  GTC  ATC  ATT  CCT  GGC  ATG  AGT  GCG  GAG  AAC  GAG   528
Pro  Arg  Arg  Met  Thr  Val  Ile  Ile  Pro  Gly  Met  Ser  Ala  Glu  Asn  Glu
               165                      170                      175

AGG  GTC  CCC  ATC  CGG  CCC  CGA  AAT  GCT  AGT  GAC  GGC  CTG  CTG  GTG  CGC   576
Arg  Val  Pro  Ile  Arg  Pro  Arg  Asn  Ala  Ser  Asp  Gly  Leu  Leu  Val  Arg
                    180                      185                      190

TGG  CAG  AAC  AAG  ACG  CTG  GAG  AGC  CTC  ATA  GAA  CTG  CAC  AAC  AAG  CCA   624
Trp  Gln  Asn  Lys  Thr  Leu  Glu  Ser  Leu  Ile  Glu  Leu  His  Asn  Lys  Pro
          195                      200                      205

CCT  GTC  TGG  AAC  GAT  GAC  AGT  GGC  TCC  TAC  ACC  CTC  AAC  TTC  CAA  GGC   672
Pro  Val  Trp  Asn  Asp  Asp  Ser  Gly  Ser  Tyr  Thr  Leu  Asn  Phe  Gln  Gly
     210                      215                      220

CGG  GTC  ACC  CAG  GCC  TCA  GTC  AAG  AAC  TTC  CAG  ATT  GTC  CAC  GCT  GAT   720
Arg  Val  Thr  Gln  Ala  Ser  Val  Lys  Asn  Phe  Gln  Ile  Val  His  Ala  Asp
```

-continued

```
225                      230                      235                      240
GAC  CCC  GAC  TAT  ATC  GTG  CTG  CAG  TTC  GGC  CGC  GTG  GCG  GAG  GAC  GCC      768
Asp  Pro  Asp  Tyr  Ile  Val  Leu  Gln  Phe  Gly  Arg  Val  Ala  Glu  Asp  Ala
                    245                      250                      255

TTC  ACC  CTA  GAC  TAC  CGG  TAC  CCG  CTG  TGC  GCC  CTG  CAG  GCC  TTC  GCC      816
Phe  Thr  Leu  Asp  Tyr  Arg  Tyr  Pro  Leu  Cys  Ala  Leu  Gln  Ala  Phe  Ala
               260                      265                      270

ATC  GCC  CTC  TCC  AGT  TTC  GAC  GGG  AAG  CTG  GCC  TGC  GAG  TGACCCCAGC         865
Ile  Ala  Leu  Ser  Ser  Phe  Asp  Gly  Lys  Leu  Ala  Cys  Glu
               275                      280                      285

AGCCCCTCAG  CGCCCCCAGA  GCCCGTCAGC  GTGGGGGAAA  GGATTCAGTG  GAGGCTGGCA                925

GGGTCCCTCC  AGCAAAGCTC  CCGCGGAAAA  CTGCTCCTGT  GTCGGGGCTG  ACCTCTCACT                985

GCCTCTCGGT  GACCTCCGTC  CTCTCCCCAG  CCTGGCACAG  GCCGAGGCAG  GAGGAGCCCG               1045

GACGGCGGGT  AGGACGGAGA  TGAAGAACAT  CTGGAGTTGG  AGCCGCACAT  CTGGTCTCGG               1105

AGCTCGCCTG  CGCCGCTGTG  CCCCCCTCCT  CCCCGCGCCC  CAGTCACTTC  CTGTCCGGGA               1165

GCAGTAGTCA  TTGTTGTTTT  AACCTCCCCT  CTCCCCGGGA  CCGCGCTAGG  GCTCCGAGGA               1225

GCTGGGGCGG  GCTAGGAGGA  GGGGGTAGGT  GATGGGGGAC  GAGGGCCAGG  CACCCACATC               1285

CCCAATAAAG  CCGCGTCCTT  GGCAAAAAAA  AAAAAAAAA  AAAAAAAAA  AAA                        1338
```

( 2 ) INFORMATION FOR SEQ ID NO:15:

( i ) SEQUENCE CHARACTERISTICS:
        ( A ) LENGTH: 285 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:15:

```
Val  Ile  Lys  Asn  Ser  Asn  Gln  Lys  Gly  Lys  Ala  Lys  Gly  Lys  Gly  Lys
 1              5                        10                       15

Lys  Lys  Ala  Lys  Glu  Glu  Arg  Ala  Pro  Ser  Pro  Pro  Val  Glu  Val  Asp
               20                       25                       30

Glu  Pro  Arg  Glu  Phe  Val  Leu  Arg  Pro  Ala  Pro  Gln  Gly  Arg  Thr  Val
               35                       40                       45

Arg  Cys  Arg  Leu  Thr  Arg  Asp  Lys  Lys  Gly  Met  Asp  Arg  Gly  Met  Tyr
       50                       55                       60

Pro  Ser  Tyr  Phe  Leu  His  Leu  Asp  Thr  Glu  Lys  Lys  Val  Phe  Leu  Leu
 65                       70                       75                       80

Ala  Gly  Arg  Lys  Arg  Lys  Arg  Ser  Lys  Thr  Ala  Asn  Tyr  Leu  Ile  Ser
                    85                       90                       95

Ile  Asp  Pro  Thr  Asn  Leu  Ser  Arg  Gly  Gly  Glu  Asn  Phe  Ile  Gly  Lys
                    100                      105                      110

Leu  Arg  Ser  Asn  Leu  Leu  Gly  Asn  Arg  Phe  Thr  Val  Phe  Asp  Asn  Gly
               115                      120                      125

Gln  Asn  Pro  Gln  Arg  Gly  Tyr  Ser  Thr  Asn  Val  Ala  Ser  Leu  Arg  Gln
     130                      135                      140

Glu  Leu  Ala  Ala  Val  Ile  Tyr  Glu  Thr  Asn  Val  Leu  Gly  Phe  Arg  Gly
145                      150                      155                      160

Pro  Arg  Arg  Met  Thr  Val  Ile  Ile  Pro  Gly  Met  Ser  Ala  Glu  Asn  Glu
                    165                      170                      175

Arg  Val  Pro  Ile  Arg  Pro  Arg  Asn  Ala  Ser  Asp  Gly  Leu  Leu  Val  Arg
                    180                      185                      190

Trp  Gln  Asn  Lys  Thr  Leu  Glu  Ser  Leu  Ile  Glu  Leu  His  Asn  Lys  Pro
               195                      200                      205
```

| | | | | | | | | | | | | | |
|---|---|---|---|---|---|---|---|---|---|---|---|---|---|
| Pro | Val | Trp | Asn | Asp | Asp | Ser | Gly | Ser | Tyr | Thr | Leu | Asn | Phe | Gln | Gly |
| | 210 | | | | | 215 | | | | | 220 | | | | |
| Arg | Val | Thr | Gln | Ala | Ser | Val | Lys | Asn | Phe | Gln | Ile | Val | His | Ala | Asp |
| 225 | | | | | 230 | | | | | 235 | | | | | 240 |
| Asp | Pro | Asp | Tyr | Ile | Val | Leu | Gln | Phe | Gly | Arg | Val | Ala | Glu | Asp | Ala |
| | | | | 245 | | | | | 250 | | | | | 255 | |
| Phe | Thr | Leu | Asp | Tyr | Arg | Tyr | Pro | Leu | Cys | Ala | Leu | Gln | Ala | Phe | Ala |
| | | | 260 | | | | | 265 | | | | | 270 | | |
| Ile | Ala | Leu | Ser | Ser | Phe | Asp | Gly | Lys | Leu | Ala | Cys | Glu | | | |
| | | | 275 | | | | 280 | | | | | 285 | | | |

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

CCGACTCGAT TGCCAGTGTA       20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GCGGATACAG ACTCTCTCAT       20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GTTCAAGCTG GTTTCAAGAT G       21

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

ATCATCCAGG GAAGATGGAC       20

(2) INFORMATION FOR SEQ ID NO:20:

(i) SEQUENCE CHARACTERISTICS:

(A) LENGTH: 19 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:20:

CTTCCTGGTG GAGGCAGTG 19

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:21:

GAAGCAGTGA CGGGATGTGG 20

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:22:

GGGTACCGAG CTCTGGTC 18

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:23:

TCCAAGTCAG GAGGACAAAC 20

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:24:

GAAAGTGCAT CTGAGAACCT G 21

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:25:

CCTCCTCCTG GATGTAACTC    20

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

TGTGACCATG TGTATTTCAG G    21

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

CCTCTAACGG ATGAGCAGTC    20

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

GATTTGGATC CCAGACCACC    20

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

GACTTCCAGT CACATTTCAG C    21

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

GTGCAGACCA GAGGCTGA    18

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

TTCAGGCCCT CTACAGACAG                                              20

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

TCATAGGACA GACGATGAGC                                              20

( 2 ) INFORMATION FOR SEQ ID NO:33:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

GTCCTGGATT TCATATCTAC C                                            21

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

AGGTAAATAG ACGCCTCAGG                                              20

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

ACGTCTGCCC TTAGAAGCTC                                              20

( 2 ) INFORMATION FOR SEQ ID NO:36:

( i ) SEQUENCE CHARACTERISTICS:

( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:36:

CTGGACCTGG CTCAGGTG 18

( 2 ) INFORMATION FOR SEQ ID NO:37:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:37:

GTCATTAGGG TTAGAAAGTT CC 22

( 2 ) INFORMATION FOR SEQ ID NO:38:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:38:

TCTTCCCTCA TGTGGTTTGG 20

( 2 ) INFORMATION FOR SEQ ID NO:39:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:39:

CCACAGGCAG GCAGGCAAG 19

( 2 ) INFORMATION FOR SEQ ID NO:40:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:40:

TGCGCAGAAA CAATCACCTA 20

( 2 ) INFORMATION FOR SEQ ID NO:41:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:41:

CAAGACGTGA ACCTGGA                                                                                                       17

( 2 ) INFORMATION FOR SEQ ID NO:42:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

GCGGATACAG ACTCTCTCAT                                                                                                    20

( 2 ) INFORMATION FOR SEQ ID NO:43:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GAGGACAAAT GTCCTAGGCT                                                                                                    20

( 2 ) INFORMATION FOR SEQ ID NO:44:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CATGCTCCTT GGGATGT                                                                                                       17

( 2 ) INFORMATION FOR SEQ ID NO:45:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

TGAGGATTGC TTAAAGA                                                                                                       17

( 2 ) INFORMATION FOR SEQ ID NO:46:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

GAGACAAATG TCCTAGGCTT CAAGGGACCT CGGAAGATGA GTGTGATCGT CCCAGGCATG                                                         60

AACATGGTTC ATGAGAGAGT CTGTATCCGC                                     90

( 2 ) INFORMATION FOR SEQ ID NO:47:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

GGACAAGAAG GGGATGGAC                                                 19

( 2 ) INFORMATION FOR SEQ ID NO:48:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:48:

CCGTGGATGA TCTGGAAGT                                                 19

( 2 ) INFORMATION FOR SEQ ID NO:49:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

TGAGACAAAT GTCCTAGGCT                                                20

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:50:

TGGACAGAGC AATGGCGAAG                                                20

( 2 ) INFORMATION FOR SEQ ID NO:51:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

CCGACTCGAT TGCCAGTGTA                                                20

( 2 ) INFORMATION FOR SEQ ID NO:52:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:52:

GCGGATACAG ACTCTCTCAT 20

( 2 ) INFORMATION FOR SEQ ID NO:53:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:53:

CCGACTCGAT TGCCAGTGTA 20

( 2 ) INFORMATION FOR SEQ ID NO:54:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:54:

GGAGCTGTTT TCATCCTCAT C 21

( 2 ) INFORMATION FOR SEQ ID NO:55:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:55:

GAAGGAGAAG AAGGGAAAGC 20

( 2 ) INFORMATION FOR SEQ ID NO:56:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:56:

GGGTGTTACT ATTTAGCTGG 20

( 2 ) INFORMATION FOR SEQ ID NO:57:

( i ) SEQUENCE CHARACTERISTICS:
    ( A ) LENGTH: 20 base pairs
    ( B ) TYPE: nucleic acid
    ( C ) STRANDEDNESS: single ( D ) TOPOLOGY: linear ( i i ) MOLECULE TYPE: DNA ( x i ) SEQUENCE DESCRIPTION: SEQ ID NO:57:

TTCAAGAGGC CGACTCGATT 20

( 2 ) INFORMATION FOR SEQ ID NO:58:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:58:

TTCCTCTGCA TCGTGGCAC 19

( 2 ) INFORMATION FOR SEQ ID NO:59:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:59:

CACCACCACC ACCACCACTG AATTC 25

( 2 ) INFORMATION FOR SEQ ID NO:60:

( i ) SEQUENCE CHARACTERISTICS:
( A ) LENGTH: 9 amino acids
( B ) TYPE: amino acid
( C ) STRANDEDNESS:
( D ) TOPOLOGY: unknown ( x i ) SEQUENCE DESCRIPTION: SEQ ID NO:60:

Tyr Pro Tyr Asp Val Pro Asp Tyr Ala
1               5

( 2 ) INFORMATION FOR SEQ ID NO:61:

( i ) SEQUENCE CHARACTERISTICS:
( A ) LENGTH: 7 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:61:

Arg Lys Arg Lys Lys Ser Lys
1               5

( 2 ) INFORMATION FOR SEQ ID NO:62:

( i ) SEQUENCE CHARACTERISTICS:
( A ) LENGTH: 8 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:62:

Ile Pro Tyr Ser Val Leu Asp Asp
1               5

( 2 ) INFORMATION FOR SEQ ID NO:63:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:63:

Glu Ser Tyr Leu Ser Ser Ser Gly
1               5

( 2 ) INFORMATION FOR SEQ ID NO:64:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:64:

Thr Ser Tyr Gln Val Gln Glu Ala
1               5

( 2 ) INFORMATION FOR SEQ ID NO:65:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:65:

Gly Met Tyr Pro Thr Tyr Phe Leu
1               5

( 2 ) INFORMATION FOR SEQ ID NO:66:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:66:

Pro Thr Tyr Phe Leu His Leu Asp
1               5

( 2 ) INFORMATION FOR SEQ ID NO:67:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:67:

Ser Asn Tyr Leu Ile Ser Val Phe
1               5

(2) INFORMATION FOR SEQ ID NO:68:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:68:

Asp Ser Tyr Ile Gly Lys Leu Arg
1               5

(2) INFORMATION FOR SEQ ID NO:69:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:69:

Thr Val Tyr Asp Asn Gly Tyr Asn
1               5

(2) INFORMATION FOR SEQ ID NO:70:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:70:

Val Cys Tyr Glu Thr Asn Val Leu
1               5

(2) INFORMATION FOR SEQ ID NO:71:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:71:

Gln Ser Tyr Val Leu Asn Phe His
1               5

(2) INFORMATION FOR SEQ ID NO:72:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:72:

Met Asp Tyr Asn Tyr Pro Leu Cys
 1               5

( 2 ) INFORMATION FOR SEQ ID NO:73:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:73:

Tyr Asn Tyr Pro Leu Cys Ala Leu
 1               5

( 2 ) INFORMATION FOR SEQ ID NO:74:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:74:

Gly Arg Lys Arg Lys Lys
 1               5

( 2 ) INFORMATION FOR SEQ ID NO:75:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:75:

Gly Pro Arg Lys
 1

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:76:

AATTAACCCT CACTAAAGGG        20

( 2 ) INFORMATION FOR SEQ ID NO:77:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:77:

AATTAACCCT CACTAAAGGG CCGACTCGAT TGCCAGTGTA 40

( 2 ) INFORMATION FOR SEQ ID NO:78:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:78:

CGGGATACAG ACTCTCTCAT 20

( 2 ) INFORMATION FOR SEQ ID NO:79:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:79:

TAATACGACT CACTATAGGG 20

( 2 ) INFORMATION FOR SEQ ID NO:80:

( i ) SEQUENCE CHARACTERISTICS:
          ( A ) LENGTH: 39 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:80:

TAATACGACT CACTATAGGG CGGATACAGA CTCTCTCAT 39

( 2 ) INFORMATION FOR SEQ ID NO:81:

( i ) SEQUENCE CHARACTERISTICS:
          ( A ) LENGTH: 5 amino acids
          ( B ) TYPE: amino acid
          ( C ) STRANDEDNESS:
          ( D ) TOPOLOGY: unknown ( i i ) MOLECULE TYPE: peptide ( x i ) SEQUENCE DESCRIPTION: SEQ ID NO:81:

Lys Leu Ala Cys Glu
 1                        5

( 2 ) INFORMATION FOR SEQ ID NO:82:

( i ) SEQUENCE CHARACTERISTICS:
          ( A ) LENGTH: 12 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:82:

GGATCCACCA TG 12